(12) United States Patent
Beigelman et al.

(10) Patent No.: US 11,466,274 B2
(45) Date of Patent: Oct. 11, 2022

(54) MODIFIED GAPMER OLIGONUCLEOTIDES AND METHODS OF USE

(71) Applicant: Aligos Therapeutics, Inc., South San Francisco, CA (US)

(72) Inventors: Leonid Beigelman, South San Francisco, CA (US); Rajendra K. Pandey, South San Francisco, CA (US); Vivek Kumar Rajwanshi, South San Francisco, CA (US); David Bernard Smith, South San Francisco, CA (US); Jin Hong, South San Francisco, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/887,063

(22) Filed: May 29, 2020

(65) Prior Publication Data

US 2020/0385735 A1 Dec. 10, 2020

Related U.S. Application Data

(60) Provisional application No. 62/943,532, filed on Dec. 4, 2019, provisional application No. 62/937,760, filed on Nov. 19, 2019, provisional application No. 62/855,793, filed on May 31, 2019.

(51) Int. Cl.
| | | |
|---|---|---|
| *C12N 15/11* | (2006.01) | |
| *C12N 15/113* | (2010.01) | |
| *A61P 31/20* | (2006.01) | |
| *A61K 31/7125* | (2006.01) | |

(52) U.S. Cl.
CPC ...... *C12N 15/1131* (2013.01); *A61K 31/7125* (2013.01); *A61P 31/20* (2018.01); *C12N 2310/11* (2013.01); *C12N 2310/315* (2013.01); *C12N 2310/341* (2013.01); *C12N 2320/31* (2013.01)

(58) Field of Classification Search
CPC ............ C12N 15/1131; C12N 2310/11; C12N 2310/341
See application file for complete search history.

(56) References Cited

U.S. PATENT DOCUMENTS

| | | | |
|---|---|---|---|
| 6,525,191 B1 | 2/2003 | Ramasamy | |
| 7,687,617 B2 | 3/2010 | Thrue et al. | |
| 8,541,562 B2 | 9/2013 | Obika et al. | |
| 8,580,756 B2 | 11/2013 | Hansen et al. | |
| 9,034,841 B2 | 5/2015 | Swayze et al. | |
| 9,428,534 B2 | 8/2016 | Christensen et al. | |
| 9,611,479 B2 | 4/2017 | Obika et al. | |
| 9,708,614 B2 | 7/2017 | Christensen et al. | |
| 9,932,580 B2 | 4/2018 | Prakash et al. | |
| 10,077,443 B2 | 9/2018 | Albaek et al. | |
| 10,358,643 B2 | 7/2019 | Albaek et al. | |
| 10,377,789 B2 | 8/2019 | Obika et al. | |
| 10,421,967 B2 | 9/2019 | Javanbakh et al. | |
| 2004/0127446 A1 | 7/2004 | Blatt et al. | |
| 2006/0063731 A1 | 3/2006 | Lewis et al. | |
| 2015/0368642 A1 | 12/2015 | Alb et al. | |
| 2017/0327524 A1 | 11/2017 | Albaek et al. | |
| 2018/0016575 A1 | 1/2018 | Hansen et al. | |
| 2018/0112217 A1 | 4/2018 | Hansen et al. | |
| 2018/0251764 A1 | 9/2018 | Albaek et al. | |
| 2018/0296684 A1 | 10/2018 | Seth et al. | |
| 2019/0071672 A1 | 3/2019 | Elmen et al. | |
| 2019/0169610 A1 | 6/2019 | Freier et al. | |
| 2020/0055890 A1 | 2/2020 | Obika et al. | |
| 2020/0056178 A1 | 2/2020 | Obika et al. | |
| 2020/0147124 A1 | 5/2020 | Beigelman et al. | |

FOREIGN PATENT DOCUMENTS

| | | | |
|---|---|---|---|
| EP | 3 353 305 | 8/2018 | |
| WO | WO-2011/047312 A1 | 4/2011 | |
| WO | WO-2011/052436 A1 | 5/2011 | |
| WO | WO-2012/145697 A1 | 10/2012 | |
| WO | WO-2013/159108 A2 | 10/2013 | |
| WO | WO-2014/043212 A2 | 3/2014 | |
| WO | WO-2015/125783 A1 | 8/2015 | |
| WO | WO-2015173208 A2 * | 11/2015 | ............. A61P 31/12 |
| WO | WO-2018/155450 A1 | 8/2018 | |
| WO | WO-2018/155451 A1 | 8/2018 | |
| WO | PCT/US2020/026116 | 4/2020 | |
| WO | PCT/US2020/028349 | 4/2020 | |
| WO | WO-2020/097342 A1 | 5/2020 | |
| WO | WO-2020/167984 A1 | 8/2020 | |

OTHER PUBLICATIONS

U.S. Appl. No. 16/789,298, filed Feb. 12, 2020, Leonid Beigelman et al.
U.S. Appl. No. 16/837,515, filed Apr. 1, 2020, Sandrine Vendeville et al.
U.S. Appl. No. 16/849,851, filed Apr. 15, 2020, Sandrine Vendeville et al.
Berke et al., "Capsid Assembly Modulators Have a Dual Mechanism of Action in Primary Human Hepatocytes Infected with Hepatitis B Virus," Antimicrobial Agents and Chemotherapy, 2017, 61:e00560-17.
Horiba et al., "Synthesis of scpBNA-mC, -A and -G Monomers and Evaluation of the Binding Affinities of scpBNA-Modified Oligonucleotides toward Complementary ssRNA and ssDNA," The Journal of Organic Chemistry, 2016, 81:11000-11008.

(Continued)

*Primary Examiner* — Ekaterina Poliakova-Georgantas
(74) *Attorney, Agent, or Firm* — Foley & Lardner LLP

(57) ABSTRACT

The disclosure includes antisense oligonucleotides, including gapmer antisense oligonucleotides, along with methods of making and use, e.g., against HBV.

16 Claims, 22 Drawing Sheets

Specification includes a Sequence Listing.

(56) References Cited

OTHER PUBLICATIONS

Klumpp et al,. "Efficacy of NVR 3-778, Alone and in Combination with Pegylated Interferon, vs Entecavir in uPA/SCID Mice with Humanized Livers and HBV infection," Gastroenterology, 2018, 154:652-662.
Sung et al., "Genome-wide survey of recurrent HBV integration in hepatocellular carcinoma," Nature Genetics, Jul. 2012, 44(7):765-.
Yamaguchi et al., "Synthesis and properties of 2'-O-4'-C-spirocyclopropylene bridged nucleic acid (scpBNA), an analogue of 1',4'-BNA/LNA bearing a cyclopropane ring," ChemComm, 2015, 51:9737-9740.
"Hepatitis B virus isolate M0914, complete genome—Nucleotide—NCBI", Mar. 20, 2013, XP055740458, Retrieved from the Internet: URL:https://ncbi.nlm.nih.gov/nuccore/KC315400.1?report=genbank&log$=seqview [retrieved on Oct. 15, 2020], 3 pages.
Deng et al., "Antiviral effect of hepatitis B virus S/C gene loci antisense locked nucleic acid on transgenic mice in vivo", Genetics and Molecular Research, 2015, pp. 10087-10095, vol. 14, No. 3.
Invitation to Pay Additional Fees and, Where Applicable, Protest Fee, and partial International Search Report issued in International Patent Application No. PCT/US2020/035212, dated Oct. 30, 2020.
Javanbakht et al., "Liver-Targeted Anti-HBV Single-Stranded Oligonucleotides with Locked Nucleic Acid Potently Reduce HBV Gene Expression In Vivo", Molecular Therapy: Nucleic Acids, Jun. 2018, pp. 441-454, vol. 11.
Yao et al., "inhibition of Hepatitis B Virus In Vitro by Antisense Oligonucleotides", Acta Virologica, 1996, pp. 30-39, vol. 40.

\* cited by examiner

ASO 126 Dose Response Curves

ASO 120 Dose Response Curves

ASO 124 Dose Response Curves

ASO 127 Dose Response Curves

ASO 121 Dose Response Curves

ASO 125 Dose Response Curves

MODIFIED GAPMER OLIGONUCLEOTIDES AND METHODS OF USE

CROSS-REFERENCE TO RELATED APPLICATIONS

This application claims priority to U.S. Provisional Application No. 62/943,532, filed Dec. 4, 2019, U.S. Provisional Application No. 62/937,760, filed Nov. 19, 2019, and U.S. Provisional Application No. 62/855,793, filed May 31, 2019, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 8, 2020, is named 122400-0132_SL.txt and is 108,366 bytes in size.

BACKGROUND

About 300 million people are chronically infected with HBV worldwide. HBsAg loss, a key aspect of "functional cure" is the goal of many new therapies. Antisense oligonucleotides have been demonstrated to be an effective modality in reducing HBsAg in animal models and clinical studies with these molecules are ongoing.

However, the treatments of HBV with antisense oligonucleotides still suffer from, e.g., nuclease degradation and liver toxicity. Thus, there is a need in the art to discover antisense oligonucleotides having greater resistance to nuclease degradation and improved liver safety profiles.

SUMMARY

The present disclosure relates to compounds and compositions containing oligonucleotides and their use in preventing or treating diseases and conditions, e.g., hepatitis B (HBV).

Some embodiments include a method of treating a subject having a Hepatitis B virus (HBV) infection, comprising administering to the subject a first antisense oligonucleotide (ASO) and a second ASO, wherein the first and second ASO each independently contain 14-22 nucleotide units, and the first and second ASO each independently contain: (a) a central region (B') comprising 6 or more contiguous DNA nucleosides, (b) a 5'-wing region (A') comprising 2 to 6 locked nucleosides or 2' substituted nucleosides, and (c) a 3'-wing region (C') comprising 2 to 6 locked nucleosides or 2' substituted nucleosides, wherein the first ASO is complementary or hybridizes to a viral target RNA sequence in a first X region or a first S region of HBV, and the second ASO is complementary or hybridizes to a viral target RNA sequence in a second X region or a second S region of HBV.

In some embodiments, a method of treating a subject having a Hepatitis B virus (HBV) infection comprises administering to the subject a first antisense oligonucleotide (ASO), wherein the first ASO contains 14-22 nucleotide units, and the first ASO contains: (a) a central region (B') comprising 6 or more contiguous DNA nucleosides, (b) a 5'-wing region (A') comprising 2 to 6 locked nucleosides or 2' substituted nucleosides, and (c) a 3'-wing region (C') comprising 2 to 6 locked nucleosides or 2' substituted nucleosides, wherein the first ASO is complementary or hybridizes to a viral target RNA sequence in a first X region or a first S region of HBV. In some embodiments, the method further comprises administering to the subject a second ASO, wherein the second ASO contains 14-22 nucleotide units, and the second ASO contains: (a) a central region (B') comprising 6 or more contiguous DNA nucleosides, (b) a 5'-wing region (A') comprising 2 to 6 locked nucleosides or 2' substituted nucleosides, and (c) a 3'-wing region (C') comprising 2 to 6 locked nucleosides or 2' substituted nucleosides, and the second ASO is complementary or hybridizes to a viral target RNA sequence in a second X region or a second S region of HBV.

In some embodiments, the 5'-wing region of at least one of the first and second ASO comprises 2 to 6 phosphorothioate-linked locked nucleosides. In some embodiments, the 5'-wing region of at least one of the first and second ASO comprises 2 to 6 phosphorothioate-linked 2' substituted nucleosides. In some embodiments, the 5'-wing region of at least one of the first and second ASO comprises at least one locked nucleoside and at least one 2' substituted nucleoside, wherein the locked nucleoside and the 2' substituted nucleoside are linked by a phosphorothiate linker. In some embodiments, the 5'-wing region of at least one of the first and second ASO further comprises a RNA nucleoside or DNA nucleoside, wherein the RNA nucleoside and DNA nucleoside are not locked nucleosides or 2'-substituted nucleosides. In some embodiments, at least two nucleosides of the 5'-wing region of at least one of the first and second ASO are linked by a phosphorothioate linker. In some embodiments, at least 2, 3, 4, 5, or 6 nucleosides of the 5'-wing region of at least one of the first and second ASO are linked by a phosphorothioate linker. In some embodiments, the 3'-wing region of at least one of the first and second ASO comprises 2 to 6 phosphorothioate-linked locked nucleosides. In some embodiments, the 3'-wing region of at least one of the first and second ASO comprises 2 to 6 2' phosphorothioate-linked substituted nucleosides. In some embodiments, the 3'-wing region of at least one of the first and second ASO comprises at least one locked nucleoside and at least one 2' substituted nucleoside, wherein the locked nucleoside and the 2' substituted nucleoside are linked by a phosphorothiate linker. In some embodiments, the 3'-wing region of at least one of the first and second ASO further comprises a RNA nucleoside or DNA nucleoside, wherein the RNA nucleoside and DNA nucleoside are not locked nucleosides or 2'-substituted nucleosides. In some embodiments, at least two nucleosides of the 3'-wing region of at least one of the first and second ASO are linked by a phosphorothioate linker. In some embodiments, at least 2, 3, 4, 5, or 6 nucleosides of the 3'-wing region of at least one of the first and second ASO are linked by a phosphorothioate linker. In some embodiments, the central region of at least one of the first and second ASO comprises at least 5 contiguous phosphorothioate-linked DNA nucleosides. In some embodiments, at least 2, 3, 4, 5, or 6 nucleosides of the central region of at least one of the first and second ASO are linked by a phosphorothioate linker. In some embodiments, a DNA nucleoside of central region of at least one of the first and second ASO is linked to a nucleoside of a 5'-wing region of at least one of the first and second ASO by a phosphorothioate linker. In some embodiments, a DNA nucleoside of central region of at least one of the first and second ASO is linked to a nucleoside of a 3'-wing region of at least one of the first and second ASO by a phosphorothioate linker. In some embodiments, the central region of at least one of the first and second ASO each independently comprises 8 to 10 contiguous phosphorothioate-linked DNA nucleosides. In some embodiments, the locked nucleosides are selected from LNA, scpBNA, AmNA (N—H), AmNA (N-Me), GuNA, GuNA (N—R) where R is selected from Me, Et, i-Pr, t-Bu and combinations thereof. In some embodiments, the second ASO is complementary or hybridizes to the viral target RNA sequence in the second X region of HBV. In some embodiments, the second ASO is complementary or hybridizes to the viral target RNA sequence in the S region of HBV. In some embodiments, the first and/or second ASO further comprises a targeting group. In some embodiments, the targeting group comprises a GalNAc moiety. In some embodiments, the first and second ASO each independently contain 14-18 nucleotide units. In some embodiments, the first and second ASO are administered concurrently. In some embodiments, the first and second ASO are administered consecutively. In some embodiments, the subject is a mammal. In some embodiments, the mammal is an adult human. In some embodiments, the treatment comprises reducing a viral load of HBV in the subject. In some embodiments, the treatment comprises reducing a level of a virus antigen in the subject. In some embodiments, the first ASO comprises a nucleotide sequence that is at least 90% identical to a nucleotide sequence selected from the sequences listed in Table 1, 2A, 3, 4, 7, 8, 9, 10, 11, 13, 14, or 19. In some embodiments, the second ASO comprises a nucleotide sequence that is at least 90% identical to a nucleotide sequence selected from the sequences in Table 1, 2A, 3, 4, 7, 8, 9, 10, 11, 13, 14, or 19. In some embodiments, the first ASO comprises a nucleotide sequence that is at least 90% identical to a nucleotide sequence of any one of SEQ ID NOs: 2-428. In some embodiments, the second ASO comprises a nucleotide sequence that is at least 90% identical to a nucleotide sequence of any one of SEQ ID NOs: 2-428. In some embodiments, the first ASO is ASO 120 or ASO 121. In some embodiments, the second ASO is ASO 120 or ASO 121.

Some embodiments include a pharmaceutical composition comprising a first antisense oligonucleotide (ASO) and a second ASO, wherein the first and second ASO each independently contain 14-22 nucleotide units, and the first and second ASO each independently contain: (a) a central region (B') comprising 6 or more contiguous DNA nucleosides, (b) a 5'-wing region (A') comprising 2 to 6 locked nucleosides or 2' substituted nucleosides, and (c) a 3'-wing region (C') comprising 2 to 6 locked nucleosides or 2' substituted nucleosides, wherein the first ASO is complementary or hybridizes to a viral target RNA sequence in a first X region of HBV, and the second ASO is complementary or hybridizes to a viral target RNA sequence in a second X region or an S region of HBV. In some embodiments, the 5'-wing region of at least one of the first and second ASO further comprises a RNA nucleoside or DNA nucleoside, wherein the RNA nucleoside and DNA nucleoside are not locked nucleosides or 2'-substituted nucleosides. In some embodiments, at least 2, 3, 4, 5, or 6 nucleosides of the 5'-wing region of at least one of the first and second ASO are linked by a phosphorothioate linker. In some embodiments, the 3'-wing region of at least one of the first and second ASO further comprises a RNA nucleoside or DNA nucleoside, wherein the RNA nucleoside and DNA nucleoside are not locked nucleosides or 2'-substituted nucleosides. In some embodiments, at least 2, 3, 4, 5, or 6 nucleosides of the 3'-wing region of at least one of the first and second ASO are linked by a phosphorothioate linker. In some embodiments, at least 2, 3, 4, 5, 6, 7, 8, 9, 10, 11, or 12 nucleosides of the central region of at least one of the first and second ASO are linked by a phosphorothioate linker. In some embodiments, a DNA nucleoside of central region of at least one of the first and second ASO is linked to a nucleoside of a 5'-wing region of at least one of the first and second ASO by a phosphorothioate linker. In some embodiments, a DNA nucleoside of central region of at least one of the first and second ASO is linked to a nucleoside of a 3'-wing region of at least one of the first and second ASO by a phosphorothioate linker.

Other embodiments include an antisense oligonucleotide comprising a nucleotide sequence that is at least 90% identical to a nucleotide sequence selected from the sequences listed in Table 1, 2A, 3, 4, 7, 8, 9, 10, 11, 13, 14, or 19. In some embodiments, the ASO further comprises a targeting moiety. In some embodiments, the targeting moiety comprises a GalNAc moiety. In some embodiments, the targeting moiety comprises three consecutive GalNAc moieties attached through linkers.

Other embodiments include an antisense oligonucleotide comprising a nucleotide sequence that is at least 90% identical to a nucleotide sequence of any one of SEQ ID NOs: 2-428. In some embodiments, the ASO further comprises a targeting moiety. In some embodiments, the targeting moiety comprises a GalNAc moiety. In some embodiments, the targeting moiety comprises three consecutive GalNAc moieties attached through linkers.

Additional embodiments include a method of treating a subject having a Hepatitis B virus (HBV) infection, comprising administering to the subject a therapeutically effective amount of one or more ASO of any of the preceding embodiments.

Some embodiments include methods of any of the preceding embodiments, further comprising administering to the patient an additional HBV treatment agent, such as a nucleotide analog, a capsid assembly modulator or another oligonucleotide. In some embodiments, the additional HBV treatment agent is selected from the group consisting of include STOPS™ ALG-010133, Capsid Assembly Modulator ALG-000184, recombinant interferon alpha 2b, IFN-α, PEG-IFN-α-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, DCR-HBVS, JNJ-6379, GLS4, ABI-H0731, JNJ-440, NZ-4, RG7907, EDP-514, AB-423, AB-506, ABI-H03733 and ABI-H2158. In some embodiments, the GalNAc moiety comprises one GalNAc moiety or three consecutive GalNAc moieties attached through linkers, wherein the GalNAc moiety is GalNAc-4 or GalNAc-6.

Some embodiments include methods of any of the preceding embodiments, wherein the patient has been treated with an additional HBV treatment agent, such as a nucleotide analog, a capsid assembly modulator or another oligonucleotide.

DETAILED DESCRIPTION

Figure 1A:
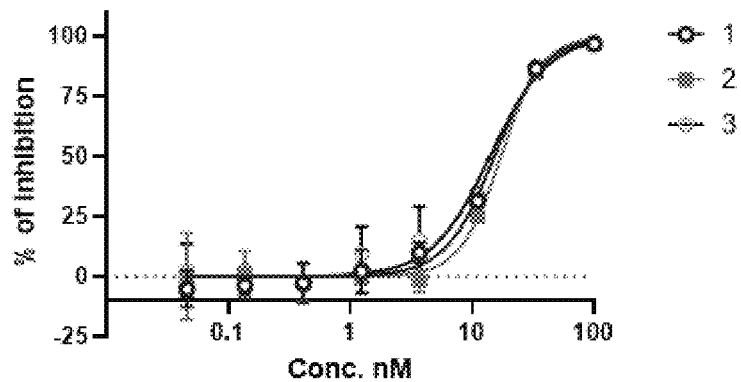
FIG. 1A shows the dose response curves for ASO 126 in HepG2.215 cells from three experiments.
Figure 1B:
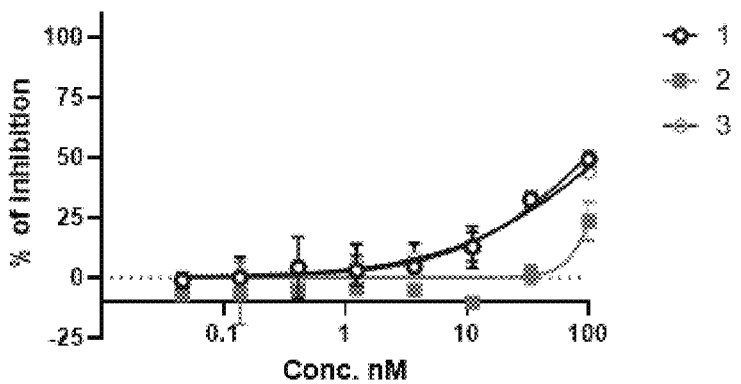
FIG. 1B shows the dose response curves for ASO 120 in HepG2.215 cells from three experiments.
Figure 1C:
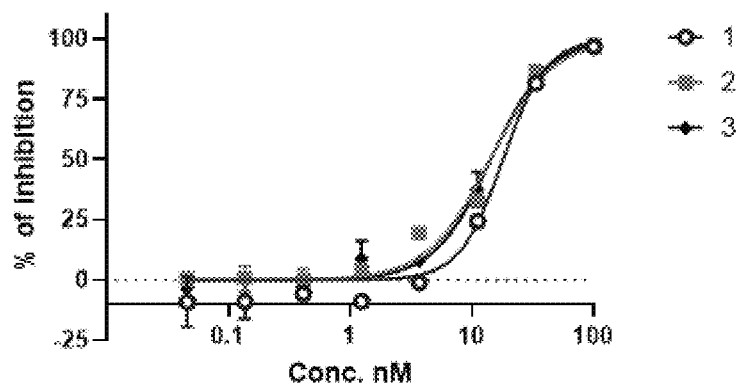
FIG. 1C shows the dose response curves for ASO 124 in HepG2.215 cells from three experiments.
Figure 2A:
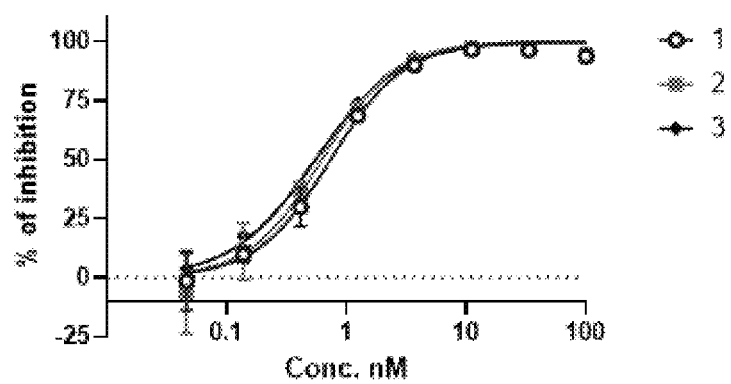
FIG. 2A shows the dose response curves for ASO 127 in HepG2.215 cells from three experiments.
Figure 2B:
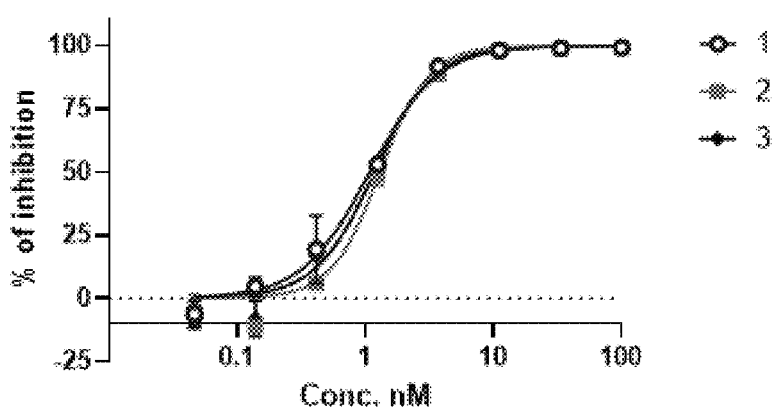
FIG. 2B shows the dose response curves for ASO 121 in HepG2.215 cells from three experiments.
Figure 2C:
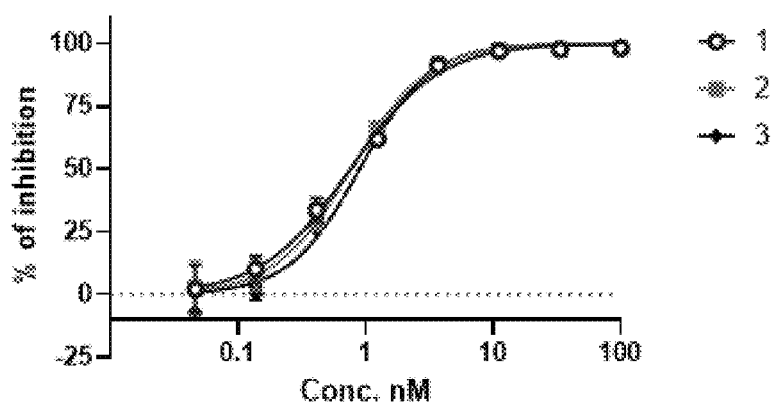
FIG. 2C shows the dose response curves for ASO 125 in HepG2.215 cells from three experiments.

The present disclosure is directed to modified antisense oligonucleotides and pharmaceutical compositions of modified antisense oligonucleotides. The present disclosure is also directed to methods of using and preparing the antisense oligonucleotides and pharmaceutical compositions.

Compounds of the Present Disclosure

Compounds of the present disclosure include modified antisense oligonucleotides (ASO). In some embodiments, the ASO comprises 14-22 nucleotide units, e.g., 14, 15, 16, 17, 18, 19, 20, 21, or 22 nucleotide units. In some embodiments, the ASO is a gapmer that comprises three regions: a 5'-wing region (A') comprising modified nucleotides; a central region (B') comprising nucleotides of a different type from the wings, e.g., nucleotides capable of inducing RNase H cleavage; and a 3'-wing region (C') comprising modified nucleotides.

In some embodiments, the 5'-wing region and the 3'-wing region comprise 2-6 nucleotides, e.g., 2, 3, 4, 5, or 6 nucleotides. One or more of these nucleotides is modified (e.g., 1, 2, 3, 4, 5, or 6 of the nucleotides is modified). On the other hand, the central region may comprise 6 or more contiguous DNA nucleosides, linked by phosphodiester or thiophosphate ("ps") internucleotide linkages. In other embodiments, the central region includes one or more modified nucleotide. For example, the central region may include one or more modified nucleotide where the central region is capable of inducing RNase H cleavage. In some embodiments, the central region includes one or more modified nucleotide having a modified nucleobase. In some embodiments, the central region comprises 6, 7, 8, 9, 10, or 11 contiguous DNA nucleosides. In some embodiments, 1, 2, 3, 4, 5, 6, 7, 8, 9, 10, or 11 of the DNA nucleosides in the central region are modified.

Thus, in some aspects, the gapmer ASO compounds of the disclosure include compounds of formula (I):

wherein A' and C' each independently comprise 2-6 nucleotides, with one or more being a modified nucleotide, B' comprises 6 or more contiguous DNA nucleosides linked by phosphodiester or thiophosphate internucleotide linkages. In some embodiments, B' comprises one or more modified DNA nucleosides. In some embodiments, the modified nucleotide is selected from locked nucleosides or 2'-substituted nucleosides. In some embodiments, the modified DNA nucleoside is selected from locked nucleosides or 2'-substituted nucleosides.

In certain aspects the number of nucleotides and/or nucleosides in A', B', and C' are selected from the following group (A':B':C'): (2:10:2), (2:10:3), (2:10:4), (2:10:5), (3:10:2), (3:10:3), (3:10:4), (3:10:5), (4:10:2), (4:10:3), (4:10:4), (4:10:5), (5:10:2), (5:10:3), (5:10:4), (5:10:5), (2:9:2), (2:9:3), (2:9:4), (2:9:5), (3:9:2), (3:9:3), (3:9:4), (3:9:5), (4:9:2), (4:9:3), (4:9:4), (4:9:5), (5:9:2), (5:9:3), (5:9:4), (5:9:5), (2:8:2), (2:8:3), (2:8:4), (2:8:5), (3:8:2), (3:8:3), (3:8:4), (3:8:5), (4:8:2), (4:8:3), (4:8:4), (4:8:5), (5:8:2), (5:8:3), (5:8:4), (5:8:5), (2:7:2), (2:7:3), (2:7:4), (2:7:5), (3:7:2), (3:7:3), (3:7:4), (3:7:5), (4:7:2), (4:7:3), (4:7:4), (4:7:5), (5:7:2), (5:7:3), (5:7:4), (5:7:5), (2:6:2), (2:6:3), (2:6:4), (2:6:5), (3:6:2), (3:6:3), (3:6:4), (3:6:5), (4:6:2), (4:6:3), (4:6:4), (4:6:5), (5:6:2), (5:6:3), (5:6:4), (5:6:5).

In some embodiments, the 5'-wing region comprises one or more locked nucleosides or 2'-substituted nucleosides. In some embodiments, the 3'-wing region comprises one or more locked nucleosides or 2'-substituted nucleosides. In some embodiments, the central region comprises one or more locked nucleosides or 2'-substituted nucleosides. The locked nucleoside can contain a bridge between the 4' and the 2' position of the sugar wherein the bridges comprises 2 to 4 optionally substituted atoms. For example, LNA nucleoside is:

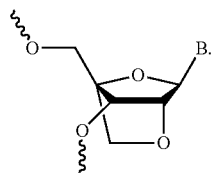

Other exemplary locked nucleosides include the following:

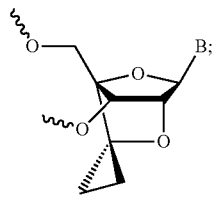

(ScpBNA or "cp")

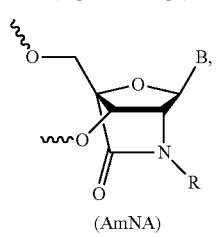

(AmNA)

where R is H or alkyl (or AmNA(N-Me)) when R is alkyl);

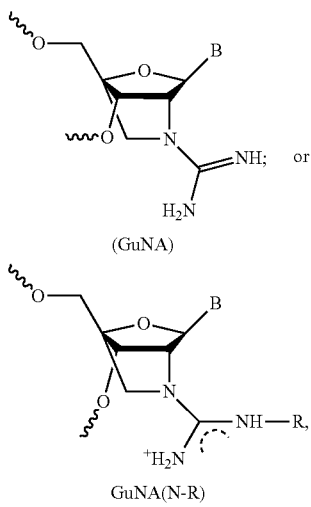

R = Me, Et, i-Pr, tBu.

In certain embodiments, all nucleosides in the 5'-wing region are locked nucleosides. In some embodiments, all nucleosides in the 3'-wing region are locked nucleosides. In some embodiments, the 3'-wing region comprises LNA and one or two nucleosides selected from ScpBNA, AmNA, and GuNA. In some embodiments, 5'-wing region are all LNA and the 3'-wing region contains LNA and one or two nucleosides selected from ScpBNA, AmNA, and GuNA. Other nucleotides are included in PCT/JP2010/068409, PCT/JP2013/075370, PCT/JP2015/054308, PCT/JP2018/006061, and/or PCT/JP2018/006062, which are incorporated by reference in their entirety.

In some embodiments, the 5'-wing region of an ASO comprises 2 to 6 phosphorothioate-linked locked nucleosides. In some embodiments, the 5'-wing region comprises 2 to 6 phosphorothioate-linked 2' substituted nucleosides. In some embodiments, the 5'-wing region comprises at least one locked nucleoside and at least one 2' substituted nucleoside, wherein the locked nucleoside and the 2' substituted nucleoside are linked by a phosphorothiate linker. In some embodiments, the 5'-wing region further comprises a RNA nucleoside or DNA nucleoside, wherein the RNA nucleoside and DNA nucleoside are not locked nucleosides or 2'-substituted nucleosides. In some embodiments, at least two nucleosides of the 5'-wing region are linked by a phosphorothioate linker. In some embodiments, at least 2, 3, 4, 5, or 6 nucleosides of the 5'-wing region are linked by a phosphorothioate linker.

In some embodiments, the 3'-wing region of an ASO comprises 2 to 6 phosphorothioate-linked locked nucleosides. In some embodiments, the 3'-wing region comprises 2 to 6 2' phosphorothioate-linked substituted nucleosides. In some embodiments, the 3'-wing region comprises at least one locked nucleoside and at least one 2' substituted nucleoside, wherein the locked nucleoside and the 2' substituted nucleoside are linked by a phosphorothiate linker. In some embodiments, the 3'-wing region further comprises a RNA nucleoside or DNA nucleoside, wherein the RNA nucleoside and DNA nucleoside are not locked nucleosides or 2'-substituted nucleosides. In some embodiments, at least two nucleosides of the 3'-wing region are linked by a phosphorothioate linker. In some embodiments, at least 2, 3, 4, 5, or 6 nucleosides of the 3'-wing region are linked by a phosphorothioate linker.

In certain embodiments, one or more of the nucleotides in the 5'-wing region and/or the 3'-wing region comprises a thiophosphate internucleotide linkage. In certain embodiments, all nucleotides in the 5'-wing region comprises a thiophosphate internucleotide linkage. In some embodiments, all nucleotides in the 3'-wing region comprises a thiophosphate internucleotide linkage.

In some embodiments, the central region includes one or more modified nucleotide having a modified nucleobase. For example, the central region can include one or more modified nucleotide having a protected or unprotected version of the following:

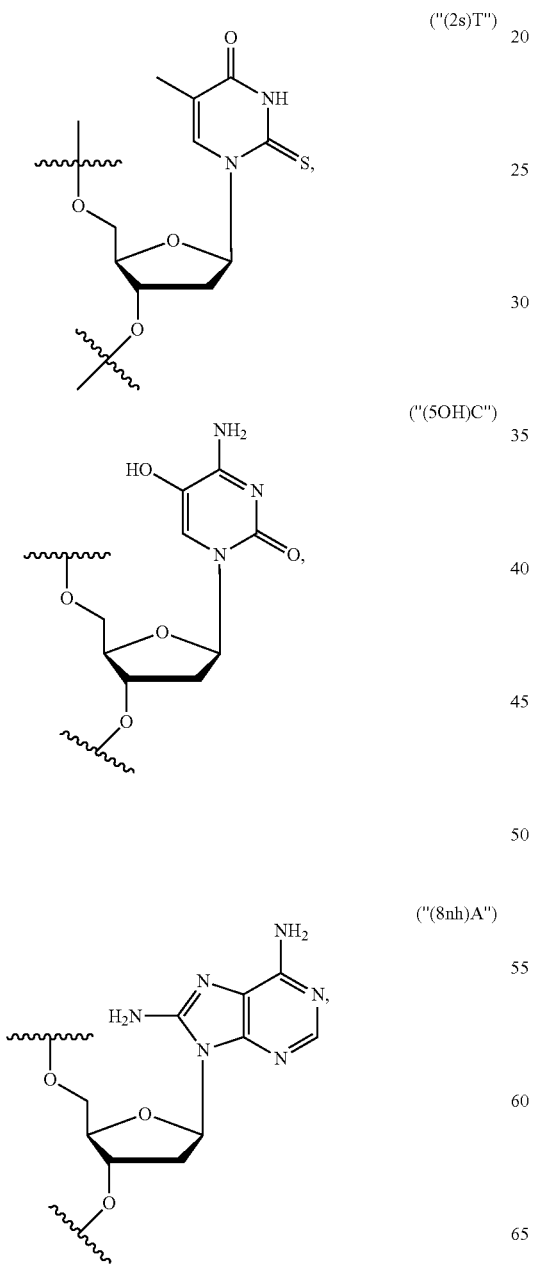

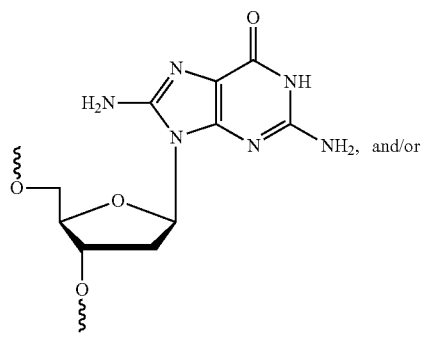

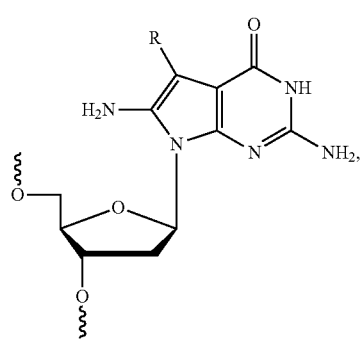

where R is a halogen or R'—C≡C—; and R' is $C_{6-12}$ aryl, 5- to 12-membered heteroaryl, hydroxy-$C_{1-6}$ alkyl, or $C_{1-7}$ alkanoyloxy. In some embodiments, the central region includes one modified nucleotide (e.g., (2s)T or (5OH)C) at the $1^{st}$, $2^{nd}$, $3^{rd}$ or $4^{th}$ gap nucleoside position (from the 5' end). In some embodiments, the modified nucleotide is at the $3^{rd}$ gap nucleoside position (from the 5' end). In some embodiments, the modified nucleotide is a nucleotide having the structure of:

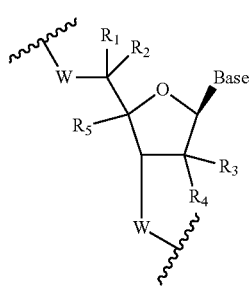

wherein:

W is independently O, N, or S;

$R_1$, $R_2$, and $R_5$ are independently H or D;

$R_3$ is H or F;

$R_4$ is F or $OCH_3$; and

Base is

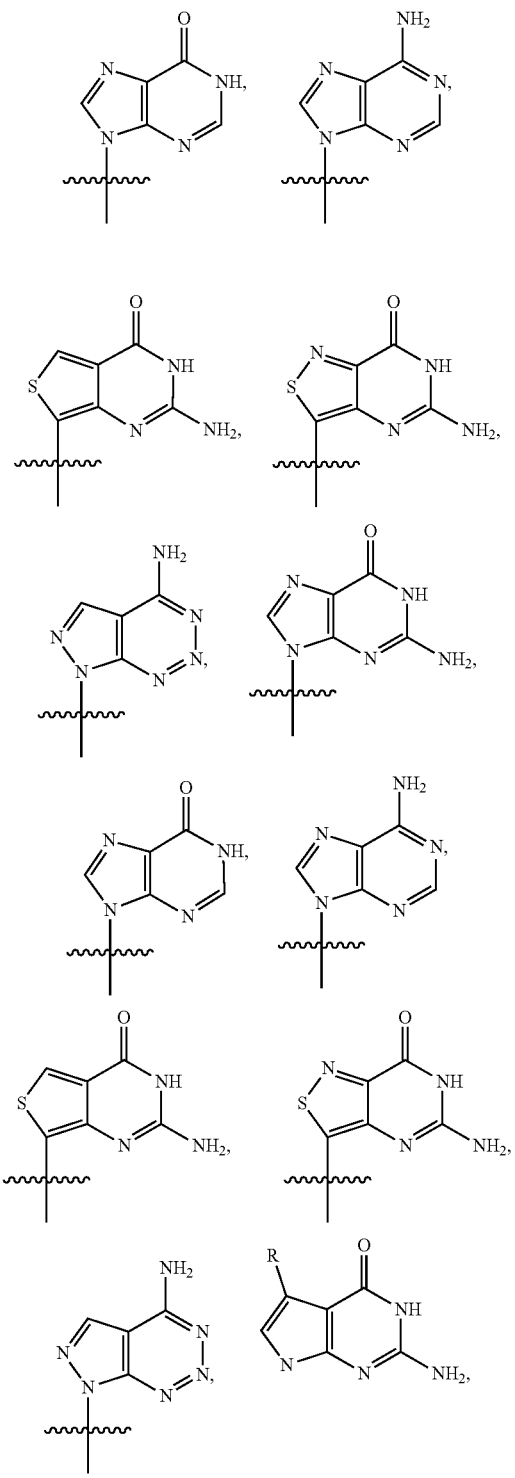

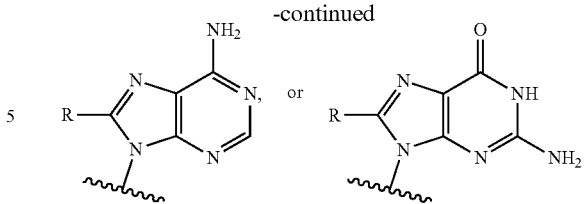

wherein:

R is a halogen or R'—C≡C—; and

R' represents $C_{6-12}$ aryl, 5- to 12-membered heteroaryl, hydroxy-$C_{1-6}$ alkyl, or $C_{1-7}$ alkanoyloxy. In some embodiments, $C_{1-7}$ alkanoyl includes, but is not limited to. formyl, acetyl, ethyl carbonyl, n-propyl carbonyl, isopropyl carbonyl, n-butyl carbonyl, isobutyl carbonyl, t-butyl carbonyl, n-pentyl carbonyl, and n-hexyl carbonyl. Other modified nucleotides include those in PCT/JP2018/006061, which is incorporated by reference in its entirety.

As used herein, unless otherwise indicated, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Examples of aryl groups include, without limitation, the radicals of benzene, naphthalene and azulene.

As used herein, unless otherwise indicated, "heteroaryl" refers to a ring that has a fully delocalized pi-electron system and contains one or more heteroatoms (e.g., one to three heteroatoms, or one to four heteroatoms, or one to five heteroatoms) independently selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, pyrrole, oxazole, thiazole, imidazole, pyrazole, isoxazole, isothiazole, triazole, thiadiazole, pyridine, pyridazine, pyrimidine, pyrazine and triazine.

In some embodiments, the central region of an ASO comprises at least 5 contiguous phosphorothioate-linked DNA nucleosides. In some embodiments, at least 2, 3, 4, 5, or 6 nucleosides of the central region are linked by a phosphorothioate linker. In some embodiments, a DNA nucleoside of central region is linked to a nucleoside of a 5'-wing region by a phosphorothioate linker. In some embodiments, a DNA nucleoside of central region is linked to a nucleoside of a 3'-wing region by a phosphorothioate linker. In some embodiments, the central region comprises 8 to 10 contiguous phosphorothioate-linked DNA nucleosides.

In some embodiments, the ASO is complementary or hybridizes to a viral target RNA sequence that begins in an X region of HBV or in an S region of HBV. The vital target may, e.g., begin at the 5'-end of target-site in acc. KC315400.1 (genotype B, "gt B"), or in any one of genotypes A, C, or D. The skilled person would understand the HBV position, e.g., as described in Wing-Kin Sung, et al., *Nature Genetics* 44:765 (2012). In some embodiments, the S region is defined as from the beginning of small S protein (in genotype B KC315400.1 isolate, position #155) to before beginning of X protein (in genotype B KC315400.1 isolate, position #1373). In some embodiments, the X region is defined as from the beginning X protein (in genotype B KC315400.1 isolate, position #1374) to end of DR2 site (in genotype B KC315400.1 isolate, position #1603).

In some embodiments, the ASO is complementary or hybridizes to a viral target RNA sequence that comprises, consists of, or consists essentially of at least 5, 6, 7, 8, 9, 10, 11, 12, 13, 14, or 15 contiguous nucleotides within positions 100-800 or 1050-1700 of SEQ ID NO: 1. In some embodiments, the ASO is complementary or hybridizes to a viral target RNA sequence that comprises, consists of, or consists essentially of 5 to 15, 5 to 14, 5 to 13, 5 to 12, 5 to 11, 5 to 10, 5 to 9, 5 to 8, 6 to 15, 6 to 14, 6 to 13, 6 to 12, 6 to 11, 6 to 10, 7 to 15, 7 to 14, 7 to 13, 7 to 12, or 7 to 11 contiguous nucleotides within positions 100-800 or 1050-1700 of SEQ ID NO: 1. In some embodiments, the ASO is complementary or hybridizes to a viral target RNA sequence that comprises, consists of, or consists essentially of at least 5, 6, 7, 8, 9, 10, 11, 12, 13, 14, or 15 contiguous nucleotides within positions 180-280, 300 to 450, 650 to 775, 1125 to 1300, or 1400 to 1650 of SEQ ID NO: 1. In some embodiments, the ASO is complementary or hybridizes to a viral target RNA sequence that comprises, consists of, or consists essentially of at least 5, 6, 7, 8, 9, 10, 11, 12, 13, 14, or 15 contiguous nucleotides within positions 180 to 215, 230 to 270, 350 to 420, 675 to 730, 1165 to 1210, 1245 to 1290, 1400 to 1480, or 1500 to 1630 of SEQ ID NO: 1. In some embodiments, the ASO is complementary or hybridizes to a viral target RNA sequence that comprises, consists of, or consists essentially of at least 5, 6, 7, 8, 9, 10, 11, 12, 13, 14, or 15 contiguous starting at position 191, 245, 246, 276, 376, 377, 381, 383, 694, 700, 1182, 1261, 1262, 1408, 1410, 1426, 1431, 1432, 1433, 1435, 1438, 1441, 1443, 1513, 1516, 1517, 1518, 1519, 1520, 1521, 1522, 1527, 1559, 1575, 1576, 1577, 1580, 1581, 1582, or 1589 of SEQ ID NO: 1. In some embodiments, the ASO is perfectly complementary to the viral target RNA sequence. In some embodiments, there is less than or equal to 5, 4, 3, 2, or 1 mismatches between the ASO and the viral target sequence. In some embodiments, there is less than or equal to 2 mismatches between the ASO and the viral target sequence. In some embodiments, there is less than or equal to 1 mismatch between the ASO and the viral target sequence. In some embodiments, the mismatch is in the wing region of the ASO. In some embodiments, the mismatch is in the 5' wing region of the ASO. In some embodiments, the mismatch is in the 3' wing region of the ASO. In some embodiments, the mismatch is in the central region of the ASO.

In some embodiments, the central region is complementary or hybridizes to a viral target RNA sequence that comprises, consists of, or consists essentially of at least 5, 6, 7, 8, 9, 10, 11, 12, 13, 14, or 15 contiguous nucleotides within positions 100-800 or 1050-1700 of SEQ ID NO: 1. In some embodiments, the central region is complementary or hybridizes to a viral target RNA sequence that comprises, consists of, or consists essentially of 5 to 15, 5 to 14, 5 to 13, 5 to 12, 5 to 11, 5 to 10, 5 to 9, 5 to 8, 6 to 15, 6 to 14, 6 to 13, 6 to 12, 6 to 11, 6 to 10, 7 to 15, 7 to 14, 7 to 13, 7 to 12, or 7 to 11 contiguous nucleotides within positions 100-800 or 1050-1700 of SEQ ID NO: 1. In some embodiments, the central region is complementary or hybridizes to a viral target RNA sequence that comprises, consists of, or consists essentially of at least 5, 6, 7, 8, 9, 10, 11, 12, 13, 14, or 15 contiguous nucleotides within positions 180-280, 300 to 450, 650 to 775, 1125 to 1300, or 1400 to 1650 of SEQ ID NO: 1. In some embodiments, the central region is complementary or hybridizes to a viral target RNA sequence that comprises, consists of, or consists essentially of at least 5, 6, 7, 8, 9, 10, 11, 12, 13, 14, or 15 contiguous nucleotides within positions 180 to 215, 230 to 270, 350 to 420, 675 to 730, 1165 to 1210, 1245 to 1290, 1400 to 1480, or 1500 to 1630 of SEQ ID NO: 1. In some embodiments, the central region is complementary or hybridizes to a viral target RNA sequence that comprises, consists of, or consists essentially of at least 5, 6, 7, 8, 9, 10, 11, 12, 13, 14, or 15 contiguous starting at position 191, 245, 246, 276, 376, 377, 381, 383, 694, 700, 1182, 1261, 1262, 1408, 1410, 1426, 1431, 1432, 1433, 1435, 1438, 1441, 1443, 1513, 1516, 1517, 1518, 1519, 1520, 1521, 1522, 1527, 1559, 1575, 1576, 1577, 1580, 1581, 1582, or 1589 of SEQ ID NO: 1. In some embodiments, the central region is perfectly complementary to the viral target RNA sequence. In some embodiments, there is less than or equal to 5, 4, 3, 2, or 1 mismatches between the central region and the viral target sequence. In some embodiments, there is less than or equal to 2 mismatches between the central region and the viral target sequence. In some embodiments, there is less than or equal to 1 mismatch between the central region and the viral target sequence.

The following specific sequences in Table 1 are within the scope of the present disclosure. As used herein, ln=Locked nucleic acid (LNA); lnA=Locked nucleic acid (LNA) A; ln(5m)C=Locked nucleic acid (LNA)-5methyl C; lnG=Locked nucleic acid (LNA) G; lnT=Locked nucleic acid (LNA) T; (5m)C=5 methylC; mA=2-O-methoxy A; mU=2-O-methoxy U; (8nh)A=8-amino A; (8nh)G=8-amino G; (2s)T=2-thio T; (5-OH)C=5-hydroxy C; cp=scp=cyclopropyl; cpC=scpC=cyclopropyl C; cpG=scpG=cyclopropyl G; cpT=scpT=cyclopropyl T; ps=phosphorothioate linkages. The "Position in HBV Genome" describes the 5'-end of target-site in acc. KC315400.1 (genotype B).

TABLE 1

Exemplary ASOs

| SEQ ID NO. | ASO # | Position in HBV Genome_Length_Gapmer Structure | Sequences [5' to 3'] |
|---|---|---|---|
| 2 | 1 | 1527_16mer_3-10-3 | 5' ln(5m)CpslnGpsln(5m)CpsGpsTpsApsApsApsGpsApsGpsApsGpslnGpslnTpslnG 3' |
| 3 | 2 | 1559_15mer_4-8-3 | 5' ln(5m)Cpsln(5m)CpslnGpslnGps(5m)CpsApsGpsApsTpsGpsApsGpslnApslnApslnG 3' |

TABLE 1-continued

Exemplary ASOs

| SEQ ID NO. | ASO # | Position in HBV Genome_Length_Gapmer Structure | Sequences [5' to 3'] |
|---|---|---|---|
| 4 | 3 | 1576_16mer_4-8-4 | 5'lnApslnApslnGpsln(5m)CpsGpsApsApsGpsTpsGps(5m)CpsApsln(5m)CpslnApsln(5m)CpslnG 3' |
| 5 | 4 | 1432_17mer_4-10-3 | 5'lnGpslnGpslnApslnTps(5m)CpsApsGps(5m)CpsGps(5m)Cps(5m)CpsGpsApsln(5m)CpslnGpslnG 3' |
| 6 | 5 | 1582_16mer_3-10-3 | 5'lnGpslnApslnGpsGpsTpsGpsApsApsGps(5m)CpsGpsApsApslnGpslnTpslnG 3' |
| 7 | 6 | 1522_15mer_3-8-4 | 5'lnApslnApslnGpsApsGpsApsGpsGpsTpsGps(5m)CpslnGpsln(5m)Cpsln(5m)Cpsln(5m)C 3' |
| 8 | 7 | 1432_16mer_4-9-3 | 5'lnGpslnApslnTpslnTps(5m)CpsApsGps(5m)CpsGps(5m)Cps(5m)CpsGpsApsln(5m)CpslnGpslnG 3' |
| 9 | 8 | 1527_17mer_4-10-3 | 5'ln(5m)Cpsln(5m)CpslnGpsln(5m)CpsGpsTpsApsApsApsGpsApsGpsApsGpslnGpslnTpslnG 3' |
| 10 | 9 | 1431_17mer_3-10-4 | 5'lnGpslnApslnTpsTps(5m)CpsApsGps(5m)CpsGps(5m)Cps(5m)CpsGpsApsln(5m)CpslnGpslnGpslnG 3' |
| 11 | 10 | 1580_15mer_3-9-3 | 5'lnGpslnTpslnGpsApsApsGps(5m)CpsGpsApsApsGpsTpslnGpsln(5m)CpslnA 3' |
| 12 | 11 | 1589_15mer_2-10-3 | 5'ln(5m)CpsGpslnTpsGps(5m)CpsApsGpsApsGpsGpsTpsGpslnApslnApslnG 3' |
| 13 | 12 | 1435_15mer_3-8-4 | 5'lnGpslnGpslnGpsApsTpsTps(5m)CpsApsGps(5m)CpsGpsln(5m)Cpsln(5m)CpslnGpslnA 3' |
| 14 | 13 | 1432_17mer_4-8-5 | 5'lnGpslnGpslnApslnTpsTps(5m)CpsApsGps(5m)CpsGps(5m)Cps(5m)CpslnGpslnApsln(5m)CpslnGpslnG 3' |
| 15 | 14 | 1431_15mer_3-9-3 | 5'lnTpslnTpsln(5m)CpsApsGps(5m)CpsGps(5m)Cps(5m)CpsGpsAps(5m)CpslnGpslnG 3' |
| 16 | 15 | 1432_17mer_4-9-4 | 5'lnGpslnGpslnApslnTpsTps(5m)CpsApsGps(5m)CpsGps(5m)Cps(5m)CpsGpslnApsln(5m)CpslnGpslnG 3' |
| 17 | 16 | 1527_16mer_3-9-4 | 5'ln(5m)CpslnGpsln(5m)CpsGpsTpsApsApsApsGpsApsGpsApslnGpslnGpslnTpslnG 3' |
| 18 | 17 | 1513_15mer_3-9-3 | 5'lnGpsln(5m)CpslnGps(5m)Cps(5m)Cps(5m)Cps(5m)CpsGpsTpsGpsGpsTpsln(5m)CpslnGpslnG 3' |
| 19 | 18 | 245_17mer_4-10-3 | 5'ln(5m)CpslnApsln(5m)Cpsln(5m)CpsAps(5m)CpsGpsApsGpsTps(5m)CpsTpsApsGpslnAps(5m)CpslnT 3' |
| 20 | 19 | 1426_15mer_3-8-4 | 5'ln(5m)CpslnGps(5m)CpsGpsAps(5m)CpsGpsGpsGpsApsln(5m)CpslnGpslnTpslnA 3' |
| 21 | 20 | 377_17mer_4-8-5 | 5'lnApslnApslnApsln(5m)CpsGps(5m)Cps(5m)CpsGps(5m)CpsApsGpsApsln(5m)CpslnApsln(5m)CpslnApslnT 3' |
| 22 | 21 | 1516_15mer_3-10-2 | 5'lnGpslnGpslnTpsGps(5m)CpsGps(5m)Cps(5m)Cps(5m)Cps(5m)CpsGpsTpsGpslnGpslnT 3' |
| 23 | 22 | 1575_16mer_3-10-3 | 5'lnApslnGpsln(5m)CpsGpsApsApsGpsTpsGps(5m)CpsAps(5m)CpsApsln(5m)CpslnGpslnG 3' |
| 24 | 23 | 1580_16mer_3-9-4 | 5'lnGpslnGpslnTpsGpsApsApsGps(5m)CpsGpsApsApsGpslnTpslnGpsln(5m)CpslnA 3' |
| 25 | 24 | 1261_15mer_3-8-4 | 5'ln(5m)CpslnGpsln(5m)CpsApsGpsTpsApsTpsGpsGpsApslnTpsln(5m)CpslnGpslnG 3' |
| 26 | 25 | 1519_16mer_3-10-3 | 5'lnGpslnApslnGpsApsGpsGpsTpsGps(5m)CpsGps(5m)Cps(5m)Cps(5m)Cpsln(5m)CpslnGpslnT 3' |
| 27 | 26 | 1433_17mer_5-8-4 | 5'lnGpslnGpslnGpslnApslnTpsTps(5m)CpsApsGps(5m)CpsGps(5m)Cps(5m)CpslnGpslnApsln(5m)CpslnG 3' |

TABLE 1-continued

Exemplary ASOs

| SEQ ID NO. | ASO # | Position in HBV Genome_ Length_Gapmer Structure | Sequences [5' to 3'] |
|---|---|---|---|
| 28 | 27 | 1433_15mer_ 3-8-4 | 5'lnGpslnApslnTpsTps(5m)CpsApsGps(5m)CpsGps(5m)Cps(5m)Cps lnGpslnAps(5m)CpslnG 3' |
| 29 | 28 | 1431_17mer_ 4-10-3 | 5'lnGpslnApslnTpslnTps(5m)CpsApsGps(5m)CpsGps(5m)Cps(5m) CpsGpsAps(5m)CpslnGpslnGpslnG 3' |
| 30 | 29 | 1518_16mer_ 3-10-3 | 5'lnApslnGpslnApsGpsGpsTpsGps(5m)CpsGps(5m)Cps(5m)Cps(5m) Cps(5m)CpslnGpslnTpslnG 3' |
| 31 | 30 | 1431_17mer_ 4-9-4 | 5'lnGpslnApslnTpslnTps(5m)CpsApsGps(5m)CpsGps(5m)Cps(5m) CpsGpsApsln(5m)CpslnGpslnGpslnG 3' |
| 32 | 31 | 1520_15mer_ 3-8-4 | 5'lnGpslnApslnGpsApsGpsGpsTpsGps(5m)CpsGps(5m)Cpsln(5m) Cpsln(5m)Cpsln(5m)CpslnG 3' |
| 33 | 32 | 1519_17mer_ 3-10-4 | 5'lnApslnGpslnApsGpsApsGpsGpsTpsGps(5m)CpsGps(5m)Cps(5m) Cpsln(5m)Cpsln(5m)CpslnGpslnT 3' |
| 34 | 33 | 1581_16mer_ 3-10-3 | 5'lnApslnGpslnGpsTpsGpsApsApsGps(5m)CpsGpsApsApsGpslnTps lnGpsln(5m)C 3' |
| 35 | 34 | 1575_15mer_ 3-10-2 | 5'lnGpsln(5m)CpslnGpsApsApsGpsTpsGps(5m)CpsAps(5m)CpsAps (5m)CpslnGpslnG 3' |
| 36 | 35 | 1438_15mer_ 3-9-3 | 5'ln(5m)CpslnGps(5m)CpsGpsGpsGpsApsTpsTps(5m)CpsApsGpsln (5m)CpslnGpsln(5m)C 3' |
| 37 | 36 | 1520_15mer_ 3-10-2 | 5'lnGpslnApslnGpsApsGpsGpsTpsGps(5m)CpsGps(5m)Cps(5m)Cps (5m)Cpsln(5m)CpslnG3' |
| 38 | 37 | 1520_17mer_ 4-10-3 | 5'lnApslnApslnGpslnApsGpsApsGpsGpsTpsGps(5m)CpsGps(5m) Cps(5m)Cpsln(5m)Cpsln(5m)CpslnG 3' |
| 39 | 38 | 1517_15mer_ 3-9-3 | 5'lnApslnGpslnGpsTpsGps(5m)CpsGps(5m)Cps(5m)Cps(5m)Cps(5m) CpsGpslnTpslnGpslnG 3' |
| 40 | 39 | 1262_15mer_ 3-8-4 | 5'ln(5m)Cpsln(5m)CpslnGps(5m)CpsApsGpsTpsApsTpsGpsGpslnAps lnTpsln(5m)CpslnG 3' |
| 41 | 40 | 246_17mer_ 3-10-4 | 5'ln(5m)Cpsln(5m)CpslnAps(5m)Cps(5m)CpsAps(5m)CpsGpsAps GpsTps(5m)CpsTpslnApslnGpslnApsln(5m)C 3' |
| 42 | 41 | 191_16mer_ 3-9-4 | 5'ln(5m)Cpsln(5m)CpslnGps(5m)Cps(5m)CpsTpsGpsTpsApsAps(5m) CpsApsln(5m)CpslnGpslnApslnG 3' |
| 43 | 42 | 1441_15mer_ 3-8-4 | 5'lnGpslnTpsln(5m)Cps(5m)CpsGps(5m)CpsGpsGpsGpsApsTpslnTps ln(5m)CpslnApslnG 3' |
| 44 | 43 | 1443_17mer_ 3-10-4 | 5'lnGpslnGpslnTps(5m)CpsGpsTps(5m)Cps(5m)CpsGps(5m)CpsGps GpsGpslnApslnTpslnTpsln(5m)C 3 |
| 45 | 44 | 1408_17mer_ 4-10-3 | 5'lnApsln(5m)CpslnApslnApsApsGpsGpsAps(5m)CpsGpsTps(5m) Cps(5m)Cps(5m)CpslnGpsln(5m)CpslnG 3' |
| 46 | 45 | 1433_16mer_ 4-9-3 | 5'lnGpslnGpslnApslnTpsTps(5m)CpsApsGps(5m)CpsGps(5m)Cps(5m) CpsGpslnApsln(5m)CpslnG 3' |
| 47 | 46 | 1432_17mer_ 3-10-4 | 5'lnGpslnGpslnApsTpsTps(5m)CpsApsGps(5m)CpsGps(5m)Cps(5m) CpsGpslnApsln(5m)CpslnGpslnG 3' |
| 48 | 47 | 1433_16mer_ 3-10-3 | 5'lnGpslnGpslnApslnTpsTps(5m)CpsApsGps(5m)CpsGps(5m)Cps(5m) CpsGpslnApsln(5m)CpslnG 3' |
| 49 | 48 | 246_17mer_ 4-10-3 | 5'ln(5m)Cpsln(5m)CpslnApsln(5m)Cps(5m)CpsAps(5m)CpsGpsAps GpsTps(5m)CpsTpsApslnGpslnApsln(5m)C 3' |
| 50 | 49 | 1575_16mer_ 4-9-3 | 5'lnApslnGpsln(5m)CpslnGpsApsApsGpsTpsGps(5m)CpsAps(5m) CpsApsln(5m)CpslnGpslnG 3' |
| 51 | 50 | 1576_15mer_ 4-8-3 | 5'lnApslnGpsln(5m)CpslnGpsApsApsGpsTpsGps(5m)CpsAps(5m) CpslnApsln(5m)CpslnG 3' |

TABLE 1-continued

Exemplary ASOs

| SEQ ID NO. | ASO # | Position in HBV Genome_Length_Gapmer Structure | Sequences [5' to 3'] |
|---|---|---|---|
| 52 | 51 | 1580_16mer_3-10-3 | 5'lnGpslnGpslnTpsGpsApsApsGps(5m)CpsGpsApsApsGpsTpslnGpsln(5m)CpslnA 3' |
| 53 | 52 | 1576_15mer_3-10-2 | 5'lnApslnGpsln(5m)CpsGpsApsApsGpsTpsGps(5m)CpsAps(5m)CpsApsln(5m)CpslnG 3 |
| 54 | 53 | 191_16mer_4-8-4 | 5'ln(5m)Cpsln(5m)CpslnGpsln(5m)Cps(5m)CpsTpsGpsTpsApsAps(5m)CpsApsln(5m)CpslnGpslnApslnG 3' |
| 55 | 54 | 1435_15mer_3-9-3 | 5'lnGpslnGpslnGpsApsTpsTps(5m)CpsApsGps(5m)CpsGps(5m)Cpsln(5m)CpslnGpslnA 3' |
| 56 | 55 | 1518_15mer_3-9-3 | 5'lnGpslnApslnGpsGpsTpsGps(5m)CpsGps(5m)Cps(5m)Cps(5m)Cps(5m)CpslnGpslnTpslnG 3' |
| 57 | 56 | 1581_16mer_4-9-3 | 5'lnApslnGpslnGpslnTpsGpsApsApsGps(5m)CpsGpsApsApsGpslnTpslnGpsln(5m)C 3' |
| 58 | 57 | 694_17mer_4-9-4 | 5'lnGpsln(5m)Cpsln(5m)Cpsln(5m)CpsTpsAps(5m)CpsGpsApsAps(5m)Cps(5m)CpsApsln(5m)CpslnTpslnGpslnA 3' |
| 59 | 58 | 377_15mer_4-8-3 | 5'lnApsln(5m)CpslnGpsln(5m)Cps(5m)Cps(5m)CpsApsGpsAps(5m)CpsApsln(5m)CpsApslnT 3' |
| 60 | 59 | 383_17mer_4-10-3 | 5'lnApslnTpslnGpslnApsTpsApsApsApsAps(5m)CpsGps(5m)Cps(5m)CpsGpsln(5m)CpslnApslnG 3' |
| 61 | 60 | 1432_15mer_4-8-3 | 5'lnApslnTpslnTpsln(5m)CpsApsGps(5m)CpsGps(5m)Cps(5m)CpsGpsApsln(5m)CpslnGpslnG 3' |
| 62 | 61 | 1408_15mer_2-10-3 | 5'lnApslnApsApsGpsGpsAps(5m)CpsGpsTps(5m)Cps(5m)Cps(5m)CpslnGpsln(5m)CpslnG 3' |
| 63 | 62 | 1522_15mer_3-9-3 | 5'lnApslnApslnGpsApsGpsApsGpsGpsTpsGps(5m)CpsGpsln(5m)Cpsln(5m)Cpsln(5m)Cps 3' |
| 64 | 63 | 1432_15mer_3-8-4 | 5'lnApslnTpslnTps(5m)CpsApsGps(5m)CpsGps(5m)Cps(5m)CpsGpslnApsln(5m)CpslnGpslnG 3 |
| 65 | 64 | 383_17mer_4-8-5 | 5'lnApslnTpslnGpslnApsTpsApsApsApsAps(5m)CpsGps(5m)Cpsln(5m)CpslnGpsln(5m)CpslnApslnG 3' |
| 66 | 65 | 1410_15mer_4-8-3 | 5'lnApsln(5m)CpslnApslnApsApsGpsGpsAps(5m)CpsGpsTps(5m)Cpsln(5m)Cpsln(5m)CpslnG 3' |
| 67 | 66 | 1581_15mer_3-10-2 | 5'lnGpslnGpslnTpsGpsApsApsGps(5m)CpsGpsApsApsGpsTpslnGpsln(5m)C 3' |
| 68 | 67 | 376_17mer_4-10-3 | 5'lnApslnApsln(5m)CpslnGps(5m)Cps(5m)CpsGps(5m)CpsApsGpsAps(5m)CpsAps(5m)CpslnApslnTpsln(5m)C 3' |
| 69 | 68 | 377_17mer_4-9-4 | 5'lnApslnApslnApsln(5m)CpsGps(5m)Cps(5m)CpsGps(5m)CpsApsGpsAps(5m)CpslnApsln(5m)CpslnApslnT 3' |
| 70 | 69 | 377_15mer_3-8-4 | 5'lnApsln(5m)CpslnGps(5m)Cps(5m)CpsGps(5m)CpsApsGpsAps(5m)CpslnApsln(5m)CpslnApslnT 3' |
| 71 | 70 | 1582_15mer_3-10-2 | 5'lnApslnGpslnGpsTpsGpsApsApsGps(5m)CpsGpsApsApsGpslnTpslnG 3' |
| 72 | 71 | 377_16mer_3-10-3 | 5'lnApslnApsln(5m)CpsGps(5m)Cps(5m)CpsGps(5m)CpsApsGpsAps(5m)CpsApsln(5m)CpslnApslnT 3' |
| 73 | 72 | 1576_16mer_4-9-3 | 5'lnApslnApslnGpsln(5m)CpsGpsApsApsGpsTpsGps(5m)CpsAps(5m)CpslnApsln(5m)CpslnG 3' |
| 74 | 73 | 381_17mer_5-8-4 | 5'lnGpslnApslnTpslnApsln(5m)ApsApsAps(5m)CpsGps(5m)Cps(5m)CpsGps(5m)CpslnApslnGpslnApsln(5m)C 3' |
| 75 | 74 | 1580_16mer_4-9-3 | 5'lnGpslnGpslnTpslnGpsApsApsGps(5m)CpsGpsApsApsGpsTpslnGpsln(5m)CpslnA 3' |

TABLE 1-continued

Exemplary ASOs

| SEQ ID NO. | ASO # | Position in HBV Genome_ Length_Gapmer Structure | Sequences [5' to 3'] |
|---|---|---|---|
| 76 | 75 | 694_17mer_ 3-10-4 | 5'lnGpsln(5m)Cpsln(5m)Cps(5m)CpsTpsAps(5m)CpsGpsApsAps (5m)Cps(5m)CpsApsln(5m)ClnTpslnGpslnA 3' |
| 77 | 76 | 1261_15mer_ 3-10-2 | 5'ln(5m)CpslnGpsln(5m)CpsApsGpsTpsApsTpsGpsGpsApsTps(5m) CpslnGpslnG 3' |
| 78 | 77 | 1518_15mer_ 3-10-2 | 5'lnGpslnApslnGpsGpsTpsGps(5m)CpsGps(5m)Cps(5m)Cps(5m)Cps (5m)CpsGpslnTpslnG 3' |
| 79 | 78 | 383_17mer_ 4-9-4 | 5'lnApslnTpslnGpslnApsTpsApsApsApsAps(5m)CpsGps(5m)Cps (5m)CpslnGpsln(5m)CpslnApslnG 3' |
| 80 | 79 | 383_17mer_ 3-10-4 | 5'lnApslnTpslnGpsApsTpsApsApsApsAps(5m)CpsGps(5m)Cps(5m) CpslnGpsln(5m)CpslnApslnG 3' |
| 81 | 80 | 377_17mer_ 4-10-3 | 5'lnApslnApslnApsln(5m)CpsGps(5m)Cps(5m)CpsGps(5m)CpsAps GpsAps(5m)CpsApsln(5m)CpslnApslnT 3' |
| 82 | 81 | 1521_16mer_ 4-9-3 | 5'lnApslnApslnGpslnApsGpsApsGpsGpsTpsGps(5m)CpsGps(5m) Cpsln(5m)Cpsln(5m)Cpsln(5m)C 3' |
| 83 | 82 | 1577_15mer_ 3-10-2 | 5'lnApslnApslnGps(5m)CpsGpsApsApsGpsTpsGps(5m)CpsAps(5m) CpslnApsln(5m)C 3' |
| 84 | 83 | 1182_15mer_ 3-8-4 | 5'lnGpslnTpslnTpsGps(5m)CpsGpsTps(5m)CpsApsGps(5m)CpslnAps lnApslnApsln(5m)C 3' |
| 85 | 84 | 700_17mer_ 3-10-4 | 5'lnGpslnGpslnGpsApsApsApsGps(5m)Cps(5m)Cps(5m)CpsTpsAps (5m)CpslnGpslnApslnApsln(5m)C 3' |
| 86 | 85 | 383_17mer_ 5-8-4 | 5'lnApslnTpslnGpslnApslnTpsApsApsApsAps(5m)CpsGps(5m)Cps (5m)CpslnGpsln(5m)CpslnApslnG 3' |
| 87 | 86 | 1576_16mer_ 4-8-4 | 5'lnApslnApslnGps(5m)AmCpsGpsApsApsGpsTpsGps(5m)CpsAps ln(5m)CpslnApsln(5m)CpslnG 3' |
| 88 | 87 | 1576_16mer_ 4-8-4 | 5'lnApslnApslnGpsln(5m)CpsGpsApsApsGpsTpsGps(5m)CpsApsln (5m)CpsAmApsln(5m)CpslnG 3' |
| 89 | 88 | 1576_16mer_ 4-8-4 | 5'lnApslnApslnGpsln(5m)CpsGpsApsApsGpsTpsGps(5m)CpsAps (5m)AmCpslnApsln(5m)CpslnG 3' |
| 90 | 89 | 1575_16mer_ 3-10-3 | 5'ScpApslnGpsln(5m)CpsGpsApsApsGpsTpsGps(5m)CpsAps(5m) CpsApsln(5m)CpslnGpslnG 3' |
| 91 | 90 | 1575_16mer_ 3-10-3 | 5'lnApslnGpsln(5m)CpsGpsApsApsGpsTpsGps(5m)CpsAps(5m) CpsApsln(5m)CpslnGpsscpG 3' |
| 92 | 91 | 383_17mer_ 4-8-5 | 5'ScpApslnTpslnGpslnApsTpsApsApsApsAps(5m)CpsGps(5m)Cps Gpsln(5m)CpslnGpsln(5m)CpslnApslnG 3' |
| 93 | 92 | 383_17mer_ 4-8-5 | 5'lnApslnTpslnGpslnApsTpsApsApsApsAps(5m)CpsGps(5m)Cps Gpsln(5m)CpslnGpsln(5m)CpslnApsScpG 3' |
| 94 | 93 | 383_17mer_ 4-8-5 | 5'lnApsScpTpslnGpslnApsTpsApsApsApsAps(5m)CpsGps(5m)Cpsln (5m)CpslnGpsln(5m)CpslnApslnG 3' |
| 95 | 94 | 1527_16mer_ 3-10-3 | 5'ln(5m)CpslnGpsln(5m)CpsGpsTpsApsApsApsGpsApsGpsApsAps lnGpsScpTpslnG 3' |
| 96 | 9A | 1431_17mer_ 3-10-4 | 5'lnGpslnApsscpTpsTps(5m)Cps(8nh)ApsGps(5m)CpsGps(5m)Cps (5m)CpsGpsApsln(5m)CpslnGpslnGpslnG 3' |
| 97 | 9B | 1431_17mer_ 3-10-4 | 5'mU-lnGpslnApsscpTpsTps(5m)Cps(8nh)ApsGps(5m)CpsGps(5m) Cps(5m)CpsGpsApsln(5m)CpslnGpslnGpslnG 3' |
| 98 | 9C | 1431_17mer_ 3-10-4 | 5'mU-lnGpslnApslnTpsTps(5m)CpsApsGps(5m)CpsGps(5m)Cps(5m)Cps GpsApsln(5m)CpslnGpslnGpslnG 3' |
| 99 | 25A | 1519_16mer_ 3-10-3 | 5'lnGpslnApslnGpsApsGpsGpsTpsGps(5m)CpsGps(5m)Cps(5m)Cps (5m)Cpsln(5m)CpslnGpslnT 3' |

TABLE 1-continued

Exemplary ASOs

| SEQ ID NO. | ASO # | Position in HBV Genome_Length_Gapmer Structure | Sequences [5' to 3'] |
|---|---|---|---|
| 100 | 25B | 1519_16mer_3-10-3 | 5'lnGpslnApslnGpsApsGpsGpsTpsGps(5m)CpsGps(5m)Cps(5m)Cps(5m)Cpsln(5m)CpslnGpsAmT 3' |
| 101 | 25C | 1519_16mer_3-10-3 | 5'lnGpslnApslnGpsApsGpsGpsTpsGps(5m)CpsGps(5m)Cps(5m)Cps(5m)CpsAm(5m)CpslnGpslnT 3' |
| 102 | 25D | 1519_16mer_3-10-3 | 5'lnGpslnApslnGpsApsGpsGpsTpsGps(5m)CpsGps(5m)Cps(5m)Cps(5m)Cpsln(5m)CpslnGpsscpT 3' |
| 103 | 25E | 1519_16mer_3-10-3 | 5'lnGpslnApslnGpsApsGpsGpsTpsGps(5m)CpsGps(5m)Cps(5m)Cps(5m)Cps(5m)scpCpslnGpslnT 3' |
| 104 | 25F | 1519_16mer_3-10-3 | 5'mU-lnGpslnApslnGpsApsGpsGpsTpsGps(5m)CpsGps(5m)Cps(5m)Cps(5m)Cpsln(5m)CpslnGpslnT 3' |
| 105 | 25G | 1519_16mer_3-10-3 | 5'mU-lnGpslnApslnGpsApsGpsAps(8nh)GpsGpsTpsGps(5m)CpsGps(5m)Cps(5m)Cps(5m)Cpsscp(5m)CpslnGpslnT 3' |
| 106 | 47A | 1433_16mer_3-10-3 | 5'lnGpslnGpslnAps(2s)TpsTps(5m)CpsApsGps(5m)CpsGps(5m)Cps(5m)CpsGpslnApsln(5m)CpslnG 3' |
| 107 | 47B | 1433_16mer_3-10-3 | 5'lnGpslnGpslnApsTps(2s)Tps(5m)CpsApsGps(5m)CpsGps(5m)Cps(5m)CpsGpslnApsln(5m)CpslnG 3' |
| 108 | 47C | 1433_16mer_3-10-3 | 5'lnGpslnGpslnApsTpsTps(5oh)CpsApsGps(5m)CpsGps(5m)Cps(5m)CpsGpslnApsln(5m)CpslnG 3' |
| 109 | 47D | 1433_16mer_3-10-3 | 5'mU-lnGpslnGpslnApsTps(2s)Tps(5m)CpsApsGps(5m)CpsGps(5m)Cps(5m)CpsGpslnApsln(5m)CpslnG 3' |
| 110 | 47E | 1433_16mer_3-10-3 | 5'mU-lnGpslnGpslnApsTps(2s)Tps(5m)CpsApsGps(5m)CpsGps(5m)Cps(5m)CpsGpslnApsscp(5m)CpslnG 3' |
| 111 | 47F | 1433_16mer_3-10-3 | 5mU-lnGpslnGpslnApsTpsTps(5m)CpsApsGps(5m)CpsGps(5m)Cps(5m)CpsGpslnApsln(5m)CpslnG 3' |
| 112 | 73A | 381_17mer_5-8-4 | 5'lnGpslnApslnTpslnApslnApsApsAps(5m)CpsGps(5m)Cps(5m)CpsGps(5m)CpslnApslnGpslnApsscp(5m)C 3' |
| 113 | 73B | 381_17mer_5-8-4 | 5'mA-lnGpslnApslnTpslnApslnApsApsAps(5m)CpsGps(5m)Cps(5m)CpsGps(5m)CpslnApslnGpslnApsscp(5m)C 3' |
| 114 | 73C | 381_17mer_5-8-4 | 5'mA-lnGpslnApslnTpslnApslnAps(8nh)ApsAps(5m)CpsGps(5m)Cps(5m)CpsGps(5m)CpslnApslnGpslnApsscp(5m)C 3' |
| 115 | 34A | 1575_15mer_3-10-2 | 5'mU-lnGpln(5m)CpsscpGpsAps(8nh)ApsGpsTpsGps(5m)CpsAps(5m)CpsAps(5m)CpslnGpslnG 3' |
| 116 | 40A | 246_17mer_3-10-4 | 5'mA-ln(5m)Cpsscp(5m)CpslnApsln(5m)Cps(5m)CpsAps(5m)CpsGpsApsGpsTps(5m)CpsTpsApslnGpslnApsln(5m)C 3' |
| 117 | 23A | 1580_16mer_3-9-4 | 5'mU-lnGpslnGpsscpTpsGpsApsApsGps(5m)CpsGpsApsApsGpslnTpslnGpsln(5m)CpslnA 3' |

In some embodiments, the ASO comprises a nucleotide sequence that is at least 90% identical to a nucleotide sequence selected from the sequences listed in Table 1, 2A, 3, 4, 7, 8, 9, 10, 11, 13, 14, or 19. In some embodiments, the ASO is ASO 120 or ASO 121.

In some embodiments, the ASOs of the disclosure have a sequence that differs from an ASO of Table 1, 2A, 3, 4, 7, 8, 9, 10, 11, 13, 14, or 19 by one nucleoside. In other embodiments, the ASO has a sequence that differs from an ASO of Table 1, 2A, 3, 4, 7, 8, 9, 10, 11, 13, 14, or 19 by 1, 2, 3 or 4 nucleosides. In some embodiments, the nucleotide sequence is at least 90% identical to a nucleotide sequence selected from Table 1, 2A, 3, 4, 7, 8, 9, 10, 11, 13, 14, or 19. In some embodiments, the ASOs of the disclosure have a sequence of Table 1, 2A, 3, 4, 7, 8, 9, 10, 11, 13, 14, or 19, but one T in the central region is replaced by (2s)T, one C in the central region is replaced by (5OH)C, and/or one A is replaced by (8NH)A in the central region. In some embodiments, the ASOs of the disclosure have a sequence of Table 1, 2A, 3, 4, 7, 8, 9, 10, 11, 13, 14, or 19, but with one or two ScpBNA, AmNA, or GuNA in the 5' wing portion. In some embodiments, the ASOs of the disclosure have a sequence of Table 1, 2A, 3, 4, 7, 8, 9, 10, 11, 13, 14, or 19, but with one or two ScpBNA, AmNA, or GuNA in the 3' wing portion. In some embodiments, the ASOs of the disclosure have a sequence of Table 1, 2A, 3, 4, 7, 8, 9, 10, 11, 13, 14, or 19, but with a mA or mU appended to the 5' end of the sequence. In some embodiments, the ASOs of the disclosure have a sequence of Table 1, 2A, 3, 4, 7, 8, 9, 10, 11, 13, 14, or 19, but with a mA or mU appended to the 5' end of the sequence that links to a GalNAc derivative (e.g., GalNAc4, such as GalNAc4-(PS)2-p-, or GalNAc6, such as GalNAc6-(PS)2-p-), as detailed herein.

In some embodiments, the ASO comprises a nucleotide sequence that is at least 90% identical to a nucleotide sequence of any one of SEQ ID NOs: 2-428. In some embodiments, the ASO comprises the nucleotide sequence of SEQ ID NO: 400 or 404.

In some embodiments, the ASOs of the disclosure have a sequence that differs from any of the nucleotides of SEQ ID NOs: 2-428 by one nucleoside. In other embodiments, the ASO has a sequence that differs from any of the nucleotides of SEQ ID NOs: 2-428 by 1, 2, 3 or 4 nucleosides. In some embodiments, the nucleotide sequence is at least 90% identical to a nucleotide sequence of any one of SEQ ID NOs: 2-428. In some embodiments, the ASOs of the disclosure have a sequence of any one of SEQ ID NOs: 2-428, but one T in the central region is replaced by (2s)T, one C in the central region is replaced by (5OH)C, and/or one A is replaced by (8NH)A in the central region. In some embodiments, the ASOs of the disclosure have a sequence of any one of SEQ ID NOs: 2-428, but with one or two ScpBNA, AmNA, or GuNA in the 5' wing portion. In some embodiments, the ASOs of the disclosure have a sequence of any one of SEQ ID NOs: 2-428, but with one or two ScpBNA, AmNA, or GuNA in the 3' wing portion. In some embodiments, the ASOs of the disclosure have a sequence of any one of SEQ ID NOs: 2-428, but with a mA or mU appended to the 5' end of the sequence. In some embodiments, the ASOs of the disclosure have a sequence of any one of SEQ ID NOs: 2-428, but with a mA or mU appended to the 5' end of the sequence that links to a GalNAc derivative (e.g., GalNAc4, such as GalNAc4-(PS)2-p-, or GalNAc6, such as GalNAc6-(PS)2-p-), as detailed herein.

The present disclosure is also directed to additional components conjugated to the ASO such as targeting moieties and oligonucleotides modified at one or more end.

In some embodiments, the targeting moiety may comprise a carbohydrate, such as a monosaccharide, for example N-acetylgalactosamine (GalNAc), di saccharides, trisaccharides, tetrasaccharides, oligosaccharides, and polysaccharides. In certain embodiments, the targeting moiety one or more GalNAc derivatives, such as two or three GalNAc derivatives attached to the ASO through one or more linkers, optionally in a consecutive structure. In certain embodiments, the targeting moiety comprises three consecutive GalNAc moieties attached through linkers, such as:

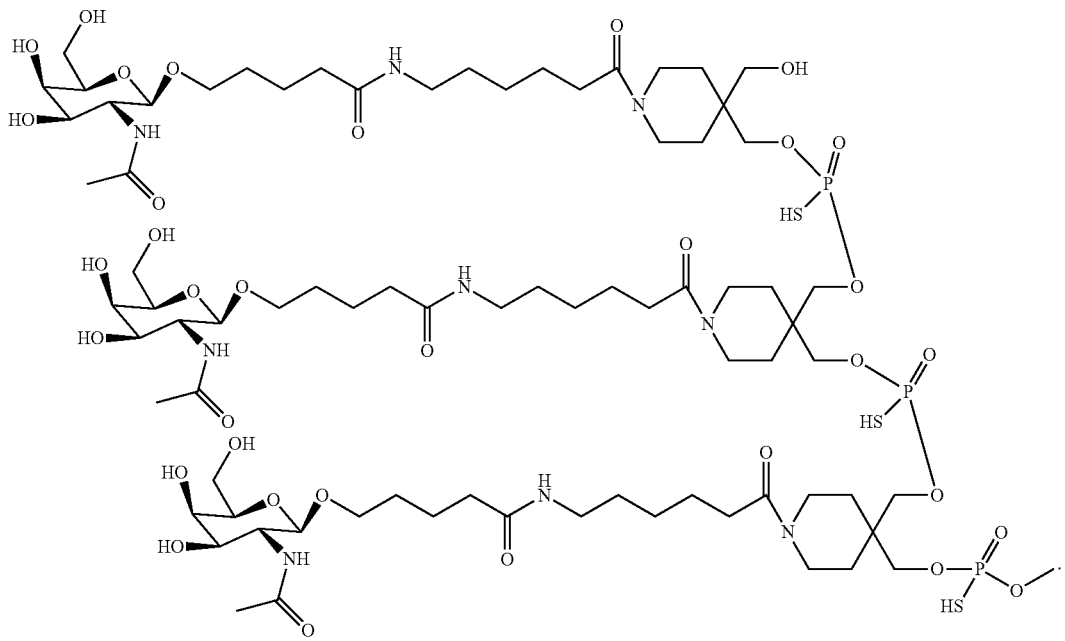

In some embodiments, the ASO contains a targeting moiety at the 5'-end, the 3'-end, or both ends of the ASO.

In certain embodiments, the ASO is modified at one or more end by a vinyl phosphonate moiety, such as a 5'-vinyl phosphonate moiety.

Compositions

The present disclosure also encompasses pharmaceutical compositions comprising ASOs of the present disclosure. One embodiment is a pharmaceutical composition comprising one or more ASO of the present disclosure, and a pharmaceutically acceptable diluent or carrier.

In some embodiments, the pharmaceutical composition containing the ASO of the present disclosure is formulated for systemic administration via parenteral delivery. Parenteral administration includes intravenous, intra-arterial, subcutaneous, intraperitoneal or intramuscular injection or infusion; also subdermal administration, e.g., via an implanted device. In a preferred embodiment, the pharmaceutical composition containing the ASO of the present disclosure is formulated for subcutaneous (SC) or intravenous (IV) delivery. Formulations for parenteral administration may include sterile aqueous solutions, which may also contain buffers, diluents and other pharmaceutically acceptable additives as understood by the skilled artisan. For intravenous use, the total concentration of solutes may be controlled to render the preparation isotonic.

The pharmaceutical compositions containing the ASO of the present disclosure are useful for treating a disease or disorder, e.g., associated with the expression or activity of an HBV gene.

In some embodiments, the pharmaceutical composition comprises a first ASO of the present disclosure that is complementary or hybridizes to a viral target RNA sequence in a first X region of HBV, and a second ASO of the present disclosure that is complementary or hybridizes to a viral target RNA sequence in a second X region or an S region of HBV, and a pharmaceutically acceptable diluent or carrier. When the pharmaceutical composition comprises two or more ASOs, the ASOs may be present in varying amounts. For example, in some embodiments, the weight ratio of first ASO to second ASO is 1:4 to 4:1, e.g., 1:4, 1:3, 1:2, 1:1, 2:1, 3:1, or 4:1. In some embodiments, the molar ratio of first ASO to second ASO is 1:4 to 4:1, e.g., 1:4, 1:3, 1:2, 1:1, 2:1, 3:1, or 4:1.

Methods of Use

One aspect of the present technology includes methods for treating a subject diagnosed as having, suspected as having, or at risk of having an HBV infection and/or an HBV-associated disorder. In therapeutic applications, compositions comprising one or more ASO of the present technology are administered to a subject suspected of, or already suffering from such a disease (such as, e.g., persistence of HBV cccDNA, presence of an HBV antigen (e.g., HBsAg and/or HBeAg) in the serum and/or liver of the subject, or elevated HBV viral load levels), in an amount sufficient to cure, or at least partially arrest, the symptoms of the disease, including its complications and intermediate pathological phenotypes in development of the disease.

Subjects suffering from an HBV infection and/or an HBV-associated disorder can be identified by any or a combination of diagnostic or prognostic assays known in the art. For example, typical symptoms of HBV infection and/or an HBV-associated disorder include, but are not limited to the presence of liver HBV cccDNA, the presence of serum and/or liver HBV antigen (e.g., HBsAg and/or HBeAg), elevated ALT, elevated AST, the absence or low level of anti-HBV antibodies, liver injury, cirrhosis, delta hepatitis, acute hepatitis B, acute fulminant hepatitis B, chronic hepatitis B, liver fibrosis, end-stage liver disease, hepatocellular carcinoma, serum sickness-like syndrome, anorexia, nausea, vomiting, low-grade fever, myalgia, fatigability, disordered gustatory acuity and smell sensations (aversion to food and cigarettes), right upper quadrant and epigastric pain (intermittent, mild to moderate), hepatic encephalopathy, somnolence, disturbances in sleep pattern, mental confusion, coma, ascites, gastrointestinal bleeding, coagulopathy, jaundice, hepatomegaly (mildly enlarged, soft liver), splenomegaly, palmar erythema, spider nevi, muscle wasting, spider angiomas, vasculitis, variceal bleeding, peripheral edema, gynecomastia, testicular atrophy, abdominal collateral veins (caput medusa), high levels of alanine aminotransferase (ALT) and aspartate aminotransferase (AST) (within a range of 1000-2000 IU/mL), ALT levels higher than AST levels, elevated gamma-glutamyl transpeptidase (GGT) and/or alkaline phosphatase (ALP) levels, decreased albumin levels, elevated serum iron levels, leukopenia (i.e granulocytopenia), lymphocytosis, increased erythrocyte sedimentation rate (ESR), shortened red blood cell survival, hemolysis, thrombocytopenia, a prolongation of the international normalized ratio (INR), the presence of serum HBV DNA, elevation of the aminotransferases (<5 times the ULN), increased bilirubin levels, prolonged prothrombin time (PT), hyperglobulinemia, the presence of tissue-nonspecific antibodies, such as anti-smooth muscle antibodies (ASMAs) or antinuclear antibodies (ANAs), the presence of tissue-specific antibodies, such as antibodies against the thyroid gland, elevated levels of rheumatoid factor (RF), hyperbilirubinemia, low platelet and white blood cell counts, AST levels higher than ALT levels, lobular inflammation accompanied by degenerative and regenerative hepatocellular changes, and predominantly centrilobular necrosis.

In some embodiments, subjects treated with the ASO composition of the present technology will show amelioration or elimination of one or more of the following conditions or symptoms: presence of liver HBV cccDNA, the presence of serum and/or liver HBV antigen (e.g., HBsAg and/or HBeAg), the absence or low level of anti-HBV antibodies, liver injury, cirrhosis, delta hepatitis, acute hepatitis B, acute fulminant hepatitis B, chronic hepatitis B, liver fibrosis, end-stage liver disease, hepatocellular carcinoma, serum sickness-like syndrome, anorexia, nausea, vomiting, low-grade fever, myalgia, fatigability, disordered gustatory acuity and smell sensations (aversion to food and cigarettes), right upper quadrant and epigastric pain (intermittent, mild to moderate), hepatic encephalopathy, somnolence, disturbances in sleep pattern, mental confusion, coma, ascites, gastrointestinal bleeding, coagulopathy, jaundice, hepatomegaly (mildly enlarged, soft liver), splenomegaly, palmar erythema, spider nevi, muscle wasting, spider angiomas, vasculitis, variceal bleeding, peripheral edema, gynecomastia, testicular atrophy, abdominal collateral veins (caput medusa), ALT levels higher than AST levels, leukopenia (i.e granulocytopenia), decreased albumin levels, elevated serum iron levels, lymphocytosis, increased erythrocyte sedimentation rate (ESR), shortened red blood cell survival, hemolysis, thrombocytopenia, a prolongation of the international normalized ratio (INR), the presence of serum HBV DNA, prolonged prothrombin time (PT), hyperglobulinemia, the presence of tissue-nonspecific antibodies, such as anti-smooth muscle antibodies (ASMAs) or antinuclear antibodies (ANAs), the presence of tissue-specific antibodies, such as antibodies against the thyroid gland, hyperbilirubinemia, low platelet and white blood cell counts, AST levels higher than ALT levels, lobular inflammation accompanied by degenerative and regenerative hepatocellular changes, and predominantly centrilobular necrosis.

The present disclosure provides a method for treating a subject diagnosed as having, or suspected as having an HBV infection and/or an HBV-associated disorder comprising administering to the subject an effective amount of an ASO composition of the present technology. In some embodiments, the method comprises administering to the subject a first ASO of the present disclosure and a second ASO of the present disclosure, wherein the first ASO is complementary or hybridizes to a viral target RNA sequence in a first X region of HBV, and the second ASO is complementary or hybridizes to a viral target RNA sequence in a second X region or an S region of HBV. In some embodiments, the second ASO is complementary or hybridizes to the viral target RNA sequence in the second X region of HBV. In other embodiments, the second ASO is complementary or hybridizes to the viral target RNA sequence in the S region of HBV The ASOs of the present disclosure may be used to treat a disease in a subject in need thereof. In some embodiments, a method of treating a disease in a subject in need thereof comprises administering to the subject any of the ASOs disclosed herein. In some embodiments, a method of treating a disease in a subject in need thereof comprises administering to the subject any of the compositions disclosed herein.

Administration of the ASO may be conducted by methods known in the art. In some embodiments, the ASO is administered by subcutaneous (SC) or intravenous (IV) delivery. The preparations (e.g., ASOs or compositions) of the present disclosure may be given orally, parenterally, topically, or rectally. They are of course given in forms suitable for each administration route. For example, they are administered in tablets or capsule form, administration by injection, infusion or inhalation; topical by lotion or ointment; and rectal by suppositories. In some embodiments, subcutaneous administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds (e.g., ASOs) of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound (e.g., ASO) of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds (e.g., ASOs) of the disclosure employed in the pharmaceutical composition at levels lower than that required in order to achieve the desired therapeutic effect and gradually increase the dosage until the desired effect is achieved.

In general, a suitable daily dose of a compound (e.g., ASO) of the disclosure is the amount of the compound that is the lowest dose effective to produce a therapeutic effect. Such an effective dose generally depends upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. In some embodiments, the compound is administered at about 1 mg/kg to about 40 mg/kg, about 1 mg/kg to about 30 mg/kg, about 1 mg/kg to about 20 mg/kg, about 1 mg/kg to about 15 mg/kg, or 1 mg/kg to about 10 mg/kg. In some embodiments, the compound is administered at a dose equal to or greater than 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.35, 0.40, 0.45, 0.50, 0.55, 0.60, 0.65, 0.7, 0.75, 0.8, 0.85, 0.9, 0.95, or 1 mg/kg. In some embodiments, the compound is administered at a dose equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mg/kg. In some embodiments, the compound is administered at a dose equal to or less than 200, 190, 180, 170, 160, 150, 140, 130, 120, 110, 100, 95, 90, 85, 80, 75, 70, 65, 60, 55, 50, 45, 40, 35, 30, 25, 20, or 15 mg/kg. In some embodiments, the total daily dose of the compound is equal to or greater than 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 100 mg.

If desired, the effective daily dose of the active compound (e.g., ASO) may be administered as two, three, four, five, six, seven, eight, nine, ten or more doses or sub-doses administered separately at appropriate intervals throughout the day, optionally, in unit dosage forms. In some embodiments, the compound is administered at least 1, 2, 3, 4, 5, 6, 7, 8, 9, 10, 11, 12, 13, 14, or 15 times. Preferred dosing is one administration per day. In some embodiments, the compound is administered at least 1, 2, 3, 4, 5, 6, 7, 8, 9, 10, 11, 12, 13, 14, 15, 16, 17, 18, 19, 20, or 21 times a week. In some embodiments, the compound is administered at least 1, 2, 3, 4, 5, 6, 7, 8, 9, 10, 11, 12, 13, 14, 15, 16, 17, 18, 19, 20, or 21 times a month. In some embodiments, the compound is administered once every 1, 2, 3, 4, 5, 6, 7, 8, 9, 10, 11, 12, 13, 14, 15, 16, 17, 18, 19, 20, or 21 days. In some embodiments, the compound is administered every 3 days. In some embodiments, the compound is administered once every 1, 2, 3, 4, 5, 6, 7, 8, 9, 10, 11, 12, 13, 14, or 15 weeks. In some embodiments, the compound is administered every month. In some embodiments, the compound is administered once every 1, 2, 3, 4, 5, 6, 7, 8, 9, 10, 11, 12, 13, 14, or 15 months. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 days. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 weeks. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 months. In some embodiments, the compound is administered at least once a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least twice a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least twice a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least once every two weeks for a period of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once every two weeks for a period of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least once every four weeks for a period of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once every four weeks for a period of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months.

The subject of the described methods may be a mammal, and it includes humans and non-human mammals. In some embodiments, the subject is a human, such as an adult human.

Some embodiments include a method for treating an HBV virus in a subject infected with the virus comprising administering a therapeutically effective amount of one or more ASO of the present disclosure or a composition of the present disclosure to the subject in need thereof thereby reducing the viral load of the virus in the subject and/or reducing a level of a virus antigen in the subject. The ASO may be complementary or hybridize to a portion of the target RNA in the virus, e.g., a second X region and/or an S region of HBV.

In some embodiments, a modified oligonucleotide as described herein can be used in combination with one or more additional agent(s) for treating and/or inhibiting replication HBV and/or HDV. When the compounds (e.g., ASOs) described herein are co-administered with an additional agent, the effective amount may be less than when the compound is used alone. Additional agents include, but are not limited to, an interferon, nucleoside/nucleotide analogs, a capsid assembly modulator (CAM), siRNA, other ASOs, Nucleic Acid Polymers or S-Antigen Transport-inhibiting Oligonucleotide Polymers (NAPs or STOPS), an entry inhibitor and/or a small molecule immunomodulator. Examples of additional agents include ALG-010133, ALG-000184, recombinant interferon alpha 2b, IFN-α, PEG-IFN-α-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, DCR-HBVS, JNJ-6379, GLS4, ABI-H0731, JNJ-440, NZ-4, RG7907, EDP-514, AB-423, AB-506, ABI-H03733 and ABI-H2158. In some embodiments, any of the ASOs disclosed herein are co-administered with one of STOPS. Exemplary STOPS are described in International Publication No. WO2020/097342 and U.S. Publication No. 2020/0147124, both of which are incorporated by reference in their entirety. In some embodiments, the STOP is ALG-010133. In some embodiments, any of the ASOs disclosed herein are co-administered with tenofovir. In some embodiments, any of the ASOs disclosed herein are co-administered with a CAM. Exemplary CAMs are described in Berke et al., Antimicrob Agents Chemother, 2017, 61(8):e00560-17, Klumpp, et al., Gastroenterology, 2018, 154(3):652-662.e8, International Application Nos. PCT/US2020/017974, PCT/US2020/026116, and PCT/US2020/028349 and U.S. application Ser. Nos. 16/789,298, 16/837,515, and 16/849,851, each which is incorporated by reference in its entirety. In some embodiments, the CAM is ALG-000184, ALG-001075, ALG-001024, JNJ-632, BAY41-4109, or NVR3-778. In some embodiments, the ASO and the additional agent are administered simultaneously. In some embodiments, the ASO and the additional agent are administered sequentially. In some embodiments, the ASO is administered prior to administering the additional agent. In some embodiments, the ASO is administered after administering the additional agent.

Definitions

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates that may need to be independently confirmed.

EXAMPLES

The following examples illustrate certain embodiments of the present disclosure to aid the skilled person in practicing the disclosure. Accordingly, the examples are in no way considered to limit the scope of the disclosure.

Example 1: ASO Synthesis

Gapmer ASO Sequences

The DNA, 2'-O-Me, 2'-MOE and LNA phosphoramidite monomers were procured from commercially available sources (Hongene Biotech USA Inc.). All the monomers were dried in vacuum desiccator with desiccants ($P_2O_5$, RT 24h). Universal solid supports (CPG) attached were obtained from ChemGenes corporation. The chemicals and solvents for synthesis workflow were purchased from VWR/Sigma commercially available sources and used without any purification or treatment. Solvent (acetonitrile) and solutions (amidite and activator) were stored over molecular sieves during synthesis.

The control and target oligonucleotide sequences were synthesized on an Expedite 8909 synthesizer using the standard cycle written by the manufacturer with modifications to a few wait steps and modified coupling steps. The solid support was controlled pore glass and the monomers contained standard protecting groups. Each chimeric oligonucleotide was individually synthesized using commercially available 5'-O-(4,4'-dimethoxytrityl)-3'-O-(2-cyanoethyl-N, N-diisopropyl) DNA, 2'-OMe, 2'-MOE and or LNA phosphoramidite monomers of 6-N-benzoyladenosine ($A^{Bz}$), 4-N-acetylcytidine ($C^{Ac}$), 2-N-isobutyrylguanosine ($G^{iBu}$), and Uridine (U) or Thymidine (T), according to standard solid phase Phosphoramidite synthesis protocols. The 2'-O-Me-2,6-diaminopurine phosphoramidite was purchased from Glen Research. The phosphoramidites were prepared as 0.1 M solutions in anhydrous acetonitrile. 5-Ethylthiotetrazole was used as activator, 3% dichloroacetic acid in dichloromethane was used to detritylate, acetic anhydride in THF and 16% N-methylimidazole in THF were used to cap, and DDTT ((dimethylamino-methylidene) amino)-3H-1,2,4-dithiazaoline-3-thione was used as the sulfur-transfer agent for the synthesis of oligoribonucleotide phosphorothioates. An extended coupling of 0.1M solution of phosphoramidite in $CH_3CN$ in the presence of 5-(ethylthio)-1H-tetrazole activator to a solid bound oligonucleotide followed by extended capping, oxidation and deprotection afforded modified oligonucleotides. The stepwise coupling efficiency of all modified phosphoramidites was more than 98.5%.

Deprotection and cleavage from the solid support was achieved with mixture of ammonia methylamine (1:1, AMA) for 15 min at 65° C., when the universal linker was used, the deprotection was left for 90 min at 65° C. or solid supports were heated with aqueous ammonia (28%) solution at 55° C. for 8 h to deprotect the base labile protecting groups.

After filtering to remove the solid support, the deprotection solution was removed under vacuum in a GeneVac centrifugal evaporator.

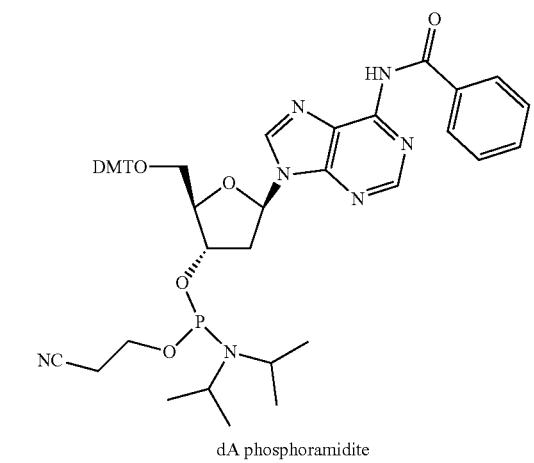

dA phosphoramidite

35
-continued
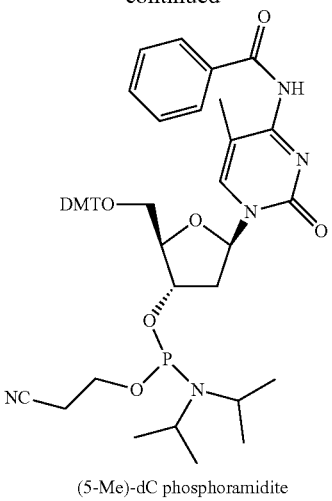
(5-Me)-dC phosphoramidite
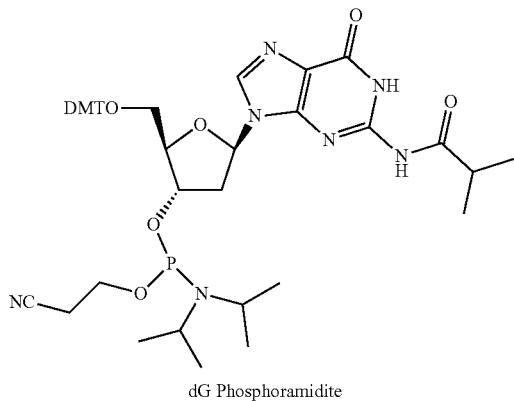
dG Phosphoramidite
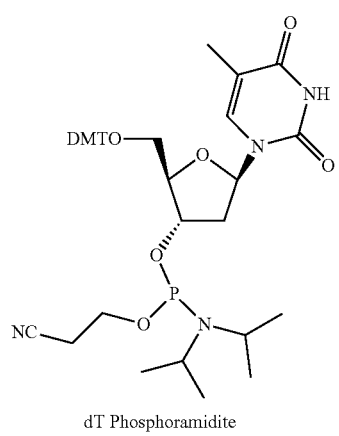
dT Phosphoramidite
36
-continued
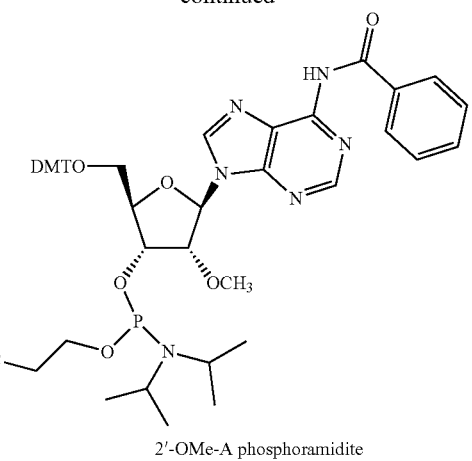
2'-OMe-A phosphoramidite
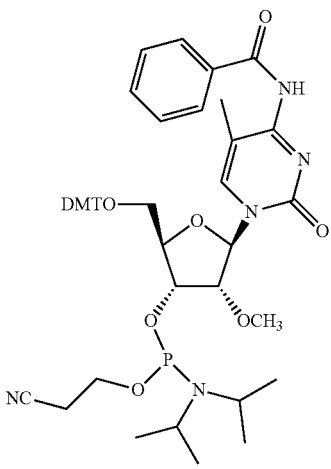
2'-OMe-(5m)C phosphoramidite
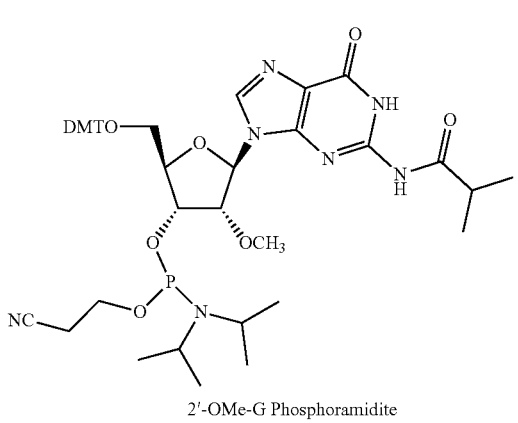
2'-OMe-G Phosphoramidite

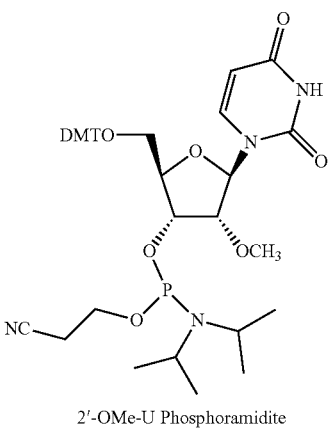
2'-OMe-U Phosphoramidite
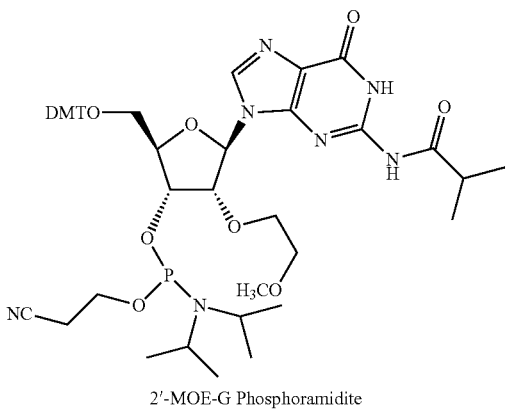
2'-MOE-G Phosphoramidite
The 2'-MOE phosphoramidites
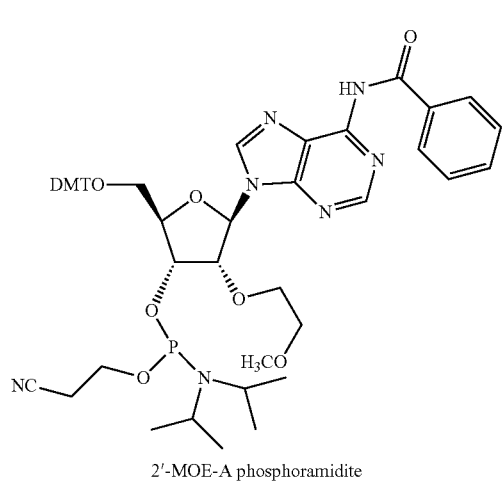
2'-MOE-A phosphoramidite
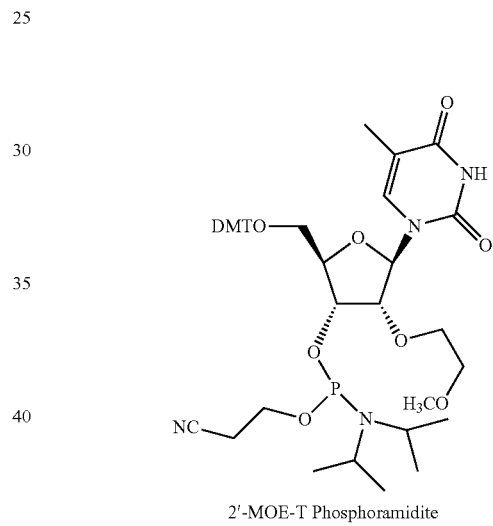
2'-MOE-T Phosphoramidite
The Locked Nucleic Acid (LNA) Phosphoramidite
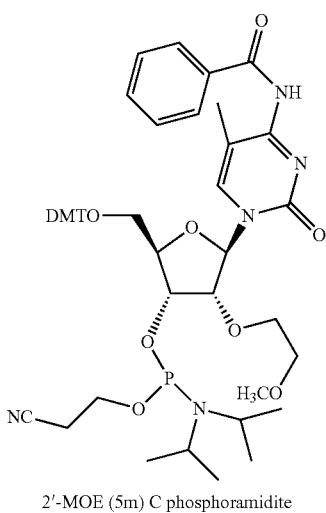
2'-MOE (5m) C phosphoramidite
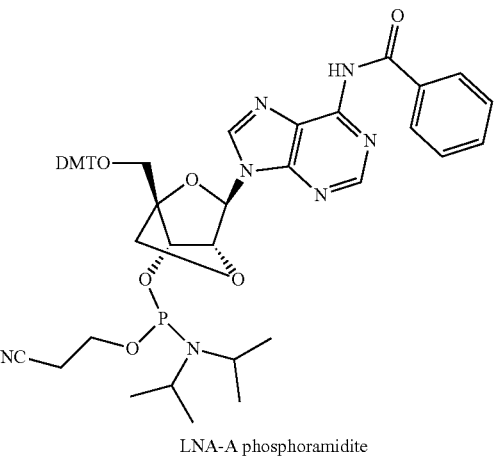
LNA-A phosphoramidite

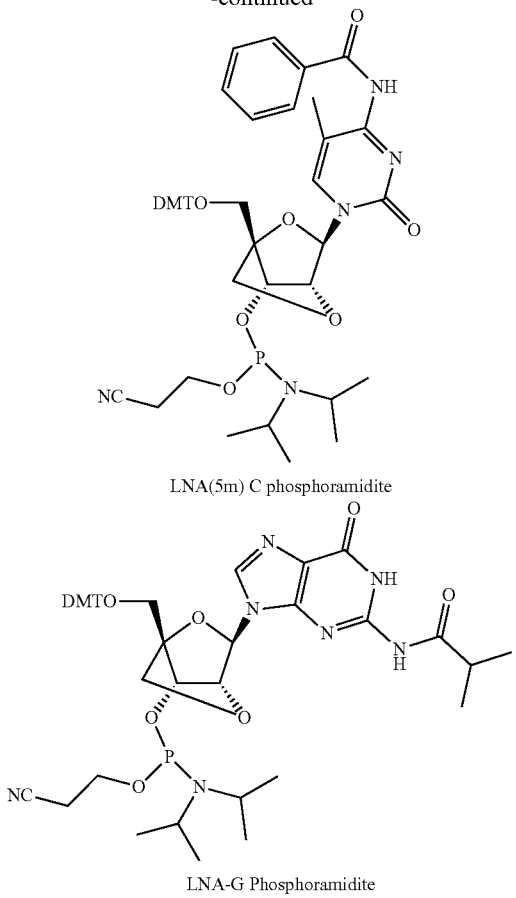

LNA(5m) C phosphoramidite

LNA-G Phosphoramidite

LNA-T Phosphoramidite

Modified Gapmer Sequences

The AmNA (N-Me)-T, AmNA (N-Me)-4-N-benzoyl (5m) cytidine ((5m) $C^{Bz}$), AmNA (N-Me)-4-N-benzoylcytidine ($A^{Bz}$), and AmNA (N-Me)-2-N-pac ($G^{pac}$), were purchased from Luxna Biotech, whereas scp-BNA-T, scp-BNA-6-N-benzoyladenosine ($A^{Bz}$), scp-BNA-4-N-benzoyl-5 methyl cytidine ((5m) $C^{Bz}$), scp-BNA-2-N-iguanosine ($G^{iBu}$) phosphoramidite monomers synthesized by following the procedure described in references (Takao Yamaguchi, Masahiko Horiba and Satoshi Obika; *Chem. Commun.*, 2015, 51, 9737-9740; Masahiko Horiba, Takao Yamaguchi, and Satoshi Obika; *Journal of Organic Chemistry*, 2016, 81, 11000-11008). All the monomers were dried in a vacuum desiccator with desiccants (KOH and $P_2O_5$, at room temperature for 24 hours). In the case of AmNA(N-Me)-PS-DNA-PS and scp-BNA-PS-DNA-PS, modifications the synthesis was carried out on a 1 µM scale in a 3' to 5' direction with the phosphoramidite monomers diluted to a concentration of 0.12 M in anhydrous $CH_3CN$ in the presence of 0.3 M 5-(benzylthio)-1H-tetrazole activator (coupling time 16 min) to a solid bound oligonucleotide followed by modified capping, oxidation and deprotection afforded modified oligonucleotides. The stepwise coupling efficiency of all modified phosphoramidites was more than 97%. The DDTT (dimethylamino-methylidene) amino)-3H-1,2,4-dithiazaoline-3-thione was used as the sulfur-transfer agent for the synthesis of oligoribonucleotide phosphorothioates. Oligonucleotide-bearing solid supports were washed with 20% DEA solution in acetonitrile for 15 min then column was washed thoroughly with MeCN. The support was heated at 65° C. with diisopropylamine:water:methanol (1:1:2) for 8 h in heat block to cleavage from support and deprotect the base labile protecting groups.

AmNA (N-Me) Monomers

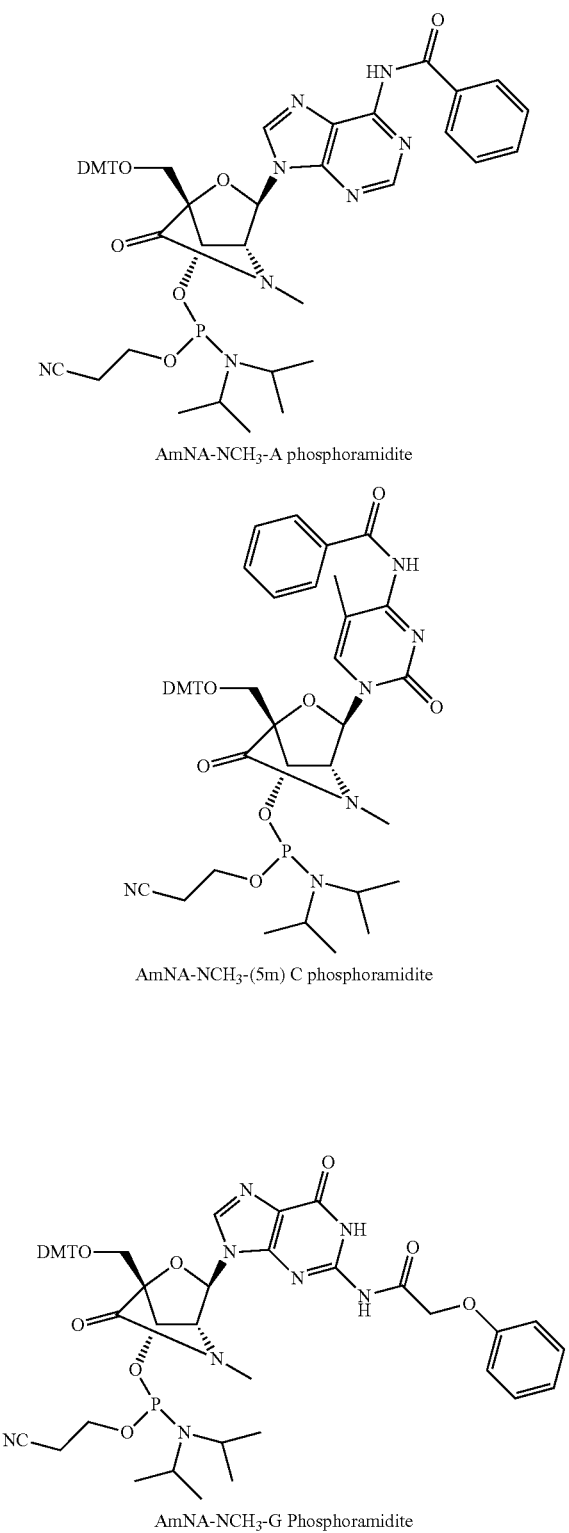

AmNA-NCH$_3$-A phosphoramidite

AmNA-NCH$_3$-(5m) C phosphoramidite

AmNA-NCH$_3$-G Phosphoramidite

-continued

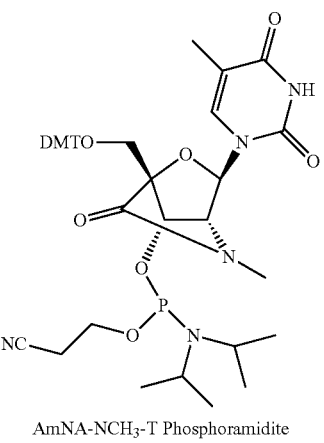

AmNA-NCH₃-T Phosphoramidite

-continued

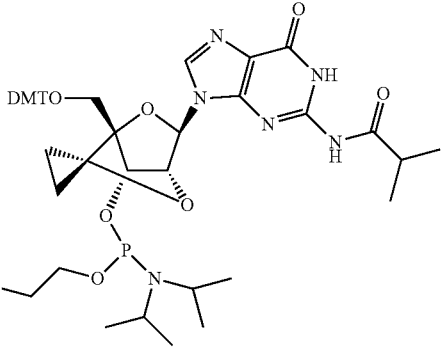

scp-BNA-G Phosphoramidite scp-BNA Monomers

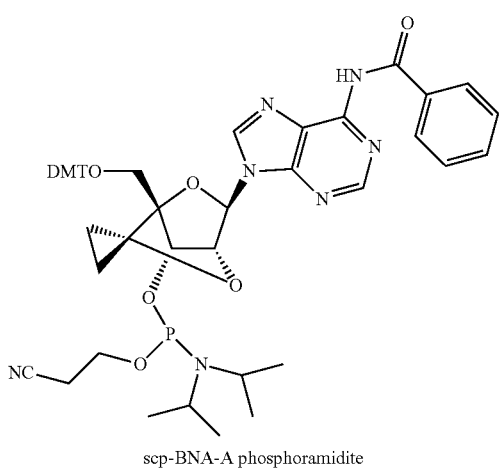

scp-BNA-A phosphoramidite

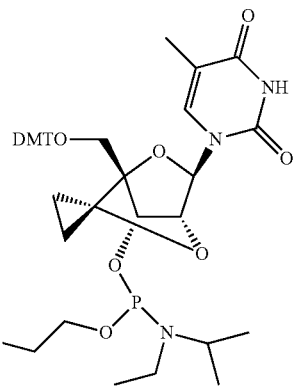

scp-BNA-T Phosphoramidite

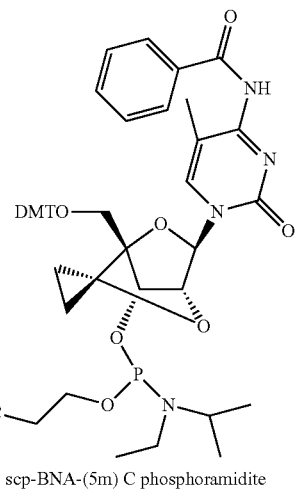

scp-BNA-(5m) C phosphoramidite

5' and 3'-GalNAc conjugated oligonucleotides were synthesized with various length GalNAc moieties, e.g., as described below. The GalNAc3, GalNAc4, GalNAc5 and GalNAc6 were conjugated to oligonucleotides during synthesis with 1 2, or 3 moieties in the same manner as described below. Further GalNAc moieties, such as GalNAc-1 and GalNAc-2, which are described previously herein, are also used to form 5' and 3'-GalNAc using post synthesis conjugation.

GalNAc Phosphoramidites

| GalNAc building blocks | After Attachment to Oligos (Nomenclature) |
|---|---|
| GalNAc-3 phosphoramidite | (GalNAc3-(PS)2-p) |

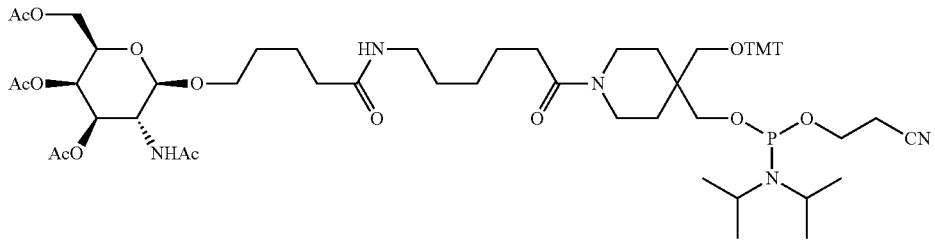

| GalNAc-4 phosphoramidite | (GalNAc4-(PS)2-p) |
| GalNAc-5 phosphoramidite | (GalNAc5-(PS)2-p) |
| GalNAc-6 phosphoramidite | (GalNAc6-(PS)2-p) |

Quantitation of Crude Oligomer or Raw Analysis

Samples were dissolved in deionized water (1.0 mL) and quantitated as follows: Blanking was first performed with water alone on Nanodrop UV spectrophotometer. Nano Drop instruments can measure a wide concentration range of nucleic acids through use of multiple path lengths. The most accurate quantification results can be achieved by measuring diluted oligonucleotides with an absorbance at 260 nm. The crude material is stored at −20° C.

Crude HPLC/LC-MS Analysis

The 0.1 OD of the crude samples were used for crude MS analysis. After confirming the crude LC-MS data, then the purification step was performed.

HPLC Purification

The Phosphodiester (PO), Phosphorothioate (PS) and chimeric modified oligonucleotides were purified by anion-exchange HPLC. The buffers were 20 mM sodium phosphate in 10% $CH_3CN$, pH 8.5 (buffer A) and 20 mM sodium phosphate in 10% $CH_3CN$, 1.8 M NaBr, pH 8.5 (buffer B). Fractions containing full-length oligonucleotides were pooled, desalted and lyophilized.

The lipid conjugated oligonucleotides were purified by an in-house packed RPC-Source15 reverse-phase column. The buffers were 20 mM sodium acetate in 10% $CH_3CN$, (buffer A) and $CH_3CN$ (buffer B). Fractions containing full-length oligonucleotides were pooled, desalted and lyophilized.

Desalting of Purified Oligomer

The purified dry oligomer was then desalted using Sephadex G-25 M (Amersham Biosciences). The cartridge was conditioned with 10 mL of deionized water thrice. The purified oligonucleotide dissolved thoroughly in 2.5 mL deionized water was applied to the cartridge with very slow drop wise elution. The salt free oligomer was eluted with 3.5 ml deionized water directly into a screw cap vial.

Final HPLC and Electrospray LC/MS Analysis

Approximately 0.10 OD of oligomer is dissolved in water and then pipetted in special vials for IEX-HPLC and LC/MS analysis. Analytical HPLC and ES LC-MS established the integrity of the chimeric oligonucleotides.

Post-Synthesis Conjugation of GalNAc Esters to Oligonucleotides

5'-C6-Amino Precursor Synthesis

The sequences were synthesized at 10 µmol scale using universal support (Loading 65 µmol/g). At the 5'-terminal to introduce C6-$NH_2$ linker the 6-(4-monomethoxytritylamino) hexyl-(2-cyanoethyl)-(N, N-diisopropyl)-phosphoramidite in 0.1 M Acetonitrile was used with coupling time 10 min. The Oligonucleotide-bearing solid supports were heated at room temperature with aqueous ammonia/Methylamine (1:1) solution for 3 h in shaker to cleavage from support and deprotect the base labile protecting groups. After IEX purification and desalting the C6-$NH_2$ modified ASO's was used to perform post synthesis conjugation.

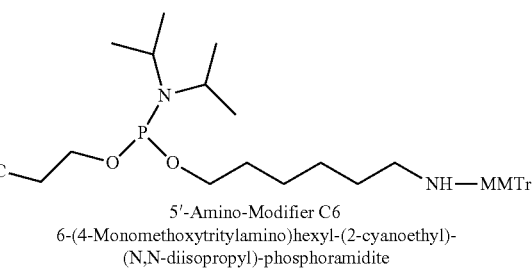

5'-Amino-Modifier C6
6-(4-Monomethoxytritylamino)hexyl-(2-cyanoethyl)-
(N,N-diisopropyl)-phosphoramidite GalNAc Ester for Conjugation
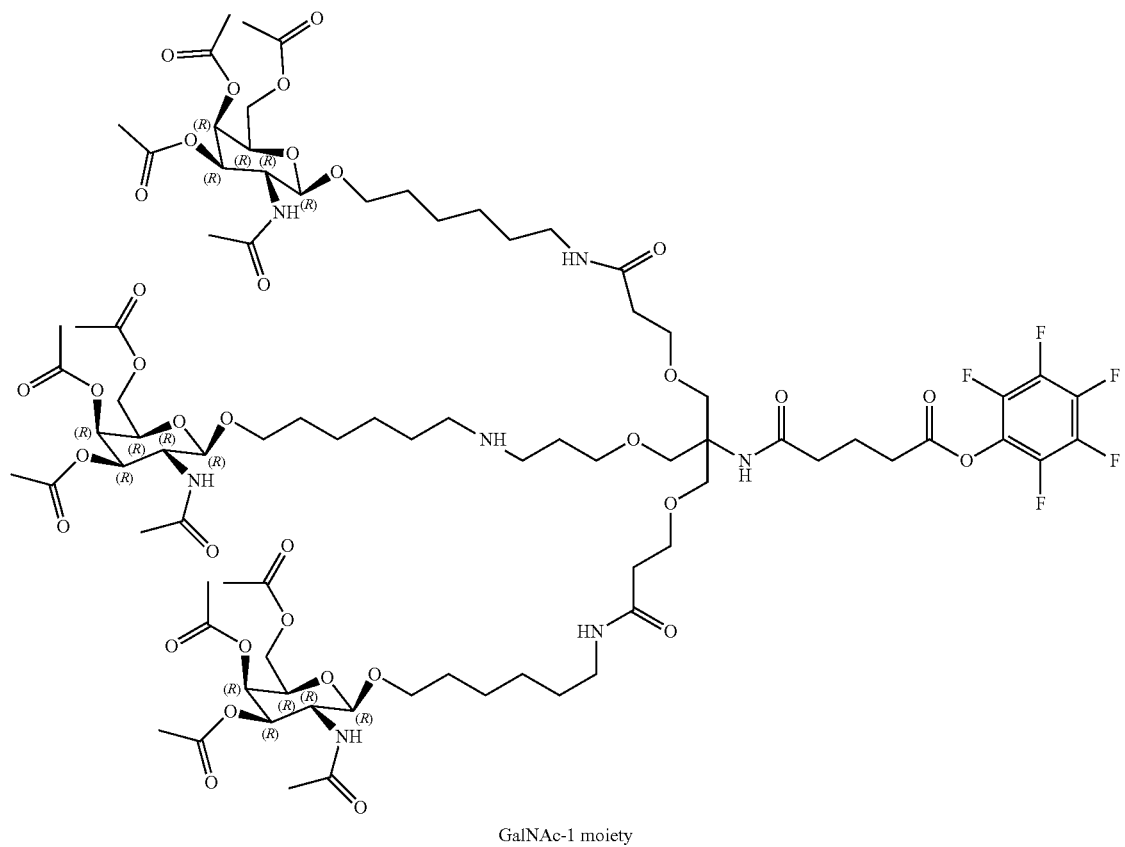
GalNAc-1 moiety
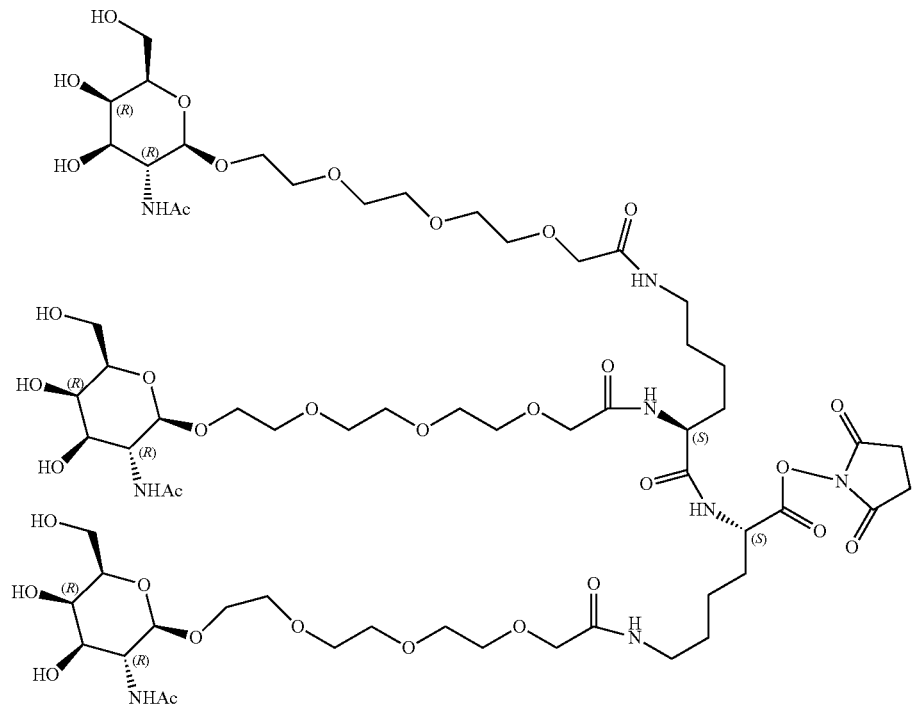
GalNAc-2 moiety Post Synthesis Conjugation of 5'-GalNAc Synthesis The 5'-C6-NH$_2$ modified sequences were dissolved in 0.2 M Sodium bicarbonate buffer, pH 8.5 (0.015 mM) and 5-7 mol equivalent of GalNAc ester dissolved in DMSO was added. The reaction mixture was stirred at room temperature for 4 h. The sample was analyzed to confirm if any unreacted amino modified ASO's is present. To this aqueous ammonia (28 wt. %) was added (5× reaction volume) and stirred at room temperature for 2-3 h. Reaction mixture concentrated under reduced pressure and residue dissolved in water and purified by HPLC on a strong anion exchange column.

Example 2. HBsAg Release Assay Protocol (HepG2.2.15)

HepG2.2.15 cells (a stable cell line with four integrated HBV genomes) were maintained in DMEM medium with 10% fetal bovine serum (FBS) and 1% penicillin/streptomycin, 1% Glutamine, 1% non-essential amino acids, 1% Sodium Pyruvate and 250 µm/ml G418. Cells were maintained at 37° C. in a 5% CO$_2$ atmosphere. For HBsAg release assay, assay medium was made: DMEM with 5% FBS, 1% penicillin/streptomycin, 1% Glutamine and 1% DMSO. The day before assay, trypsinize HepG2.2.15 cells were washed with Assay Medium once, spun at 250 g×5 min, resuspended with Assay Medium, and seed cells at 50,000/well in assay medium in collagen coated 96 well plates. On the next day, ASOs were diluted with Opti-MEM, 9-pt, 3-fold dilution and Lipofectamine RNAiMAX (Invitrogen) was diluted according manufacturer's manual. The ASO dilution and RNAiMAX dilution was mixed, left at room temperature for 5 minutes and 15 µl was added to each well of 96 well plate. The plates were left at 37° C., 5% CO$_2$ in an incubator for 5 days. After incubation, the supernatant was harvested and measured for HBsAg with ELISA kit (Diasino). The cell viability was measured with CellTiter-Glo (Promega). The EC$_{50}$, the concentration of the drug required for reducing HBsAg secretion by 50% in relation to the untreated cell control was calculated using the Prism Graphpad. The CC$_{50}$, the concentration of the drug required for reducing cell viability by 50% in relation to the untreated cell control was calculated with the same software.

The resulting EC$_{50}$ and CC$_{50}$ for the compounds in Table 1 are presented in the following Table 2. The EC$_{50}$ values are as follows: A: <0.1 nM, B: 0.1 nM-1 nM, C: 1-10 nM.

TABLE 2

| | HBsAg Release Assay | |
| --- | --- | --- |
| ASO # | HepG2.2.15 HBsAg Release Assay EC$_{50}$ | HepG2.2.15 Cell Viability CC$_{50}$ nM |
| 1 | A | >10 |
| 2 | A | >10 |
| 3 | A | >10 |
| 4 | A | >10 |
| 5 | B | >10 |
| 6 | B | >10 |
| 7 | B | >10 |
| 8 | B | >10 |
| 9 | B | >10 |
| 10 | B | >10 |
| 11 | B | >10 |
| 12 | B | >10 |
| 13 | B | >10 |
| 14 | B | >10 |
| 15 | B | >10 |
| 16 | B | >10 |
| 17 | B | >10 |
| 18 | B | >10 |
| 19 | B | >10 |
| 20 | B | >10 |
| 21 | B | >10 |
| 22 | B | >10 |
| 23 | B | >10 |
| 24 | B | >10 |
| 25 | B | >10 |
| 26 | B | >10 |
| 27 | B | >10 |
| 28 | B | >10 |
| 29 | B | >10 |
| 30 | B | >10 |
| 31 | B | >10 |
| 32 | B | >10 |
| 33 | B | >10 |
| 34 | B | >10 |
| 35 | B | >10 |
| 36 | B | >10 |
| 37 | B | >10 |
| 38 | B | >10 |
| 39 | B | >10 |
| 40 | B | >10 |
| 41 | B | >10 |
| 42 | B | >10 |
| 43 | B | >10 |
| 44 | B | >10 |
| 45 | B | >10 |
| 46 | B | >10 |
| 47 | B | >10 |
| 48 | B | >10 |
| 49 | B | >10 |
| 50 | B | >10 |
| 51 | B | >10 |
| 52 | B | >10 |
| 53 | C | >10 |
| 54 | C | >10 |
| 55 | C | >10 |
| 56 | C | >10 |
| 57 | C | >10 |
| 58 | C | >10 |
| 59 | C | >10 |
| 60 | C | >10 |
| 61 | C | >10 |
| 62 | C | >10 |
| 63 | C | >10 |
| 64 | C | >10 |
| 65 | C | >10 |
| 66 | C | >10 |
| 67 | C | >10 |
| 68 | C | >10 |
| 69 | C | >10 |
| 70 | C | >10 |
| 71 | C | >10 |
| 72 | C | >10 |
| 73 | C | >10 |
| 74 | C | >10 |
| 75 | C | >10 |
| 76 | C | >10 |
| 77 | C | >10 |
| 78 | C | >10 |
| 79 | C | >10 |
| 80 | C | >10 |
| 81 | C | >10 |
| 82 | C | >10 |
| 83 | C | >10 |
| 84 | C | >10 |
| 85 | C | >10 |
| 86 | C | >10 |
| 87 | C | >10 |
| 88 | C | >10 |
| 89 | B | >10 |
| 90 | C | >10 |
| 91 | C | >10 |
| 92 | B | >10 |
| 93 | C | >10 |
| 94 | C | >10 |

TABLE 2A

Serum HBsAg Log Reduction (nadir) with 1x5mg/kg

| SEQ ID NO. | ASO # | Sequence 5' to 3' | Location, length & structure | Serum HBsAg |
|---|---|---|---|---|
| 118 | 116 | 5'lnGpslnApslnTpsTps(5m)CpsApsGps(5m)CpsGps(5m)Cps(5m)CpsGpsApsln(5m)CpslnGpslnGpslnG 3' | 1432_17mer_3-10-4 | B |
| 119 | 117 | 5'lnGpslnGpslnApsTpsTps(5m)CpsApsGps(5m)CpsGps(5m)Cps(5m)CpsGpslnApsln(5m)CpslnG 3' | 1580_16mer_3-10-3 | B |
| 120 | 118 | 5'ln(5m)Cpsln(5m)CpslnApsln(5m)Cps(5m)CpsAps(5m)CpsGpsApsGpsTps(5m)CpsTpsApslnGpslnApsln(5m)C 3' | 1576_17mer_4-10-3 | B |
| 121 | 119 | 5'lnGpslnApslnTpslnApslnApsApsApsAps(5m)CpsGps(5m)Cps(5m)CpsGps(5m)CpsCpslnApslnGpslnApsln(5m)C 3' | 1431_17mer_5-8-4 | C |

In Table 2A, the bold nucleosides contain the following modifications:

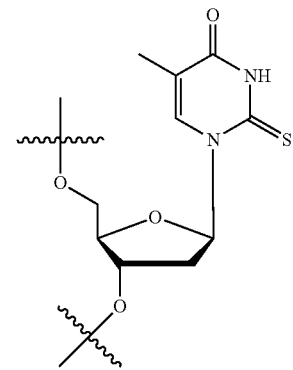

(5OH)C (2s)T

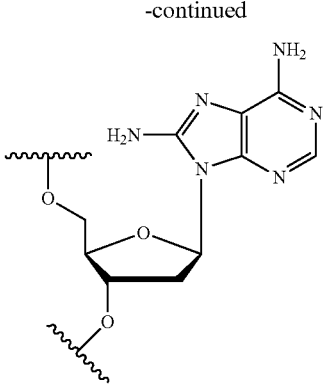

(8NH)A (8NH)G

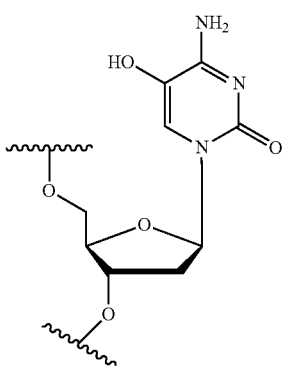

Example 3. GalNac ASO Testing in AAV-HBV Mouse Model

AAV/HBV is a recombinant AAV carrying replicable HBV genome. Taking advantage of the highly hepatotropic feature of genotype 8 AAV, the HBV genome can be efficiently delivered to the mouse liver cells. Infection of immune competent mouse with AAV/HBV can result in long term HBV viremia, which mimics chronic HBV infection in patients. The AAV/HBV model was used to evaluate the in vivo activity of various types of anti-HBV agents. Mice were infected with AAV-HBV on day −28 of the study. The test articles or negative control (PBS) were dosed subcutaneously (unless specified otherwise) as a single dose on day 0 at 5 mg/kg, or single dose on day 0 at 10 mg/kg; or 3×10 mg/kg once a week (QW); or 3×10 mg/kg every 3 days (Q3D); or 5×10 mg/kg Q3D; or 6 doses of 3 mg/kg on days 0, 3, 7, 14, 21, 28; or 6 doses of 10 mg/kg on days 0, 3, 7, 14, 21, 28. Serial blood collections were taken every 5 days on day 0, 5, 10 and 15; or longer duration depending each study design. Serum HBV S antigen (HBsAg),E antigen (HBeAg) and ALT were assayed through the following methods:

| Parameters | Equipment | Reagent |
|---|---|---|
| HBsAg | ARCHITECT i2000 (Abbott Laboratories, Lake Bluff, IL, USA) | HBsAg Reagent Kit (Abbott Ireland Diagnostics Division, Finisklin Business Park Sligo, IRL) Catalog: 6C36/08P08 |
| HBeAg | ARCHITECT i2000 (Abbott Laboratories, Lake Bluff, IL, USA) | HBeAg Reagent Kit (Abbott GmbH & Co. KG, Wiesbaden, GER) Catalog: 6C32/07P64 |
| Alanine Aminotransferase (ALT) | Roche Cobas 6000 c501 Chemistry Analyzer (Roche Diagnostics, Mannheim, GER) | Alanine Aminotransferase acc. to IFCC (Roche Diagnostics, Mannheim, GER) Catalog: ACN 685 |

The resulting nadir $\log_{10}$ reduction in serum HBsAg during the study are presented in the following table, where A≥1 $\log_{10}$ reduction in HBsAg, B is 0.5-1 $\log_{10}$ reduction in HBsAg, and C is <0.5 $\log_{10}$ reduction in HBsAg

TABLE 3

Serum HBsAg Log Reduction (nadir) for mice treated with 1x5 mg/kg ASO

| SEQ ID No. | ASO # | Sequence 5' to 3' | Location, length & structure | Serum HBsAg |
|---|---|---|---|---|
| 122 | 95 | 5'-GalNAc1-C6-p-lnGpslnApslnTpslnTps(5m)CpsApsGps(5m)CpsGps(5m)Cps(5m)CpsGpsApsln(5m)CpslnGpslnG 3' | 1432_16mer_4-9-3 | B |
| 123 | 96 | 5'-GalNAc3-(PS)2-p-lnGpslnTpslnGpsApsApsGps(5m)CpsGpsApsApsGpsTpslnGpsln(5m)CpslnA 3' | 1580_15mer_3+9+3 | C |
| 124 | 97 | 5'-GalNAc1-C6-p-lnApslnApslnGpsln(5m)CpsGpsApsApsGpsTpsGps(5m)mCpsApsln(5m)CpslnApsln(5m)CpslnG 3' | 1576_16mer_4-8-4 | B |
| 125 | 98 | 5'-GalNAc3-(PS)2-p-lnGpslnApslnTpsTps(5m)CpsApsGps(5m)CpsGps(5m)Cps(5m)CpsGpsApsln(5m)CpslnGpslnGpslnG 3' | 1431_17mer_3-10-4 | A |
| 126 | 99 | 5'-GalNAc3-(PS)2-p-lnGpslnApslnGpsGpsTpsGpsApsApsGps(5m)CpsGpsApsApslnGpslnTpslnG 3' | 1582_16mer_3-10-3 | B |
| 127 | 100 | 5'-GalNAc3-(PS)2-p-ln(5m)Cpsln(5m)CpslnAps(5m)Cps(5m)CpsAps(5m)CpsGpsApsGpsTps(5m)CpsTpslnApslnGpslnApsln(5m)C 3' | 246_17mer_3-10-4 | A |
| 128 | 101 | 5'-GalNAc3-(PS)2-p-lnGpsln(5m)CpslnGpsApsApsGpsTpsGps(5m)CpsAps(5m)CpsAps(5m)CpslnGpslnG 3' | 1575_15mer_3-10-2 | B |
| 129 | 102 | 5'-GalNAc3-(PS)2-p-lnGpslnGpslnApslnTpsTps(5m)CpsApsGps(5m)CpsGps(5m)Cps(5m)CpsGpslnApsln(5m)CpslnGpslnG 3' | 1432_17mer_4-9-4 | C |
| 130 | 103 | 5'-GalNAc3-(PS)2-p-lnGpslnGpslnTpsGpsApsApsGps(5m)CpsGpsApsApsGpsTpslnGpsln(5m)C 3' | 1581_15mer_3-10-2 | B |
| 131 | 104 | 5'-GalNAc3-(PS)2-p-lnApslnGpsln(5m)CpsGpsApsApsGpsTpsGps(5m)CpsAps(5m)CpsApsln(5m)CpslnG 3' | 1576_15mer_3-10-2 | B |
| 132 | 105 | 5'-GalNAc3-(PS)2-p--lnApslnGpslnGpsTpsGpsApsApsGps(5m)CpsGpsApsApsGpslnTpslnG 3' | 1582_15mer_3-10-2 | A |
| 133 | 106 | 5'-GalNAc5-(PS)2-p-po-lnApslnGpslnGpsTpsGps(5m)CpsGps(5m)Cps(5m)Cps(5m)Cps(5m)CpsGpslnTpslnGpslnG 3' | 1517_15mer_3-9-3 | A |
| 134 | 107 | 5'-GalNAc1-C6-p-CA-lnGpslnGpslnApsTpsTps(5m)CpsApsGps(5m)CpsGps(5m)Cps(5m)CpsGpslnApsln(5m)CpslnG 3' | 1433_16mer_3-10-3 | A |

TABLE 3-continued

Serum HBsAg Log Reduction (nadir) for mice treated with 1x5 mg/kg ASO

| SEQ ID No. | ASO # | Sequence 5' to 3' | Location, length & structure | Serum HBsAg |
|---|---|---|---|---|
| 135 | 108 | 5'-GalNAc1-C6-p-CA-lnGpslnApslnGpsApsGpsGpsTpsGps(5m)CpsGps(5m)Cps(5m)Cps(5m)Cpsln(5m)CpslnGpslnT 3' | 1519_16mer_3-10-3 | A |
| 136 | 109 | 5'-GalNAc1-C6-p-CA-lnApslnGpslnGpslnTpsGpsApsApsGps(5m)CpsGpsApsApsGpslnTpslnGpsln(5m)C 3' | 1581_16mer_4-9-3 | A |
| 137 | 110 | 5'-GalNAc1-C6-p-CA-lnGpslnGpslnTpsGpsApsApsGps(5m)CpsGpsApsApsGpslnTpslnGpsln(5m)CpslnA 3' | 1580_16mer_3-9-4 | A |
| 138 | 111 | 5'-GalNAc1-C6-p-CA-ln(5m)Cpsln(5m)CpslnGpsln(5m)Cps(5m)CpsTpsGpsTpsApsAps(5m)CpsApsln(5m)CpslnGpslnApslnG 3' | 191_16mer_4-8-4 | A |
| 139 | 112 | 5'-GalNAc1-C6-p-CA-lnGpslnApslnTpslnApslnApsApsAps(5m)CpsGps(5m)Cps(5m)CpsGps(5m)CpslnApslnGpslnApsln(5m)C 3' | 381_17mer_5-8-4 | A |
| 140 | 113 | 5'-GalNAc1-C6-p-CA-ln(5m)Cpsln(5m)CpslnApsln(5m)Cps(5m)CpsAps(5m)CpsGpsApsGpsTps(5m)CpsTpsApslnGpslnApsln(5m)C 3' | 246_17mer_4-10-3 | A |
| 141 | 114 | 5'-GalNAc1-C6-p-CA-ln(5m)CpslnApsln(5m)Cpsln(5m)CpsAps(5m)CpsGpsApsGpsTps(5m)CpsTpsApsGpslnApsln(5m)CpslnT 3' | 245_17mer_4-10-3 | A |
| 142 | 115 | 5'-GalNAc1-C6-p-CA-ln(5m)Cpsln(5m)CpslnGps(5m)Cps(5m)CpsTpsGpsTpsApsAps(5m)CpsApsln(5m)CpslnGpslnApslnG 3' | 191_16mer_3-9-4 | A |
| 143 | 108A | 5'-GalNAc5-(PS)2-p-lnGpslnApslnGpsApsGpsGpsTpsGps(5m)CpsGps(5m)Cps(5m)Cps(5m)Cpsln(5m)CpslnGpslnT 3' | 1519_16mer_3-10-3 | |
| 144 | 108B | 5'-GalNAc5-(PS)2-p-lnGpslnApslnGpsApsGpsGpsTpsGps(5m)CpsGps(5m)Cps(5m)Cps(5m)Cpsln(5m)CpslnGpsAmT 3' | 1519_16mer_3-10-3 | |
| 145 | 108C | 5'-GalNAc5-(PS)2-p-lnGpslnApslnGpsApsGpsGpsTpsGps(5m)CpsGps(5m)Cps(5m)Cps(5m)CpsAm(5m)CpslnGpslnT 3' | 1519_16mer_3-10-3 | |
| 146 | 108D | 5'-GalNAc5-(PS)2-p-lnGpslnApslnGpsApsGpsGpsTpsGps(5m)CpsGps(5m)Cps(5m)Cps(5m)Cpsln(5m)CpsGpsscpT 3' | 1519_16mer_3-10-3 | |
| 147 | 108E | 5'-GalNAc5-(PS)2-p-lnGpslnApslnGpsApsGpsGpsTpsGps(5m)CpsGps(5m)Cps(5m)Cps(5m)CpsscpCpslnGpslnT 3' | 1519_16mer_3-10-3 | |
| 148 | 107A | 5'-GalNAc6-(PS)2-p-lnGpslnGpslnApsTpsTps(5m)CpsApsGps(5m)CpsGps(5m)Cps(5m)CpsGpslnApsln(5m)CpslnG 3 | 1433_16mer_3-10-3 | |
| 149 | 107B | 5'-GalNAc6-(PS)2-p-lnGpslnGpslnAps(2s)TpsTps(5m)CpsApsGps(5m)CpsGps(5m)Cps(5m)CpsGpslnApsln(5m)CpslnG 3' | 1433_16mer_3-10-3 | |
| 150 | 107C | 5'-GalNAc6-(PS)2-p-lnGpslnGpslnApsTps(2s)Tps(5m)CpsApsGps(5m)CpsGps(5m)Cps(5m)CpsGpslnApsln(5m)CpslnG 3' | 1433_16mer_3-10-3 | |
| 151 | 107D | 5'-GalNAc6-(PS)2-p-lnGpslnGpslnApsTpsTps(5oh)CpsApsGps(5m)CpsGps(5m)Cps(5m)CpsGpslnApsln(5m)CpslnG 3' | 1433_16mer_3-10-3 | |
| 152 | 107E | 5'-GalNAc4-(PS)2-p-mU-po-lnGpslnGpslnApsTps(2s)Tps(5m)CpsApsGps(5m)CpsGps(5m)Cps(5m)CpsGpslnApsln(5m)CpslnG 3' | 1433_16mer_3-10-3 | |

TABLE 3-continued

Serum HBsAg Log Reduction (nadir) for mice treated with 1x5 mg/kg ASO

| SEQ ID No. | ASO # | Sequence 5' to 3' | Location, length & structure | Serum HBsAg |
|---|---|---|---|---|
| 153 | 107F | 5'-GalNAc4-(PS)2-p-mU-po-lnGpslnGpslnApsTps(2s)Tps(5m)CpsApsGps(5m)CpsGps(5m)Cps(5m)CpsGpslnApsscp(5m)CpslnG-3' | 1433_16mer_3-10-3 | |
| 154 | 73B-G | 5'-GalNAc4-(PS)2-p-mA-po-lnGpslnApslnTpslnApslnApsApsAps(5m)CpsGps(5m)Cps(5m)CpsGps(5m)CpslnApslnGpslnApsscp(5m)C-3' | 381_17mer_5-8-4 | |
| 155 | 73C-G | 5'-GalNAc4-(PS)2-p-mA-po-lnGpslnApslnTpslnApslnAps(8nh)ApsAps(5m)CpsGps(5m)Cps(5m)CpsGps(5m)CpslnApslnGpslnApsscp(5m)C-3' | 381_17mer_5-8-4 | |
| 156 | 121 | 5'-GalNAc4-(PS)2-p-mU-lnGpslnApsscpTpsTps(5m)Cps(8nh)ApsGps(5m)CpsGps(5m)Cps(5m)CpsGpsApsln(5m)CpslnGpslnGpslnG-3' | 1431_17mer_3-10-4 | |
| 157 | 9C-G | 5'-GalNAc4-(PS)2-p-mU-po-lnGpslnApslnTpsTps(5m)CpsApsGps(5m)CpsGps(5m)Cps(5m)CpsGpsApsln(5m)CpslnGpslnGpslnG-3' | 1431_17mer_3-10-4 | |
| 158 | 34A-G | 5'-GalNAc4-(PS)2-p-mU-po-lnGpin(5m)CpsscpGpsAps(8nh)ApsGpsTpsGps(5m)CpsAps(5m)CpsAps(5m)CpslnGpslnG-3' | 1575_15mer_3-10-2 | |
| 159 | 23A-G | 5'-GalNAc4-(PS)2-p-mU-po-lnGpslnGpsscpTpsGpsApsApsGps(5m)CpsGpsApsApsGpslnTpslnGpsln(5m)CpslnA-3' | 1580_16mer_3-9-4 | |
| 160 | 25F-G | 5'-GalNAc4-(PS)2-p-mU-po-lnGpslnApslnGpsApsGpsGpsTpsGps(5m)CpsGps(5m)Cps(5m)Cps(5m)Cpsln(5m)CpslnGpslnT-3' | 1519_16mer_3-10-3 | |
| 161 | 25G-G | 5'-GalNAc4-(PS)2-p-mU-po-lnGpslnApslnGpsAps(8nh)GpsGpsTpsGps(5m)CpsGps(5m)Cps(5m)Cps(5m)Cpsscp(5m)CpslnGpslnT 3' | 1519_16mer_3-10-3 | |
| 162 | 40A-G | 5'-GalNAc4-(PS)2-p-mA-po-ln(5m)Cpsscp(5m)CpslnApsln(5m)Cps(5m)CpsAps(5m)CpsGpsApsGpsTps(5m)CpsTpsApslnGpslnApsln(5m)C-3' | 246_17mer_3-10-4 | |
| 163 | 47F-G | 5'-GalNAc4-(PS)2-p-mU-po-lnGpslnGpslnApsTpsTps(5m)CpsApsGps(5m)CpsGps(5m)Cps(5m)CpsGpslnApsln(5m)CpslnG-3' | 1433_16mer_3-10-3 | |

Example 4. Combination ASO Testing in HBsAg Release Assay Protocol

ASO combinations were tested in the HBsAg Release Assay Protocol described above in Example 2. Individual ASOs and a combination of the two ASOs were compared, and the reports are presented in Table 4. The $EC_{50}$ values are as follows: A: <0.2 nM, B: 0.2 nM-0.3 nM, C: 0.3-5 nM.

TABLE 4

HBsAg Assay for ASO Combinations

| ASO # | $EC_{50}$ nM | $CC_{50}$ nM | Position_length_structure |
|---|---|---|---|
| 8 | C | >10 | 1527_17mer_4-10-3 |
| 30 | C | >10 | 1431_17mer_4-9-4 |
| 50% ASO 8 + 50% ASO 30 | A | >10 | |

| ASO # | $EC_{50}$ nM | $CC_{50}$ nM | Position_length_structure |
|---|---|---|---|
| 8 | C | >10 | 1527_17mer_4-10-3 |
| 7 | B | >10 | 1432_16mer_4-9-3 |

TABLE 4-continued

HBsAg Assay for ASO Combinations

| | | | |
|---|---|---|---|
| 50% ASO 8 + 50% ASO 7 | A | >10 | |

| ASO # | $EC_{50}$ nM | $CC_{50}$ nM | Position_length_structure |
|---|---|---|---|
| 8 | C | >10 | 1527_17mer_4-10-3 |
| 9 | C | >10 | 1431_17mer_3-10-4 |
| 50% ASO 8 + 50% ASO 9 | A | >10 | |

| ASO # | $EC_{50}$ nM | $CC_{50}$ nM | Position_length_structure |
|---|---|---|---|
| 5 | A | >10 | 1582_16mer_4-9-3 |
| 7 | B | >10 | 1432_16mer_4-9-3 |
| 50% ASO 5 + 50% ASO 7 | B (lower than 7 alone) | >10 | |

| ASO # | EC50 nM | $CC_{50}$ nM | Position_length_structure |
|---|---|---|---|
| 40 | C | >10 | 246_17mer_3-10-4 |
| 1 | A | >10 | 1527_16mer_3-10-3 |

TABLE 4-continued

| HBsAg Assay for ASO Combinations | | |
|---|---|---|
| 50% ASO 40 + 50% ASO 1 | A (lower than 1 alone) | 10 |

Example 5. Modified ASO Testing in AAV-HBV Mouse Model with Point Modifications

ASOs with LNA and BNA chemistries were synthesized on ABI 394 and Expedite 8909 synthesizers using standard phosphoramidite chemistry. In vitro screening of LNA ASOs was carried out in HepG2.2.15 cells using HBsAg release assay. Potent LNA-containing ASOs were chosen for N-Acetylgalactosamine (GalNac) conjugation and tested at 3×10 mg/kg every 3 days in the adeno-associated virus (AAV)-HBV mouse model. BNA wing modifications were applied and compared to its all-LNA ASO. Table 5 shows HBsAg Nadir with 3×10 mg/kg QW compared to ASO 108. In these LNA-containing ASO in HBx region, targeting all HBV transcripts including HBx, a single replacement of a 5-methyl LNA C in the wing with 5-methyl spirocyclopropyl C improved the nadir for HBsAg by 0.5 $\text{Log}_{10}$ IU/ml while reducing serum alanine aminotransferase (ALT) by 3-fold.

TABLE 5

| | HBsAg Nadir | |
|---|---|---|
| ASO # | HBsAg Nadir with 3 × 10mg/kg QW | Max ALT with 3 × 10 mg/kg QW |
| 108A | 1 log drop | 611 U/L |
| 108B | 0.97 log drop | 629 U/L |
| 108C | 1.25 log drop | 488 U/L |
| 108D | 1.17 log drop | 272 U/L |
| 108E | 1.44 log drop | 243 U/L |

ASOs with LNA and gap-modified chemistries were synthesized on ABI 394 and Expedite 8909 synthesizers using standard phosphoramidite chemistry. In vitro screening of LNA ASOs was carried out in HepG2.2.15 cells using HBsAg release assay. Potent LNA-containing ASOs were chosen for N-Acetylgalactosamine (GalNac) conjugation and tested at 3×10 mg/kg every 3 days in the adeno-associated virus (AAV)-HBV mouse model. Nucleobase gap modifications were applied and compared to ASO 107. Table 6 shows HBsAg Nadir with 3×10 mg/kg QW compared to ASO 107. In these HBx region LNA ASO, a single replacement of deoxy-T in the gap with 2-thio T reduced serum ALT by 30-fold to normal levels while maintaining in vivo activity.

TABLE 6

| | HBsAg Nadir | |
|---|---|---|
| ASO # | HBsAg Nadir | Max ALT |
| 107A | 0.90 log drop | 596 U/L |
| 107B | 0.99 log drop | 168 U/L |
| 107C | 0.90 log drop | 29 U/L |
| 107D | 1.06 log drop | 380 U/L |
| 1xPBS | 0.1 log drop | 28 U/L |

Example 6. GalNac ASO Testing in AAV-HBV Mouse Model at 1×5 mg/kg Single Dose

ASOs were tested at 1×5 mg/kg in the adeno-associated virus (AAV)-HBV mouse model. This dosing regimen is mainly to rank order in vivo potency of ASOs. Although we could eliminate a small amount of very toxic ASOs in liver with ALT elevation in 1×5 mg/kg, majority of ASOs needs more stringent dosing regimen to be differentiated in liver tox. The resulting nadir $\log_{10}$ reduction in serum HBsAg and fold-change in ALT during the study are presented in Table 7, where A≥1 $\log_{10}$ reduction in HBsAg, B is 0.5-1 $\log_{10}$ reduction in HBsAg, and C is <0.5 $\log_{10}$ reduction in HBsAg, and X≤3-fold of ALT of vehicle control, which is considered normal, Y is 3-fold-30-fold of ALT of vehicle control, and Z is ≥30-fold of ALT of vehicle control. Both Y and Z are considered to be liver toxic.

The following specific sequences in Table 7 are within the scope of the present disclosure. As used herein, ln=Locked nucleic acid (LNA); lnA=Locked nucleic acid (LNA) A; ln(5m)C=ln(5m)C=Locked nucleic acid (LNA)-5methyl C; lnG=Locked nucleic acid (LNA) G; lnT=Locked nucleic acid (LNA) T; (5m)C=5 methylC; mA=2-O-methoxy A; mU=2-O-methoxy U; (8nh)A=8-amino A; (8nh)G=8-amino G; (2s)T=2-thio T; cp=scp=cyclopropyl; cpC=scpC=cyclopropyl C; cpG=scpG=cyclopropyl G; cpT=scpT=cyclopropyl T; ps=phosphorothioate linkages.

TABLE 7

| | | HBsAg Nadir (Log) and ALT for 1 × 5 mg/kg | | |
|---|---|---|---|---|
| SEQ ID NO. | ASO # | Sequence | HBsAg Nadir (Log) | ALT |
| 164 | 160 | 5'-GalNAc6-(PS)2-p-ClnGpslnApslnTpsTps(5m)CpsApsGps(5m)CpsGps(5m)Cps(5m)CpsGpsApsln(5m)CpslnGpslnGpslnG-3' | B | X |
| 165 | 161 | 5' GalNAc1-C6-NH-lnGpslnTpslnGpsApsApsGps(5m)CpsGpsApsApsGpsTpslnGpsln(5m)CpslnA 3' | B | X |
| 166 | 162 | 5' GalNAc1-C6-p-lnApslnGpsln(5m)CpsGpsApsApsGpsTpsGps(5m)CpsAps(5m)CpsApsln(5m)CpslnGpslnG 3' | B | X |
| 167 | 163 | 5' GalNAc3-(PS)2-p-lnGpslnTpslnGpsApsApsGps(5m)CpsGpsApsApsGpsTpslnGpsln(5m)CpslnA 3' | C | X |

TABLE 7-continued

HBsAg Nadir (Log) and ALT for 1 x 5 mg/kg

| SEQ ID NO. | ASO # | Sequence | HBsAg Nadir (Log) | ALT |
|---|---|---|---|---|
| 168 | 164 | 5' GalNAc1-C6-p-lnApslnApslnGpsln(5m)Cps GpsApsApsGpsTpsGps(5m)mCpsApsln(5m)Cpsln Apsln(5m)CpslnG 3' | B | X |
| 169 | 165 | 5' GalNAc1-C6-p-lnGpslnApslnTpslnTps(5m) CpsApsGps(5m)CpsGps(5m)Cps(5m)CpsGpsApsln (5m)CpslnGpslnG 3' | B | X |
| 170 | 166 | 5' GalNAc1-C6-p-ln(5m)CpslnGpsln(5m)CpsGps TpsApsApsApsGpsApsGpsApslnGpslnGpslnTpsln G 3' | B | X |
| 171 | 167 | 5' GalNAc1-C6-p-lnGpslnGpslnApslnTpsTps (5m)CpsApsGps(5m)CpsGps(5m)Cps(5m)CpslnGps lnApsln(5m)CpslnGpslnG 3 | C | X |
| 172 | 168 | 5' GalNAc3-(PS)2-p-lnGpslnApslnGpsGpsTps GpsApsApsGps(5m)CpsGpsApsApslnGpslnTpsln G 3' | B | Y |
| 173 | 169 | 5'-GalNAc3-(PS)2-p-ln(5m)Cpsln(5m)CpslnGps ln(5m)CpsGpsTpsApsApsApsGpsApsGpsApsGpsln GpslnTpslnG 3' | C | X |
| 174 | 170 | 5' GalNAc3-(PS)2-p-lnGpslnApslnTpsTps(5m) CpsApsGps(5m)CpsGps(5m)Cps(5m)CpsGpsApsln (5m)CpslnGpslnGpslnG 3' | A | X |
| 175 | 171 | 5'-GalNAc3-(PS)2-p-ln(5m)Cpsln(5m)CpslnAps (5m)Cps(5m)CpsAps(5m)CpsGpsApsGpsTps(5m) CpsTpslnApslnGpslnApsln(5m)C 3' | A | X |
| 176 | 172 | 5'-GalNAc3-(PS)2-p-lnApslnTpslnGpslnApsTps ApsApsApsAps(5m)CpsGps(5m)Cpsln(5m)Cpsln Gpsln(5m)CpslnApslnG 3' | C | X |
| 177 | 173 | 5'-GalNAc3-(PS)2-p-lnGpsln(5m)Cpsln(5m)C (5m)CpsTpsAps(5m)CpsGpsApsAps(5m)Cps(5m) CpsApslnCpslnTpslnGpslnA 3' | C | X |
| 178 | 174 | 5'-GalNAc3-(PS)2-p-lnApslnGpsln(5m)CpsGps ApsApsGpsTpsGps(5m)CpsAps(5m)CpsApsln(5m) CpslnGpslnG 3' | B | X |
| 179 | 175 | 5'-GalNAc3-(PS)2-p-ln(5m)CpslnGpsln(5m)Cps GpsGpsGpsApsTpsTps(5m)CpsApsGpsln(5m)Cpsln Gpsln(5m)C 3' | C | X |
| 180 | 176 | 5'-GalNAc3-(PS)2-p-lnGpsln(5m)CpslnGpsAps ApsGpsTpsGps(5m)CpsAps(5m)CpsAps(5m)Cpsln GpslnG 3' | B | X |
| 181 | 177 | 5'-GalNAc3-(PS)2-p-lnGpslnGpslnTpsGps(5m) CpsGps(5m)Cps(5m)Cps(5m)Cps(5m)CpsGpsTps GpslnGpslnG 3' | C | X |
| 182 | 178 | 5'-GalNAc3-(PS)2-p-lnGpslnGpslnTpsGpsAps ApsGps(5m)CpsGpsApsApsGpsTpslnGpsln(5m) C 3' | B | X |
| 183 | 179 | 5'-GalNAc3-(PS)2-p-lnGpslnGpslnApslnTpsTps (5m)CpsApsGps(5m)CpsGps(5m)Cps(5m)CpsGpsln Apsln(5m)CpslnGpslnG 3' | C | X |
| 184 | 180 | 5'-lnGpslnApslnGpsGpsTpsGpsApsApsGps(5m) CpsGpsApsApslnGpslnTpslnG-p-(PS)2-GalNAc3 3' | C | X |
| 185 | 181 | 5'-GalNAc3-(PS)2-p-lnApslnGpsln(5m)CpsGps ApsApsGpsTpsGps(5m)CpsAps(5m)CpsApsln(5m) CpslnG 3' | B | X |

TABLE 7-continued

HBsAg Nadir (Log) and ALT for 1 x 5 mg/kg

| SEQ ID NO. | ASO # | Sequence | HBsAg Nadir (Log) | ALT |
|---|---|---|---|---|
| 186 | 182 | 5'-GalNAc3-(PS)2-p-lnApslnGpslnGpsTpsGps ApsApsGps(5m)CpsGpsApsApsGpslnTpslnG 3' | A | Y |
| 187 | 183 | 5'-GalNAc5-(PS)2-p-lnGpsln(5m)CpslnGps(5m) Cps(5m)Cps(5m)Cps(5m)CpsGpsTpsGpsGpsTpsln (5m)CpslnGpslnG 3' | B | X |
| 188 | 184 | 5'-GalNAc5-(PS)2-p-lnApslnGpslnGpsTpsGps (5m)CpsGps(5m)Cps(5m)Cps(5m)Cps(5m)CpsGps lnTpslnGpslnG 3 | A | Y |
| 189 | 185 | 5'-GalNAc3-(PS)2-p-ln(5m)CpslnGpsln(5m)Cps GpsTpsApsApsApsGpsApsGpsApsGpslnGpslnTpsln G 3' | C | X |
| 190 | 186 | 5'-GalNAc3-(PS)2-p-ln(5m)CpslnGpsln(5m)Cps GpsTpsApsApsApsGpsApsGpsApsGpslnGpslnTpsln G 3' | C | X |
| 191 | 187 | 5'-GalNAc4-(PS)2-p-ln(5m)CpslnGpsln(5m)Cps GpsTpsApsApsApsGpsApsGpsApsGpslnGpslnTpsln G 3' | C | X |
| 192 | 188 | 5'-GalNAc4-(PS)2-p-lnGpslnApslnTpsTps(5m) CpsApsGps(5m)CpsGps(5m)Cps(5m)CpsGpsApsln (5m)CpslnGpslnGpslnG 3' | B | X |
| 193 | 189 | 5'-GalNAc3-(PS)2-p-lnApscpTpslnGpslnApsTps ApsApsApsAps(5m)CpsGps(5m)Cpsln(5m)Cpsln Gpsln(5m)CpslnApslnG 3' | C | X |
| 194 | 190 | 5'-GalNAc2-C6-p-CAlnApslnTpslnGpslnApsTps ApsApsApsAps(5m)CpsGps(5m)Cps(5m)CpslnGps ln(5m)CpslnApslnG 3' | C | X |
| 195 | 191 | 5'-GalNAc2-C6-p-CAlnApslnTpslnGpsApsTpsAps ApsApsAps(5m)CpsGps(5m)Cps(5m)CpslnGpsln (5m)CpslnApslnG 3' | C | X |
| 196 | 192 | 5'-GalNAc6-(PS)2-p-lnGpslnApslnTpsTps(5m) CpsApsGps(5m)CpsGps(5m)Cps(5m)CpsGpsApsln (5m)CpslnGpslnGpslnG 3' | A | X |
| 197 | 193 | 5'-GalNAc6-(PS)2-p-ln(5m)CpslnGpsln(5m)Cps GpsTpsApsApsApsGpsApsGpsApsGpslnGpslnTpsln G 3' | C | X |
| 198 | 194 | 5' GalNAc6-(PS)2-p-CAlnGpslnApslnTpsTps(5m) CpsApsGps(5m)CpsGps(5m)Cps(5m)CpsGpsApsln (5m)CpslnGpslnGpslnG 3' | B | X |
| 199 | 195 | 5'-lnGpslnApslnTpsTps(5m)CpsApsGps(5m)Cps Gps(5m)Cps(5m)CpsGpsApsln(5m)CpslnGpslnGps lnGC-p-(PS)2-GalNAc6-3' | A | X |
| 200 | 196 | 5' lnGpslnApslnTpsTps(5m)CpsApsGps(5m)Cps Gps(5m)Cps(5m)CpsGpsApsln(5m)CpslnGpslnGps lnGCA-p-(PS)2-GalNAc6-3' | A | X |
| 201 | 197 | 5' GalNAc4-(PS)2-p-ClnGpslnApslnTpsTps(5m) CpsApsGps(5m)CpsGps(5m)Cps(5m)CpsGpsApsln (5m)CpslnGpslnGpslnG-3' | B | X |
| 202 | 198 | 5'-GalNAc4-(PS)2-p-CAlnGpslnApslnTpsTps (5m)CpsApsGps(5m)CpsGps(5m)Cps(5m)CpsGps Apsln(5m)CpslnGpslnGpslnG-3' | B | X |
| 203 | 199 | 5' lnGpslnApslnTpsTps(5m)CpsApsGps(5m)Cps Gps(5m)Cps(5m)CpsGpsApsln(5m)CpslnGpslnGps lnGC-p-(PS)2-GalNAc4 3' | B | X |

TABLE 7-continued

HBsAg Nadir (Log) and ALT for 1 × 5 mg/kg

| SEQ ID NO. | ASO # | Sequence | HBsAg Nadir (Log) | ALT |
|---|---|---|---|---|
| 204 | 200 | 5' lnGpslnApslnTpsTps(5m)CpsApsGps(5m)Cps Gps(5m)Cps(5m)CpsGpsApsln(5m)CpslnGpslnGps lnGCA-p-(PS)2-GalNAc4 3' | A | X |
| 205 | 201 | 5' GalNAc6-(PS)2-p-ln(5m)Cpsln(5m)CpslnAps ln(5m)Cps(5m)CpsAps(5m)CpsGpsApsGpsTps(5m) CpsTpsApslnGpslnApsln(5m)C 3' | C | X |
| 206 | 202 | 5' GalNAc4-(PS)2-p-ln(5m)Cpsln(5m)CpslnAps ln(5m)Cps(5m)CpsAps(5m)CpsGpsApsGpsTps(5m) CpsTpsApslnGpslnApsln(5m)C 3' | A | X |
| 207 | 203 | 5'-GalNAc5-(PS)2-p-lnGpsln(5m)CpslnGpsAps ApsGpsTpsGps(5m)CpsAps(5m)CpsAps(5m)Cpscp GpslnG 3' | B | X |
| 208 | 204 | 5'-GalNAc5-(PS)2-p-lnGpsln(5m)CpscpGpsAps ApsGpsTpsGps(5m)CpsAps(5m)CpsAps(5m)Cpsln GpslnG 3' | B | X |
| 209 | 205 | 5'-GalNAc5-(PS)2-p-lnGpscp(5m)CpslnGpsAps ApsGpsTpsGps(5m)CpsAps(5m)CpsAps(5m)Cpsln GpslnG 3' | B | X |
| 210 | 206 | 5'-GalNAc5-(PS)2-p-cpGpsln(5m)CpslnGpsAps ApsGpsTpsGps(5m)CpsAps(5m)CpsAps(5m)Cpsln GpslnG 3' | B | X |
| 211 | 207 | 5'-GalNAc5-(PS)2-p-lnGpscp(5m)CpslnGpsAps ApsGpsTpsGps(5m)CpsAps(5m)CpsAps(5m)Cpscp GpslnG 3' | C | X |
| 212 | 208 | 5'-GalNAc5-(PS)2-p-lnGpsln(5m)CpscpGpsAps ApsGpsTpsGps(5m)CpsAps(5m)CpsAps(5m)Cpscp GpslnG 3' | C | X |
| 213 | 209 | 5'-GalNAc5-(PS)2-p-lnGpslnApslnTpsTps(5m) CpsApsGps(5m)CpsGps(5m)Cps(5m)CpsGpsApsln (5m)CpslnGpslnGpsAmG | A | X |
| 214 | 210 | 5'-GalNAc5-(PS)2-p-lnGpslnApslnTpsTps(5m) CpsApsGps(5m)CpsGps(5m)Cps(5m)CpsGpsApsln (5m)CpslnGpsAmGpslnG | A | X |
| 215 | 211 | 5'-GalNAc5-(PS)2-p-lnGpslnApslnTpsTps(5m) CpsApsGps(5m)CpsGps(5m)Cps(5m)CpsGpsApsln (5m)CpsAmGpslnGpslnG | B | X |
| 216 | 212 | 5'-GalNAc5-(PS)2-p-lnGpslnApslnTpsTps(5m) CpsApsGps(5m)CpsGps(5m)Cps(5m)CpsGpsApsam (5m)CpslnGpslnGpslnG | B | X |
| 217 | 213 | 5'-GalNAc5-(PS)2-p-lnGpslnApsamTpsTps(5m) CpsApsGps(5m)CpsGps(5m)Cps(5m)CpsGpsApsln (5m)CpslnGpslnGpslnG | A | X |
| 218 | 214 | 5'-GalNAc5-(PS)2-p-lnGpsAmApslnTpsTps(5m) CpsApsGps(5m)CpsGps(5m)Cps(5m)CpsGpsApsln (5m)CpslnGpslnGpslnG | B | X |
| 219 | 215 | 5'-GalNAc5-(PS)2-p-AmGpslnApslnTpsTps(5m) CpsApsGps(5m)CpsGps(5m)Cps(5m)CpsGpsApsln (5m)CpslnGpslnGpslnG | A | X |
| 220 | 216 | 5'-GalNAc2-C6-p-CAlnGpslnGpslnApslnTpsTps (5m)CpsApsGps(5m)CpsGps(5m)Cps(5m)CpsGps Apsln(5m)CpslnGpslnG 3' | C | X |
| 221 | 217 | 5'-GalNAc2-C6-p-CAlnApslnApslnGpsApsGpsAps GpsGpsTpsGps(5m)CpslnGpsln(5m)Cpsln(5m)Cps ln(5m)C 3' | B | X |

TABLE 7-continued

HBsAg Nadir (Log) and ALT for 1 × 5 mg/kg

| SEQ ID NO. | ASO # | Sequence | HBsAg Nadir (Log) | ALT |
|---|---|---|---|---|
| 222 | 218 | 5'-GalNAc5-(PS)2-p-lnGpslnApslnTpsTps(5m)CpsApsGps(5m)CpsGps(5m)Cps(5m)CpsGpsApsln(5m)CpslnGpslnGpscpG 3' | A | X |
| 223 | 219 | 5'-GalNAc5-(PS)2-p-lnGpslnApslnTpsTps(5m)CpsApsGps(5m)CpsGps(5m)Cps(5m)CpsGpsApsln(5m)CpscpGpslnGpslnG 3' | B | X |
| 224 | 220 | 5'-GalNAc5-(PS)2-p-lnGpslnApslnTpsTps(5m)CpsApsGps(5m)CpsGps(5m)Cps(5m)CpsGpsApscp(5m)CpslnGpslnGpslnG 3' | B | X |
| 225 | 221 | 5'-GalNAc5-(PS)2-p-lnGpslnApscpTpsTps(5m)CpsApsGps(5m)CpsGps(5m)Cps(5m)CpsGpsApsln(5m)CpslnGpslnGpslnG 3' | A | X |
| 226 | 222 | 5'-GalNAc5-(PS)2-p-lnGpscpApslnTpsTps(5m)CpsApsGps(5m)CpsGps(5m)Cps(5m)CpsGpsApsln(5m)CpslnGpslnGpslnG | B | X |
| 227 | 223 | 5'-GalNAc5-(PS)2-p-cpGpslnApslnTpsTps(5m)CpsApsGps(5m)CpsGps(5m)Cps(5m)CpsGpsApsln(5m)CpslnGpslnGpslnG 3' | B | X |
| 228 | 224 | 5'-GalNAc5-(PS)2-p-lnGpslnApscpTpsTps(5m)CpsApsGps(5m)CpsGps(5m)Cps(5m)CpsGpsApscp(5m)CpslnGpslnGpslnG 3' | A | X |
| 229 | 225 | 5'-GalNAc5-(PS)2-p-ln(5m)Cpsln(5m)CpslnAps ln(5m)Cps(5m)CpsAps(5m)CpsGpsApsGpsTps(5m)CpsTpsApslnGpslnApscp(5m)C | C | X |
| 230 | 226 | 5'-GalNAc5-(PS)2-p-ln(5m)Cpsln(5m)CpslnAps ln(5m)Cps(5m)CpsAps(5m)CpsGpsApsGpsTps(5m)CpsTpsApscpGpslnApsln(5m)C | B | X |
| 231 | 227 | 5'-GalNAc5-(PS)2-p-ln(5m)Cpscp(5m)CpslnAps ln(5m)Cps(5m)CpsAps(5m)CpsGpsApsGpsTps(5m)CpsTpsApslnGpslnApsln(5m)C | C | X |
| 232 | 228 | 5'-GalNAc5-(PS)2-p-cp(5m)Cpsln(5m)CpslnAps ln(5m)Cps(5m)CpsAps(5m)CpsGpsApsGpsTps(5m)CpsTpsApslnGpslnApsln(5m)C | C | X |
| 233 | 229 | lnGpsln(5m)CpslnGpsApsApsGpsTpsGps(5m)CpsAps(5m)CpsAps(5m)CpslnGpslnGA-p-(PS)2-GalNAc4-3' | B | X |
| 234 | 230 | 5'lnGpsln(5m)CpslnGpsApsApsGpsTpsGps(5m)CpsAps(5m)CpsAps(5m)CpslnGpslnG(5m)C-p-(PS)2-GalNAc4-3' | B | X |
| 235 | 231 | 5'lnGpsln(5m)CpslnGpsApsApsGpsTpsGps(5m)CpsAps(5m)CpsAps(5m)CpslnGpslnGG-p-(PS)2-GalNAc4-3' | C | X |
| 236 | 232 | 5'lnGpsln(5m)CpslnGpsApsApsGpsTpsGps(5m)CpsAps(5m)CpsAps(5m)CpslnGpslnGmA-p-(PS)2-GalNAc4-3' | C | X |
| 237 | 233 | 5'lnGpsln(5m)CpslnGpsApsApsGpsTpsGps(5m)CpsAps(5m)CpsAps(5m)CpslnGpslnGm(5m)C-p-(PS)2-GalNAc4 3' | C | X |
| 238 | 234 | 5'lnGpsln(5m)CpslnGpsApsApsGpsTpsGps(5m)CpsAps(5m)CpsAps(5m)CpslnGpslnGmG-p-(PS)2-GalNAc4 3' | C | X |
| 239 | 235 | 5'ln(5m)Cpsln(5m)CpslnApsln(5m)Cps(5m)CpsAps(5m)CpsGpsApsGpsTps(5m)CpsTpsApslnGpslnApsln(5m)CA-p-(PS)2-GalNAc4 3' | B | X |

TABLE 7-continued

HBsAg Nadir (Log) and ALT for 1 x 5 mg/kg

| SEQ ID NO. | ASO # | Sequence | HBsAg Nadir (Log) | ALT |
|---|---|---|---|---|
| 240 | 236 | 5'ln(5m)Cpsln(5m)CpslnApsln(5m)Cps(5m)Cps Aps(5m)CpsGpsApsGpsTps(5m)CpsTpsApslnGpsln Apsln(5m)C(5m)C-p-(PS)2-GalNAc4 3' | B | X |
| 241 | 237 | 5'ln(5m)Cpsln(5m)CpslnApsln(5m)Cps(5m)Cps Aps(5m)CpsGpsApsGpsTps(5m)CpsTpsApslnGpsln Apsln(5m)CG-p-(PS)2-GalNAc4 3' | B | X |
| 242 | 238 | 5'ln(5m)Cpsln(5m)CpslnApsln(5m)Cps(5m)Cps Aps(5m)CpsGpsApsGpsTps(5m)CpsTpsApslnGpsln Apsln(5m)CmA-p-(PS)2-GalNAc4 3' | B | X |
| 243 | 239 | 5'ln(5m)Cpsln(5m)CpslnApsln(5m)Cps(5m)Cps Aps(5m)CpsGpsApsGpsTps(5m)CpsTpsApslnGpsln Apsln(5m)-p-(PS)2-GalNAc4 3' | B | X |
| 244 | 240 | 5'lnGpslnApslnTpslnApslnApsApsAps(5m)Cps Gps(5m)Cps(5m)CpsGps(5m)CpslnApslnGpslnAps ln(5m)CT-p-(PS)2-GalNAc4 3' | B | X |
| 245 | 241 | 5'lnGpslnApslnTpslnApslnApsApsAps(5m)Cps Gps(5m)Cps(5m)CpsGps(5m)CpslnApslnGpslnAps ln(5m)C(5m)C-p-(PS)2-GalNAc4 3' | B | X |
| 246 | 242 | 5'lnGpslnApslnTpslnApslnApsApsAps(5m)Cps Gps(5m)Cps(5m)CpsGps(5m)CpslnApslnGpslnAps ln(5m)CG-p-(PS)2-GalNAc4 3' | B | X |
| 247 | 243 | 5'lnGpslnApslnTpslnApslnApsApsAps(5m)Cps Gps(5m)Cps(5m)CpsGps(5m)CpslnApslnGpslnAps ln(5m)CmU-p-(PS)2-GalNAc43' | B | X |
| 248 | 244 | 5'-lnGpslnApslnTpslnApslnApsApsAps(5m)Cps Gps(5m)Cps(5m)CpsGps(5m)CpslnApslnGpslnAps ln(5m)Cm(5m)C-p-(PS)2-GalNAc4 3' | C | X |
| 249 | 245 | 5'lnGpslnApslnTpslnApslnApsApsAps(5m)Cps Gps(5m)Cps(5m)CpsGps(5m)CpslnApslnGpslnAps ln(5m)CmG-p-(PS)2-GalNAc4 3' | B | X |
| 250 | 246 | 5'-GalNAc4-(PS)2-p-lnGpslnApslnTpslnApsln ApsApsAps(5m)CpsGps(5m)Cps(5m)CpsGps(5m) CpslnApslnGpslnApsln(5m)C | B | X |
| 251 | 247 | 5'lnGpslnGpslnTpsGpsApsApsGps(5m)CpsGps ApsApsGpslnTpslnGpsln(5m)CpslnAmU-p-(PS)2-GalNAc4 3' | B | X |
| 252 | 248 | lnGpsln(5m)CpslnGpsApsApsGpsTpsGps(5m)Cps Aps(5m)CpsAps(5m)CpslnGpslnGA-p-(PS)2-GalNAc6 3' | B | X |
| 253 | 249 | 5'-lnGpslnApslnTpslnApslnApsApsAps(5m)Cps Gps(5m)Cps(5m)CpsGps(5m)CpslnApslnGpslnAps ln(5m)CT-3' | B | X |
| 254 | 250 | 5'-GalNAc4-(PS)2-p-mUlnGpslnGpslnTpsGpsAps ApsGps(5m)CpsGpsApsApsGpslnTpslnGpsln(5m) CpslnA-3' | C | X |
| 255 | 251 | 5'-GalNAc4-(PS)2-p-TlnGpsln(5m)CpslnGpsAps ApsGpsTpsGps(5m)CpsAps(5m)CpsAps(5m)Cpsln GpslnG-3' | B | X |
| 256 | 252 | 5'-GalNAc4-(PS)2-p-mUlnGpsln(5m)CpslnGps ApsApsGpsTpsGps(5m)CpsAps(5m)CpsAps(5m)Cps lnGpslnG | B | X |
| 257 | 253 | 5'-GalNAc6-(PS)2-p-mUlnGpsln(5m)CpslnGps ApsApsGpsTpsGps(5m)CpsAps(5m)CpsAps(5m)Cps lnGpslnG | C | X |

TABLE 7-continued

HBsAg Nadir (Log) and ALT for 1 x 5 mg/kg

| SEQ ID NO. | ASO # | Sequence | HBsAg Nadir (Log) | ALT |
|---|---|---|---|---|
| 258 | 254 | 5'-GalNAc4-(PS)2-p-AlnGpslnApslnTpslnApsln ApsApsAps(5m)CpsGps(5m)Cps(5m)CpsGps(5m) CpslnApslnGpslnApsln(5m)C-3' | B | X |
| 259 | 255 | 5'-GalNAc6-(PS)2-p-AlnGpslnApslnTpslnApsln ApsApsAps(5m)CpsGps(5m)Cps(5m)CpsGps(5m) CpslnApslnGpslnApsln(5m)C-3' | B | X |
| 260 | 256 | 5'-GalNAc4-(PS)2-p-Aln(5m)Cpsln(5m)Cpsln Apsln(5m)Cps(5m)CpsAps(5m)CpsGpsAp sGpsTps(5m)CpsTpsApslnGpslnApsln(5m)C 3' | B | X |
| 261 | 257 | lnGpslnGpslnApsTpsTps(5m)CpsApsGps(5m)Cps Gps(5m)Cps(5m)CpsGpslnApsln(5m)CpslnGmA-p-(PS)2-GalNAc4 3' | B | X |
| 262 | 258 | 5'-lnGpslnApslnGpsApsGpsGpsTpsGps(5m)Cps Gps(5m)Cps(5m)Cps(5m)Cpsln(5m)CpslnGpsln TmA-p-(PS)2-GalNAc4 3' | B | X |
| 263 | 259 | 5'-GalNAc4-(PS)2-p-mUlnGpslnGpslnApsTpsTps (5m)CpsApsGps(5m)CpsGps(5m)Cps(5m)CpsGpsln Apsln(5m)CpslnG-3' | B | X |
| 264 | 260 | 5'-GalNAc4-(PS)2-p-mUlnGpslnApslnGpsApsGps GpsTpsGps(5m)CpsGps(5m)Cps(5m)Cps(5m)Cpsln (5m)CpslnGpslnT-3' | B | X |
| 265 | 261 | 5'-GalNAc4-(PS)2-p-mUlnGpslnApslnTpsTps (5m)CpsApsGps(5m)CpsGps(5m)Cps(5m)CpsGps Apsln(5m)CpslnGpslnGpslnG-3' | A | X |
| 266 | 262 | 5' lnGpslnApslnTpsTps(5m)CpsApsGps(5m)Cps Gps(5m)Cps(5m)CpsGpsApsln(5m)CpslnGpslnGps lnGmU-p-(PS)2-GalNAc4 3' | A | X |

Example 7. Modified ASO Testing in AAV-HBV Mouse Model at 3×10 mg/kg QW

ASOs were tested at 3×10 mg/kg every week in the adeno-associated virus (AAV)-HBV mouse model. This dosing regimen of 3×10 mg/kg QW is more stringent than 1×5 mg/kg shown in previous section. We can further select potent ASO with least ALT elevation. The resulting nadir $\log_{10}$ reduction in serum HBsAg and fold-change in ALT during the study are presented in Table 8, where A≥1 $\log_{10}$ reduction in HBsAg, B is 0.5-1 $\log_{10}$ reduction in HBsAg, and C is <0.5 $\log_{10}$ reduction in HBsAg, and X≤3-fold of ALT of vehicle control, which is considered normal. Y is 3-fold-30-fold of ALT of vehicle control, and Z is ≥30-fold of ALT of vehicle control. Both Y and Z are considered to show liver toxicity with Z being more severe.

The following specific sequences in Table 8 are within the scope of the present disclosure. As used herein, ln=Locked nucleic acid (LNA); lnA=Locked nucleic acid (LNA) A; =ln(5m)C=Locked nucleic acid (LNA)-5methyl C; lnG=Locked nucleic acid (LNA) G; lnT=Locked nucleic acid (LNA) T; (5m)C=5 methylC; mA=2-O-methoxy A; mU=2-O-methoxy U; (8nh)A=8-amino A; (8nh)G=8-amino G; (2s)T=2-thio T; cp=scp=cyclopropyl; cpC=scpC=cyclopropyl C; cpG=scpG=cyclopropyl G; cpT=scpT=cyclopropyl T; ps=phosphorothioate linkages; p=phosphodiester linkage.

TABLE 8

HBsAg Nadir (Log) and ALT for 3 x 10 mg/kg QW

| SEQ ID NO | ASO # | Sequence | HBsAg Nadir (Log) | ALT |
|---|---|---|---|---|
| 267 | 263 | 5'-GalNAc1-C6-p-CpsApslnGpslnApslnTpsln Tps(5m)CpsApsGps(5m)CpsGps(5m)Cps(5m)Cps GpsApsln(5m)CpslnGpslnG 3' | A | X |
| 268 | 264 | 5'-GalNAc1-C6-p-CpsApslnGpslnTpslnGpsAps ApsGps(5m)CpsGpsApsGpsTpslnGpsln(5m)Cps lnA 3' | A | Y |

TABLE 8-continued

HBsAg Nadir (Log) and ALT for 3 × 10 mg/kg QW

| SEQ ID NO | ASO # | Sequence | HBsAg Nadir (Log) | ALT |
|---|---|---|---|---|
| 269 | 265 | 5'-GalNAc2-C6-p-CAlnGpslnApslnTpsTps(5m) CpsApsGps(5m)CpsGps(5m)Cps(5m)CpsGpsAps ln(5m)CpslnGpslnGpslnG 3' | A | Y |
| 270 | 147 | 5'-GalNAc2-C6-p-CAlnApslnGpsln(5m)CpsGps ApsApsGpsTpsGps(5m)CpsAps(5m)CpsApsln(5m) CpslnGpslnG-3 | A | Y |
| 271 | 266 | 5'-GalNAc2-C6-p-CAlnApsln(5m)CpslnGpsln (5m)Cps(5m)CpsGps(5m)CpsApsGpsAps(5m)Cps Apsln(5m)CpslnApslnT-3' | A | Z |
| 425 | 132B | 5'-GalNAc2-C6-p-CAlnGpslnApslnGpsApsGps GpsTpsGps(5m)CpsGps(5m)Cps(5m)Cps(5m)Cps ln(5m)CpslnGpslnT 3' | A | Y |
| 426 | 267A | 5'-GalNAc2-C6-p-CAlnGpslnGpslnApsTpsTps (5m)CpsApsGps(5m)CpsGps(5m)Cps(5m)CpsGps lnApsln(5m)CpslnG 3' | A | Y |
| 274 | 268 | 5'-GalNAc2-C6-p-CAln(5m)Cpsln(5m)Cpsln Gps(5m)Cps(5m)CpsTpsGpsTpsApsAps(5m)Cps Apsln(5m)CpslnGpslnApslnG 3' | A | Z |
| 275 | 269 | 5'-GalNAc2-C6-p-CAln(5m)Cpsln(5m)Cpsln Gps(5m)Cps(5m)CpsTpsGpsTpsApsAps(5m) CpsApsln(5m)CpslnGpslnApslnG 3' | A | Z |
| 276 | 270 | 5'-GalNAc2-C6-p-CAlnGpslnApslnTpslnApsln ApsApsAps(5m)CpsGps(5m)Cps(5m)CpsGps(5m) CpslnApslnGpslnApsln(5m)C 3' | A | X |
| 277 | 271 | 5'-GalNAc2-C6-p-CAln(5m)CpslnApsln(5m) Cpsln(5m)CpsAps(5m)CpsGpsApsGpsTps(5m) CpsTpsApsGpslnApsln(5m)CpslnT 3' | A | Z |
| 278 | 272 | 5'-GalNAc2-C6-p-CAlnApslnTpslnGpslnAps TpsApsApsApsAps(5m)CpsGps(5m)Cps(5m)Cps Gpsln(5m)CpslnApslnG 3' | B | X |
| 427 | 273A | 5'-GalNAc2-C6-p-CAln(5m)Cpsln(5m)Cpsln Apsln(5m)Cps(5m)CpsAps(5m)CpsGpsApsGps Tps(5m)CpsTpsApslnGpslnApsln(5m)C 3' | A | Y |
| 280 | 274 | 5'-GalNAc2-C6-p-CAlnGpsln(5m)Cpsln(5m) Cpsln(5m)CpsTpsAps(5m)CpsGpsApsAps(5m) Cps(5m)CpsApsln(5m)CpslnTpslnGpslnA 3' | B | X |
| 281 | 275 | 5'-GalNAc2-C6-p-CAlnApslnApslnApsln(5m) CpsGps(5m)Cps(5m)CpsGps(5m)CpsApsGpsAps ln(5m)CpslnAln(5m)CpslnApslnT 3' | A | Z |
| 282 | 276 | 5'-GalNAc2-C6-p-CAlnApslnGpslnGpslnTps GpsApsApsGps(5m)CpsGpsApsApsGpslnTpsln Gpsln(5m)C 3' | A | Y |
| 283 | 277 | 5'-GalNAc2-C6-p-CAlnGpslnGpslnTpsGpsAps ApsGps(5m)CpsGpsApsApsGpslnTpslnGpsln(5m) CpslnA 3' | A | X |
| 284 | 151 | 5'-GalNAc6-(PS)2-p-lnGpslnGpslnApsTpsTps (5m)CpsApsGps(5m)CpsGps(5m)Cps(5m)CpsGps lnApsln(5m)CpslnG-3' | B | Y |
| 205 | 201 | 5'-GalNAc6-(PS)2-p-ln(5m)Cpsln(5m)Cpsln Apsln(5m)Cps(5m)CpsAps(5m)CpsGpsApsGps Tps(5m)CpsTpsApslnGpslnApsln(5m)C 3' | B | X |
| 285 | 279 | 5'-GalNAc2-C6-p-CAlnGpsln(5m)CpslnGpsAps ApsGpsTpsGps(5m)CpsApsCpsAps(5m)CpslnGps lnG 3' | A | X |

TABLE 8-continued

HBsAg Nadir (Log) and ALT for 3 x 10 mg/kg QW

| SEQ ID NO | ASO # | Sequence | HBsAg Nadir (Log) | ALT |
|---|---|---|---|---|
| 286 | 152 | 5'-GalNAc6-(PS)2-p-lnGpslnGpslnAps(2s) TpsTps(5m)CpsApsGps(5m)CpsGps(5m)Cps(5m) CpsGpslnApsln(5m)CpslnG-3' | B | Y |
| 287 | 153 | 5'-GalNAc6-(PS)2-p-lnGpslnGpslnApsTps (2s)Tps(5m)CpsApsGps(5m)CpsGps(5m)Cps(5m) CpsGpslnApsln(5m)CpslnG-3' | A | X |
| 288 | 154 | 5'-GalNAc6-(PS)2-p-lnGpslnGpslnApsTpsTps (5oh)CpsApsGps(5m)CpsGps(5m)Cps(5m)Cps GpslnApsln(5m)CpslnG-3' | A | Y |
| 289 | 280 | 5'-GalNAc6-(PS)2-p-lnGpslnApslnTpsTps(5m) CpsApsGps(5m)CpsGps(5m)Cps(5m)CpsGpsAps ln(5m)CpslnGpslnGpslnG-3' | A | Y |
| 290 | 281 | 5'-GalNAc6-(PS)2-p-lnGpslnApslnTps(2s) Tps(5m)CpsApsGps(5m)CpsGps(5m)Cps(5m)Cps GpsApsln(5m)CpslnGpslnGpslnG-3' | A | X |
| 291 | 282 | 5'-GalNAc6-(PS)2-p-ln(5m)Cpsln(5m)Cpsln Apsln(5m)Cps(5oh)CpsAps(5m)CpsGpsApsGps Tps(5m)CpsTpsApslnGpslnApsln(5m)C-3' | A | X |
| 292 | 283 | 5'-GalNAc6-(PS)2-p-ln(5m)Cpsln(5m)Cpsln Apsln(5m)Cps(5m)CpsAps(5oh)CpsGpsApsGps Tps(5m)CpsTpsApslnGpslnApsln(5m)C-3' | B | X |
| 293 | 284 | ln(5m)Cpsln(5m)CpslnApsln(5m)Cps(5m)Cps Aps(5m)CpsGpsApsGpsTps(5m)Cps(2s)TpsAps lnGpslnApsln(5m)C-3' | B | X |
| 294 | 285 | 5'-GalNAc2-C6-p-CApslnApslnGpsln(5m)Cps GpsApsApsGpsTpsGps(5m)CpsAps(5m)CpsApsln (5m)CpslnG-3' | A | Y |
| 295 | 286 | 5'-lnGpslnApslnTpslnApslnApsApsAps(5m) CpsGps(5m)Cps(5m)CpsGps(5m)CpslnApslnGps lnApsln(5m)C-3' | A | X |
| 296 | 287 | 5'-GalNAc5-(PS)2-p-lnGpslnApslnTpslnAps lnApsApsAps(5m)CpsGps(5m)Cps(5m)CpsGps (5m)CpslnApslnGpslnApscp(5m)C-3' | A | X |
| 297 | 288 | 5'-lnGpslnApscpTpslnApslnApsApsAps(5m) CpsGps(5m)Cps(5m)CpsGps(5m)CpslnApsln GpslnApsln(5m)C-3' | A | X |
| 298 | 289 | 5'-GalNAc5-(PS)2-p-lnGpslnGpslnApsTpsTps (5m)CpsApsGps(5m)CpsGps(5m)Cps(5m)CpsGps lnApsln(5m)CpslnG-3' | A | Z |
| 299 | 290 | 5'-lnGpslnGpslnApsTpsTps(5m)CpsApsGps (5m)CpsGps(5m)Cps(5m)CpsGpslnApscp(5m) CpslnG-3' | A | Z |
| 300 | 136 | 5'-GalNAc5-(PS)2-p-lnGpslnApslnGpsApsGps GpsTpsGps(5m)CpsGps(5m)Cps(5m)Cps(5m)Cps ln(5m)CpslnGpscpT-3' | A | Y |
| 301 | 137 | 5'-lnGpslnApslnGpsApsGpsGpsTpsGps(5m)Cps Gps(5m)Cps(5m)Cps(5m)Cpscp(5m)CpslnGpsln T-3' | A | Y |
| 302 | 133 | 5'-GalNAc5-(PS)2-p-lnGpslnApslnGpsApsGps GpsTpsGps(5m)CpsGps(5m)Cps(5m)Cps(5m)Cps ln(5m)CpslnGpslnT-3' | A | Y |
| 303 | 134 | 5'-GalNAc5-(PS)2-p-lnGpslnApslnGpsApsGps GpsTpsGps(5m)CpsGps(5m)Cps(5m)Cps(5m)Cps ln(5m)CpslnGpsamT-3' | B | Y |

TABLE 8-continued

HBsAg Nadir (Log) and ALT for 3 x 10 mg/kg QW

| SEQ ID NO | ASO # | Sequence | HBsAg Nadir (Log) | ALT |
|---|---|---|---|---|
| 304 | 135 | 5'-GalNAc5-(PS)2-p-lnGpslnApslnGpsApsGps GpsTpsGps(5m)CpsGps(5m)Cps(5m)Cps(5m)Cps am(5m)CpslnGpslnT-3' | A | Y |
| 305 | 291 | 5'-GalNAc2-C6-p-CAlnApslnGpslnApsGpsAps GpsGpsTpsGps(5m)CpsGps(5m)Cps(5m)Cpsln CpslnCpslnGpslnT-3' | A | Y |
| 306 | 292 | 5'-GalNAc2-C6-p-CAlnApsln(5m)CpslnApsln ApsApsGpsGpsAps(5m)CpsGpsTps(5m)Cps(5m) Cps(5m)CpslnGpsln(5m)CpslnG-3' | A | X |
| 307 | 293 | 5'-GalNAc2-C6-p-CAlnApslnTpslnGpslnAps TpsApsApsApsAps(5m)CpsGps(5m)Cpsln(5m) CpslnGpsln(5m)CpslnApslnG-3' | B | X |
| 308 | 294 | 5'-GalNAc2-C6-p-CAln(5m)Cpsln(5m)Cpsln Gpsln(5m)CpsGpsTpsApsApsApsGpsApsGpsAps GpslnGpslnTpslnG-3' | B | X |

Example 8. Modified ASO Testing in AAV-HBV Mouse Model with 3×10 mg/kg Q3D

ASOs were tested at 3×10 mg/kg every 3 days in the adeno-associated virus (AAV)-HBV mouse model. The dosing regimen of 3×10 mg/kg Q3D is more stringent than 3×10 mg/kg QW and can further select ASOs with best therapeutic indexes. The resulting nadir $\log_{10}$ reduction in serum HBsAg and fold-change in ALT during the study are presented in Table 9, where A≥1 $\log_{10}$ reduction in HBsAg, B is 0.5-1 $\log_{10}$ reduction in HBsAg, and C is <0.5 $\log_{10}$ reduction in HBsAg, and X≤3-fold of ALT of vehicle control, which is considered normal. Y is 3-fold-30-fold of ALT of vehicle control, and Z is ≥30-fold of ALT of vehicle control. Both Y and Z are considered to be liver toxic with Z being more severe.

The following specific sequences in Table 9 are within the scope of the present disclosure. As used herein, ln=Locked nucleic acid (LNA); lnA=Locked nucleic acid (LNA) A; ln(5m)C=ln(5m)C=Locked nucleic acid (LNA)-5methyl C; lnG=Locked nucleic acid (LNA) G; lnT=Locked nucleic acid (LNA) T; (5m)C=5 methylC; mA=2-O-methoxy A; mU=2-O-methoxy U; (8nh)A=8-amino A; (8nh)G=8-amino G; (2s)T=2-thio T; cp=scp=cyclopropyl; cpC=scpC=cyclopropyl C; cpG=scpG=cyclopropyl G; cpT=scpT=cyclopropyl T; ps=phosphorothioate linkages. The "Position in HBV Genome" describes the 5'-end of target-site in acc. KC315400.1 (genotype B), which corresponds to SEQ ID NO: 1.

TABLE 9

HBsAg Nadir (Log) and ALT for 3 x 10 mg/kg Q3D

| SEQ ID No. | ASO # | Sequence | HBsAg Nadir (Log) | ALT |
|---|---|---|---|---|
| 270 | 147 | 5' GalNAc2-C6-p-CAlnApslnGpsln(5m)Cps GpsApsApsGpsTpsGps(5m)CpsAps(5m)CpsAps ln(5m)CpslnGpslnG 3' | B | Z |
| 309 | 295 | 5' GalNAc6-(PS)2-p-lnGpslnApslnTpsTps (5oh)CpsApsGps(5m)CpsGps(5m)Cps(5m)Cps GpsApsln(5m)CpslnGpslnGpslnG 3' | B | X |
| 244 | 240 | 5' lnGpslnApslnTpslnApslnApsApsAps(5m) CpsGps(5m)Cps(5m)CpsGps(5m)CpslnApsln GpslnApsln(5m)CT-p-(PS)2-GalNAc4 3' | B | X |
| 310 | 297 | 5' lnGpslnApslnTpslnApslnApsApsAps(5m) CpsGps(5m)Cps(5m)CpsGps(5m)CpslnApsln GpslnApscp(5m)CT-p-(PS)2-GalNAc4 3' | B | X |
| 311 | 298 | 5' lnGpsln(5m)CpscpGpsApsApsGpsTpsGps (5m)CpsAps(5m)CpsAps(5m)CpslnGpslnGA-p-(PS)2-GalNAc4-p-(PS)2-GalNAc4 3' | B | X |
| 312 | 299 | 5' lnGpscp(5m)CpslnGpsApsApsGpsTpsGps (5m)CpsAps(5m)CpsAps(5m)CpslnGpslnGA-p-(PS)2-GalNAc4 | B | X |

TABLE 9-continued

HBsAg Nadir (Log) and ALT for 3 × 10 mg/kg Q3D

| SEQ ID No. | ASO # | Sequence | HBsAg Nadir (Log) | ALT |
|---|---|---|---|---|
| 313 | 300 | 5' cpGpsln(5m)CpslnGpsApsApsGpsTpsGps(5m)CpsAps(5m)CpsAps(5m)CpslnGpslnGA-p-(PS)2-GalNAc4 3' | B | X |
| 314 | 301 | 5' lnGpsln(5m)CpslnGpsApsApsGpsTpsGps(5m)CpsAps(5m)CpsAps(5m)CpslnGpscpGA 3' | B | X |
| 315 | 302 | 5' lnGpsln(5m)CpslnGpsApsApsGpsTpsGps(5m)CpsAps(5m)CpsAps(5m)CpscpGpslnGA-p-(PS)2-GalNAc4 3' | B | X |
| 316 | 303 | 5' lnGpslnApslnTpslnApslnApsApsAps(5m)CpsGps(5m)Cps(5m)CpsGps(5m)CpslnApslnGpscpApsln(5m)CT-p-(PS)2-GalNAc4 3' | B | X |
| 317 | 304 | 5' lnGpslnApslnTpslnApslnApsApsAps(5m)CpsGps(5m)Cps(5m)CpsGps(5m)CpscpApslnGpslnApsln(5m)CT-p-(PS)2-GalNAc4 3' | B | X |
| 318 | 305 | 5' lnGpslnApslnTpslnApscpApsApsAps(5m)CpsGps(5m)Cps(5m)CpsGps(5m)CpslnApslnGpslnApsln(5m)CT-p-(PS)2-GalNAc4 3' | B | X |
| 319 | 306 | 5' lnGpslnApscpTpslnApslnApsApsAps(5m)CpsGps(5m)Cps(5m)CpsGps(5m)CpslnApslnGpslnApsln(5m)CT-p-(PS)2-GalNAc4 3' | B | X |
| 320 | 307 | 5' lnGpsln(5m)CpsamGpsApsApsGpsTpsGps(5m)CpsAps(5m)CpsAps(5m)CpslnGpslnGA-p-(PS)2-GalNAc4 3' | B | X |
| 321 | 308 | 5' lnGpsam(5m)CpslnGpsApsApsGpsTpsGps(5m)CpsAps(5m)CpsAps(5m)CpslnGpslnGA-p-(PS)2-GalNAc4 3' | B | X |
| 322 | 309 | 5' lnGpsln(5m)CpslnGpsApsApsGpsTpsGps(5m)CpsAps(5m)CpsAps(5m)CpslnGpsamGA-p-(PS)2-GalNAc4 3' | B | X |
| 323 | 310 | 5' lnGpsln(5m)CpslnGpsApsApsGpsTpsGps(5m)CpsAps(5m)CpsAps(5m)CpsamGpslnGA-p-(PS)2-GalNAc4 3' | B | X |
| 324 | 311 | 5' amGpsln(5m)CpslnGpsApsApsGpsTpsGps(5m)CpsAps(5m)CpsAps(5m)CpslnGpslnGA-p-(PS)2-GalNAc4 3' | B | X |
| 325 | 312 | 5' lnGpslnApslnTpslnApslnApsApsAps(5m)CpsGps(5m)Cps(5m)CpsGps(5m)CpslnApslnGpslnApsam(5m)CT-p-(PS)2-GalNAc4 3' | B | X |
| 326 | 313 | 5' lnGpslnApsamTpslnApslnApsApsAps(5m)CpsGps(5m)Cps(5m)CpsGps(5m)CpslnApslnGpslnApsln(5m)CT-p-(PS)2-GalNAc4 3' | B | X |
| 327 | 314 | 5' amGpslnApslnTpslnApslnApsApsAps(5m)CpsGps(5m)Cps(5m)CpsGps(5m)CpslnApslnGpslnApsln(5m)CT-p-(PS)2-GalNAc4 3' | B | X |
| 328 | 315 | 5' lnGpsamApslnTpslnApslnApsApsAps(5m)CpsGps(5m)Cps(5m)CpsGps(5m)CpslnApslnGpslnApsln(5m)CT-p-(PS)2-GalNAc4 3' | B | X |
| 329 | 316 | 5' lnGpslnApslnTpslnApslnApsApsAps(5m)CpsGps(5m)Cps(5m)CpsGps(5m)CpslnApscpGpslnApsln(5m)CT-p-(PS)2-GalNAc4 3' | B | X |
| 330 | 317 | 5' ln(5m)Cpsln(5m)CpslnApsln(5m)Cps(5m)CpsAps(5m)CpsGpsApsgpsTps(5m)CpsTpsApslnGpslnApscp(5m)CA-p-(PS)2-GalNAc4 3' | B | Y |

TABLE 9-continued

HBsAg Nadir (Log) and ALT for 3 x 10 mg/kg Q3D

| SEQ ID No. | ASO # | Sequence | HBsAg Nadir (Log) | ALT |
|---|---|---|---|---|
| 331 | 318 | 5' ln(5m)Cpsln(5m)CpslnApsln(5m)Cps(5m)CpsAps(5m)CpsGpsApsGpsTps(5m)CpsTpsApscpGpslnApsln(5m)CA-p-(PS)2-GalNAc4 3' | B | Y |
| 332 | 319 | 5' ln(5m)Cpsln(5m)CpslnApscp(5m)Cps(5m)CpsAps(5m)CpsGpsApsGpsTps(5m)CpsTpsApslnGpslnApsln(5m)CA-p-(PS)2-GalNAc4 3' | B | Y |
| 333 | 320 | 5' ln(5m)Cpscp(5m)CpslnApsln(5m)Cps(5m)CpsAps(5m)CpsGpsApsGpsTps(5m)CpsTpsApslnGpslnApsln(5m)CA-p-(PS)2-GalNAc4 3' | B | Y |
| 334 | 321 | 5' cp(5m)Cpsln(5m)CpslnApsln(5m)Cps(5m)CpsAps(5m)CpsGpsApsGpsTps(5m)CpsTpsApslnGpslnApsln(5m)CA-p-(PS)2-GalNAc4 3' | B | Y |
| 335 | 322 | 5' lnGpslnApslnTpslnApslnAps(8nh)ApsAps(5m)CpsGps(5m)Cps(5m)CpsGps(5m)CpslnApslnGpslnApscp(5m)CT-p-(PS)2-GalNAc4 3' | B | X |
| 336 | 323 | 5' lnGpscp(5m)CpslnGpsAps(8nh)ApsGpsTpsGps(5m)CpsAps(5m)CpsAps(5m)CpslnGpslnGA-p-(PS)2-GalNAc4 3' | B | X |
| 337 | 324 | 5' cpGpslnApslnTpslnApslnApsApsAps(5m)CpsGps(5m)Cps(5m)CpsGps(5m)CpslnApslnGpslnApsln(5m)CT-p-(PS)2-GalNAc4 3' | B | X |
| 338 | 325 | 5' lnGpslnGpslnTpsGpsApsApsGps(5m)CpsGpsApsApsGpslnTpslnGpscp(5m)CpslnAA-p-(PS)2-GalNAc4 3' | B | X |
| 339 | 326 | 5' lnGpslnGpslnTpsGpsApsApsGps(5m)CpsGpsApsApsGpslnTpscpGpsln(5m)CpslnAA-p-(PS)2-GalNAc4 3' | B | X |
| 340 | 327 | 5' lnGpslnGpslnTpsGpsApsApsGps(5m)CpsGpsApsApsGpscpTpslnGpsln(5m)CpslnAA-p-(PS)2-GalNAc4 3' | B | X |
| 341 | 328 | 5' lnGpslnGpscpTpsGpsApsApsGps(5m)CpsGpsApsApsGpslnTpslnGpsln(5m)CpslnAA | B | X |
| 342 | 329 | 5' lnGpscpGpslnTpsGpsApsApsGps(5m)CpsGpsApsApsGpslnTpslnGpsln(5m)CpslnAA-p-(PS)2-GalNAc4 3' | B | X |
| 343 | 330 | 5' cpGpslnGpslnTpsGpsApsApsGps(5m)CpsGpsApsApsGpslnTpslnGpsln(5m)CpslnAA-p-(PS)2-GalNAc4 3' | B | X |
| 344 | 331 | 5' lnGpslnApslnTpscpApslnApsApsAps(5m)CpsGps(5m)Cps(5m)CpsGps(5m)CpslnApslnGpslnApsln(5m)CT-p-(PS)2-GalNAc4 3' | B | X |
| 345 | 332 | 5' lnGpscpApslnTpslnApslnApsApsAps(5m)CpsGps(5m)Cps(5m)CpsGps(5m)CpslnApslnGpslnApsln(5m)CT-p-(PS)2-GalNAc4 3' | B | Z |
| 346 | 333 | 5' ln(5m)Cpsln(5m)CpslnApsln(5m)Cps(5m)CpsAps(5m)CpsGpsApsGpsTps(5m)CpsTpsApslnGpscpApsln(5m)CA-p-(PS)2-GalNAc4 3' | B | Y |
| 347 | 334 | 5' ln(5m)Cpsln(5m)CpscpApsln(5m)Cps(5m)CpsAps(5m)CpsGpsApsGpsTps(5m)CpsTpsApslnGpslnApsln(5m)CA-p-(PS)2-GalNAc4 3' | B | Y |
| 348 | 335 | 5' cp(5m)Cpscp(5m)CpscpApscp(5m)Cps(5m)CpsAps(5m)CpsGpsApsGpsTps(5m)CpsTpsApscpGpscpApscp(5m)CA-p-(PS)2-GalNAc4 3' | B | X |

TABLE 9-continued

HBsAg Nadir (Log) and ALT for 3 x 10 mg/kg Q3D

| SEQ ID No. | ASO # | Sequence | HBsAg Nadir (Log) | ALT |
|---|---|---|---|---|
| 349 | 336 | 5' lnGpslnApslnTpslnApslnApsApsAps(5m)CpsGps(5m)Cps(5m)CpsGps(5m)CpsamApslnGpslnApsln(5m)CT-p-(PS)2-GalNAc4 3' | B | X |
| 350 | 337 | 5' lnGpslnApslnTpslnApslnApsApsAps(5m)CpsGps(5m)Cps(5m)CpsGps(5m)CpslnApsamGpslnApsln(5m)CT-p-(PS)2-GalNAc4 3' | B | X |
| 351 | 338 | 5' lnGpslnApslnTpslnApsamApsApsAps(5m)CpsGps(5m)Cps(5m)CpsGps(5m)CpslnApslnGpslnApsln(5m)CT-p-(PS)2-GalNAc4 3' | B | X |
| 352 | 339 | 5' lnGpslnGpslnTpsGpsApsApsGps(5m)CpsGpsApsApsGpslnTpslnGpsln(5m)CpscpAA | B | X |
| 353 | 340 | 5' lnGpslnApslnTpsamApslnApsApsAps(5m)CpsGps(5m)Cps(5m)CpsGps(5m)CpslnApslnGpslnApsln(5m)CT-p-(PS)2-GalNAc4 3' | B | X |
| 354 | 341 | 5' lnGpslnApslnTpslnApslnApsApsAps(5m)CpsGps(5m)Cps(5m)CpsGps(5m)CpslnApslnGpsamApsln(5m)CT-p-(PS)2-GalNAc4 3' | B | X |
| 355 | 342 | 5' lnGpslnGpslnTpsGpsApsApsGps(5m)CpsGpsApsApsGpslnTpslnGpsam(5m)CpslnAA-p-(PS)2-GalNAc4 3' | B | X |
| 356 | 343 | 5' lnGpslnGpslnTpsGpsApsApsGps(5m)CpsGpsApsApsGpslnTpsamGpsln(5m)CpslnAA-p-(PS)2-GalNAc4 3' | B | X |
| 357 | 344 | 5' lnGpslnGpslnTpsGpsApsApsGps(5m)CpsGpsApsApsGpsamTpslnGpsln(5m)CpslnAA-p-(PS)2-GalNAc4 3' | B | X |
| 358 | 345 | 5' lnGpslnGpsamTpsGpsApsApsGps(5m)CpsGpsApsApsGpslnTpslnGpsln(5m)CpslnAA-p-(PS)2-GalNAc4 3' | B | X |
| 359 | 346 | 5' lnGpslnGpslnApsTpsTps(5m)CpsApsGps(5m)CpsGps(5m)Cps(5m)CpsGpslnApsln(5m)CpscpGA-p-(PS)2-GalNAc4 3' | B | Z |
| 360 | 347 | 5' lnGpslnGpslnAps(2s)TpsTps(5m)CpsApsGps(5m)CpsGps(5m)Cps(5m)CpsGpslnApscp(5m)CpslnGA-p-(PS)2-GalNAc4 3' | B | Z |
| 361 | 348 | 5' lnGpslnGpslnApsTpsTps(5m)CpsApsGps(5m)CpsGps(5m)Cps(5m)CpsGpscpApsln(5m)CpslnGA-p-(PS)2-GalNAc4 3' | B | Z |
| 362 | 349 | 5' lnGpslnGpscpApsTpsTps(5m)CpsApsGps(5m)CpsGps(5m)Cps(5m)CpsGpslnApsln(5m)CpslnGA-p-(PS)2-GalNAc4 3' | B | Z |
| 363 | 350 | 5' lnGpscpGpslnApsTpsTps(5m)CpsApsGps(5m)CpsGps(5m)Cps(5m)CpsGpslnApsln(5m)CpslnGA-p-(PS)2-GalNAc4 3' | B | Z |
| 364 | 351 | 5' cpGpslnGpslnApsTpsTps(5m)CpsApsGps(5m)CpsGps(5m)Cps(5m)CpsGpslnApsln(5m)CpslnGA-p-(PS)2-GalNAc4 3' | B | Z |
| 365 | 352 | 5' lnGpslnApslnGpsAps(8nh)GpsGpsTpsGps(5m)CpsGps(5m)Cps(5m)Cps(5m)Cpscp(5m)CpslnGpslnTA-p-(PS)2-GalNAc4 3' | B | Y |
| 366 | 353 | 5' lnGpslnApscpTpsTps(5oh)CpsApsGps(5m)CpsGps(5m)Cps(5m)CpsGpsApsln(5m)CpslnGpslnGpslnGT-p-(PS)2-GalNAc4 3' | B | Y |

TABLE 9-continued

HBsAg Nadir (Log) and ALT for 3 × 10 mg/kg Q3D

| SEQ ID No. | ASO # | Sequence | HBsAg Nadir (Log) | ALT |
|---|---|---|---|---|
| 367 | 354 | 5' lnGpslnApslnGps(8nh)ApsGpsGpsTpsGps(5m)CpsGps(5m)Cps(5m)Cps(5m)Cpscp(5m)CpslnGpslnTA-p-(PS)2-GalNAc4 3' | B | Z |
| 368 | 145 | 5' ln(5m)Cpsln(5m)CpslnApsln(5m)Cps(5m)CpsAps(5m)CpsGpsApsGpsTps(5m)CpsTpsApslnGpslnApsam(5m)CA-p-(PS)2-GalNAc4 3' | B | Y |
| 369 | 143 | 5' ln(5m)Cpsam(5m)CpslnApsln(5m)Cps(5m)CpsAps(5m)CpsGpsApsGpsTps(5m)CpsTpsApslnGpslnApsln(5m)CA-p-(PS)2-GalNAc4 3' | B | Y |
| 370 | 144 | 5' am(5m)Cpsln(5m)CpslnApsln(5m)Cps(5m)CpsAps(5m)CpsGpsApsGpsTps(5m)CpsTpsApslnGpslnApsln(5m)CA-p-(PS)2-GalNAc4 3' | B | Y |
| 371 | 146 | 5' ln(5m)Cpsln(5m)CpslnApsam(5m)Cps(5m)CpsAps(5m)CpsGpsApsGpsTps(5m)CpsTpsApslnGpslnApsln(5m)CA-p-(PS)2-GalNAc4 3' | B | X |
| 372 | 355 | 5' amGpsam(5m)CpsamGpsApsApsGpsTpsGps(5m)CpsAps(5m)CpsAps(5m)CpsamGpsamGA-p-(PS)2-GalNAc4 3' | B | X |
| 373 | 356 | 5' lnGpslnApscpTpslnApslnApsAps(8nh)Aps(5m)CpsGps(5m)Cps(5m)CpsGps(5m)CpslnApslnGpslnApsln(5m)CT-p-(PS)2-GalNAc4 3' | B | X |
| 374 | 357 | 5' lnGpsln(5m)CpscpGpsAps(8nh)ApsGpsTpsGps(5m)CpsAps(5m)CpsAps(5m)CpslnGpslnGA-p-(PS)2-GalNAc4 3' | B | Y |
| 375 | 358 | 5' lnGpslnApslnGpsApsGps(8nh)GpsTpsGps(5m)CpsGps(5m)Cps(5m)Cps(5m)Cpscp(5m)CpslnGpslnTA-p-(PS)2-GalNAc4 3' | B | Y |
| 376 | 359 | 5' GalNAc4-(PS)2-p-mUlnGpscp(5m)CpslnGpsAps(8nh)ApsGpsTpsGps(5m)CpsAps(5m)CpsAps(5m)CpslnGpslnG | B | Y |
| 377 | 156 | 5' lnGpslnGpslnApsTpsTps(5oh)CpsApsGps(5m)CpsGps(5m)Cps(5m)CpsGpslnApscp(5m)CpslnGA-p-(PS)2-GalNAc4 3' | B | Y |
| 428 | 155A | 5' lnGpslnGpslnApsTps(2s)Tps(5m)CpsApsGps(5m)CpsGps(5m)Cps(5m)CpsGpslnApscp(5m)CpslnGA-p-(PS)2-GalNAc4 3' | B | X |

Example 9. Modified ASO Testing in AAV-HBV Mouse Model

This example evaluates the therapeutic index of ASOs using a dosing regimen of 5×10 mg/kg. ASOs were tested at 5×10 mg/kg every 3 days in the adeno-associated virus (AAV)-HBV mouse model. The resulting nadir $\log_{10}$ reduction in serum HBsAg and fold-change in ALT during the study are presented in Table 10, where A≥1 $\log_{10}$ reduction in HBsAg, B is 0.5-1 $\log_{10}$ reduction in HBsAg, and C is <0.5 $\log_{10}$ reduction in HBsAg, and X≤3-fold of ALT of vehicle control, which is considered normal. Y is 3-fold-30-fold of ALT of vehicle control, and Z is ≥30-fold of ALT of vehicle control. Both Y and Z showed liver tox with Z being more severe.

Figure 3A:
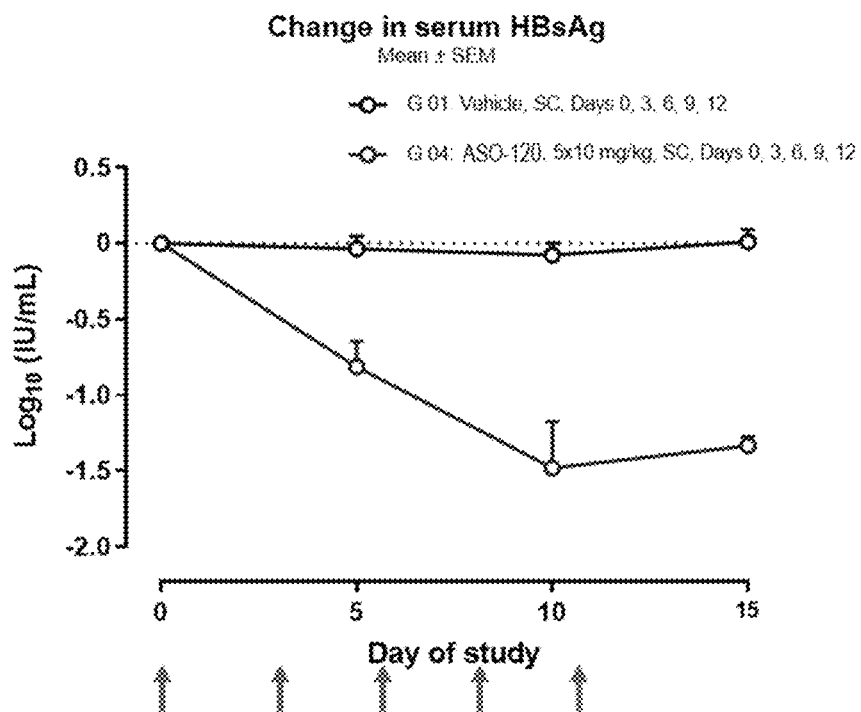
FIG. 3A shows a graph of the change in serum HBsAg from HBV mice treated with ASO 120.
Figure 3B:
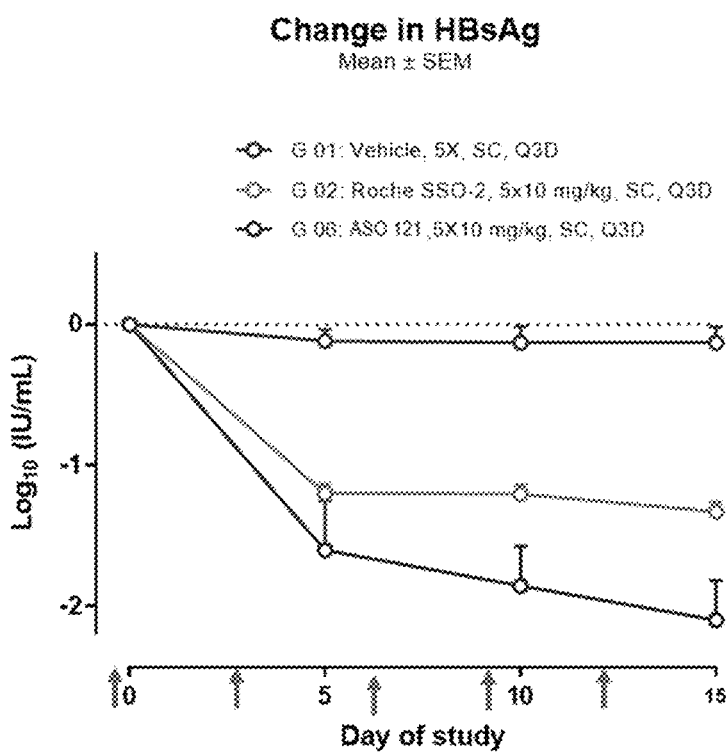
FIG. 3B shows a graph of the change in serum HBsAg from HBV mice treated with ASO 121.
Figure 3C:
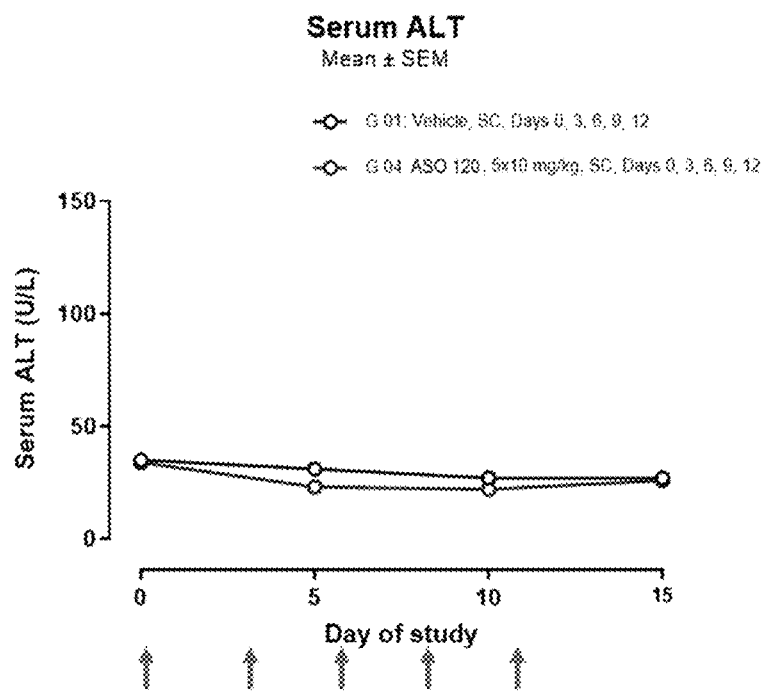
FIG. 3C shows a graph of serum ALT from HBV mice treated with ASO 120.
Figure 3D:
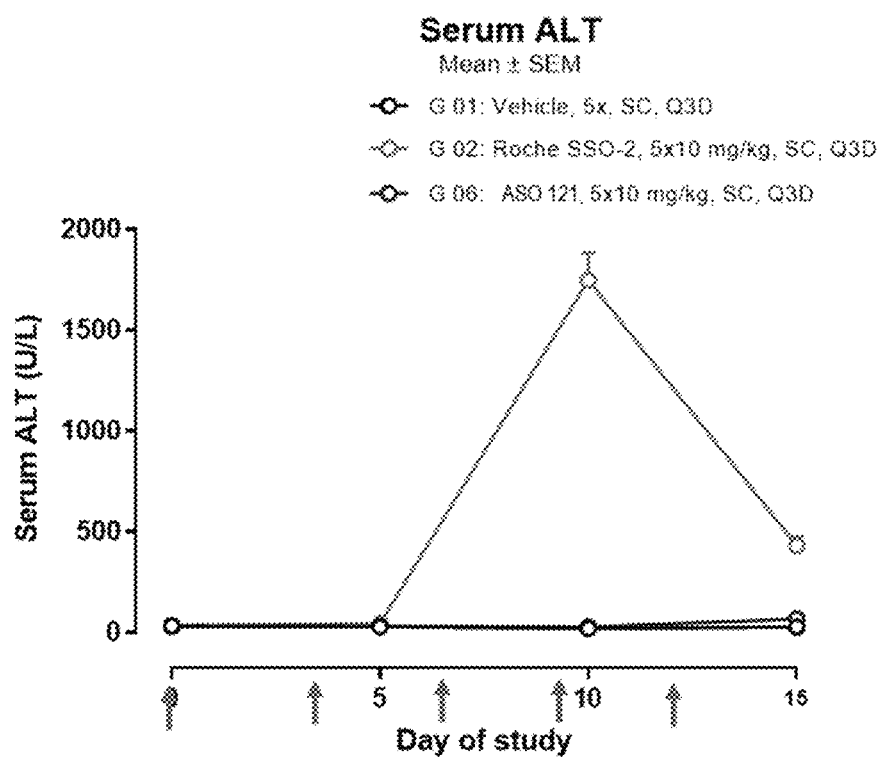
FIG. 3D shows a graph of serum ALT from HBV mice treated with ASO 121.

FIG. 3A shows a graph of the change in serum HBsAg for ASO 120. FIG. 3B shows a graph of the change in serum HBsAg for ASO 121. FIG. 3C shows a graph of the serum ALT for ASO 120. FIG. 3D shows a graph of the serum ALT for ASO 121. These results demonstrate that Luxna Chemistry modifications reduced or eliminated ALT, while maintaining in vivo potency.

The following specific sequences in Table 10 are within the scope of the present disclosure. As used herein, ln=Locked nucleic acid (LNA); lnA=Locked nucleic acid (LNA) A; ln(5m)C=ln(5m)C=Locked nucleic acid (LNA)-5methyl C; lnG=Locked nucleic acid (LNA) G; lnT=Locked nucleic acid (LNA) T; (5m)C=5 methylC; mA=2-O-methoxy A; mU=2-O-methoxy U; (8nh)A=8-amino A; (8nh)G=8-amino G; (2s)T=2-thio T; cp=scp=cyclopropyl; cpC=scpC=cyclopropyl C; cpG=scpG=cyclopropyl G; cpT=scpT=cyclopropyl T; ps=phosphorothioate linkages.

TABLE 10

HBsAg Nadir (Log) and ALT for 5x10 mg/kg Q3D

| SEQ ID NO. | ASO # | Sequence | HBsAg Nadir (Log) | ALT |
|---|---|---|---|---|
| 270 | 147 | 5'-GalNAc2-C6-p-CAlnApslnGpsln(5m)CpsGpsApsApsGpsTpsGps(5m)CpsAps(5m)CpsApsln(5m)CpslnGpslnG-3' | A | Z |
| 276 | 270 | 5'-GalNAc2-C6-p-CAlnGpslnApslnTpslnApslnApsApsAps(5m)CpsGps(5m)Cps(5m)CpsGps(5m)CpslnApslnGpslnApsln(5m)C 3' | A | X |
| 379 | 361 | 5'-GalNAc2-C6-p-CAlnGpsln(5m)CpslnGps(8nh)ApsApsGpsTpsGps(5m)CpsAps(5m)CpsAps(5m)CpslnGpslnG-3' | A | X |
| 380 | 362 | 5'-GalNAc2-C6-p-CAlnGpsln(5m)CpslnGpsApsApsGpsTpsGps(5m)CpsAps(5m)CpsAps(5oh)CpslnGpslnG-3' | A | Y |
| 381 | 363 | 5'-GalNAc2-C6-p-CAlnGpsln(5m)CpslnGpsAps(8nh)ApsGpsTpsGps(5m)CpsAps(5m)CpsAps(5m)CpslnGpslnG-3' | A | Y |
| 382 | 364 | 5'-GalNAc2-C6-p-CAlnGpslnGpslnTps(8nh)GpsApsApsGps(5m)CpsGpsApsApsGpslnTpslnGpsln(5m)CpslnA-3' | A | X |
| 383 | 365 | 5'-GalNAc2-C6-p-lnGpsln(5m)CpslnGpsApsApsGpsTpsGps(5m)CpsAps(5m)CpsAps(5m)CpslnGpslnGmG-3' | A | Y |
| 384 | 366 | 5'-GalNAc2-C6-p-ln(5m)Cpsln(5m)CpslnApsln(5m)Cps(5m)CpsAps(5m)CpsGpsApsGpsTps(5m)CpsTpsApslnGpslnApsln(5m)CmG-3' | A | X |
| 385 | 367 | 5'-GalNAc2-C6-p-CAlnGpslnApslnTpslnApslnAps(8nh)ApsAps(5m)CpsGps(5m)Cps(5m)CpsGps(5m)CpslnApslnGpslnApsln(5m)C-3' | A | Y |
| 386 | 368 | 5'-GalNAc2-C6-p-CAlnGpslnApslnTpslnApslnApsAps(8nh)Aps(5m)CpsGps(5m)Cps(5m)CpsGps(5m)CpslnApslnGpslnApsln(5m)C-3' | A | X |
| 387 | 369 | 5'-GalNAc2-C6-p-CAlnGpslnApslnTpslnApslnApsApsAps(5oh)CpsGps(5m)Cps(5m)CpsGps(5m)CpslnApslnGpslnApsln(5m)C-3' | A | X |
| 388 | 370 | 5'-GalNAc2-C6-p-CAln(5m)Cpsln(5m)CpslnApsln(5m)Cps(5oh)CpsAps(5m)CpsGpsApsGpsTps(5m)CpsTpsApslnGpslnApsln(5m)C-3' | A | X |
| 389 | 371 | 5'-GalNAc2-C6-p-CAln(5m)Cpsln(5m)CpslnApsln(5m)Cps(5m)Cps(8nh)Aps(5m)CpsGpsApsGpsTps(5m)CpsTpsApslnGpslnApsln(5m)C-3' | A | X |
| 390 | 372 | 5'-GalNAc2-C6-p-CAln(5m)Cpsln(5m)CpslnApsln(5m)Cps(5m)CpsAps(5oh)CpsGpsApsGpsTps(5m)CpsTpsApslnGpslnApsln(5m)C-3' | A | Y |
| 391 | 373 | 5'-ln(5m)Cpsln(5m)CpslnApsln(5m)Cps(5oh)CpsAps(5m)CpsGpsApsGpsTps(5m)CpsTpsApslnGpscpApsln(5m)CmA-p-(PS)2-GalNAc3-3' | A | Y |
| 392 | 157 | 5'-lnGpslnApslnTpsTps(5oh)CpsApsGps(5m)CpsGps(5m)Cps(5m)CpsGpsApsln(5m)CpslnGpslnGpscpGT-p-(PS)2-GalNAc4-3' | A | Z |
| 393 | 158 | 5'-lnGpslnApscpTps(2s)Tps(5m)CpsApsGps(5m)CpsGps(5m)Cps(5m)CpsGpsApsln(5m)CpslnGpslnGpslnGT-p-(PS)2-GalNAc4-3' | B | Y |

TABLE 10-continued

HBsAg Nadir (Log) and ALT for 5x10 mg/kg Q3D

| SEQ ID NO. | ASO # | Sequence | HBsAg Nadir (Log) | ALT |
|---|---|---|---|---|
| 394 | 159 | 5'-lnGpslnApscpTpsTps(5m)Cps(8nh)ApsGps(5m)CpsGps(5m)Cps(5m)CpsGpsApsln(5m)CpslnGpslnGpslnGT-p-(PS)2-GalNAc4-3' | A | X |
| 395 | 374 | 5'-ln(5m)Cpsln(5m)CpslnApsln(5m)Cps(5m)CpsAps(5oh)CpsGpsApsGpsTps(5m)CpsTpsApslnGpscpApsln(5m)CmA-p-(PS)2-GalNAc4-3' | A | Z |
| 396 | 128 | 5'-GalNAc4-(PS)2-p-mAlnGpslnApslnTpslnApslnApsApsAps(5m)CpsGps(5m)Cps(5m)CpsGps(5m)CpslnApslnGpslnApscp(5m)C-3' | A | X |
| 397 | 129 | 5'-GalNAc4-(PS)2-p-mAlnGpslnApslnTpslnApslnAps(8nh)ApsAps(5m)CpsGps(5m)Cps(5m)CpsGps(5m)CpslnApslnGpslnApscp(5m)C-3' | A | X |
| 398 | 130 | 5'-GalNAc4-(PS)2-p-mAln(5m)Cpscp(5m)CpslnApsln(5m)Cps(5m)Cps(8nh)Aps(5m)CpsGpsApsGpsTps(5m)CpsTpsApslnGpslnApsln(5m)C-3' | B | X |
| 399 | 375 | 5'-GalNAc4-(PS)2-p-mAln(5m)Cpsln(5m)CpslnApsln(5m)Cps(5m)Cps(8nh)Aps(5m)CpsGpsApsGpsTps(5m)CpsTpsApscpGpslnApsln(5m)C-3' | A | X |
| 400 | 120 | 5'-GalNAc4-(PS)2-p-mAlnGpslnApslnTpslnApslnApsApsAps(5oh)CpsGps(5m)Cps(5m)CpsGps(5m)CpslnApslnGpslnApscp(5m)C-3' | A | X |
| 401 | 376 | 5'-GalNAc4-(PS)2-p-mAlnGpsamApslnTpslnApslnApsApsAps(5oh)CpsGps(5m)Cps(5m)CpsGps(5m)CpslnApslnGpslnApsln(5m)C-3' | B | X |
| 402 | 377 | 5'-GalNAc4-(PS)2-p-mAlnGpslnGpscpTpsGpsAps(8nh)ApsGps(5m)CpsGpsApsApsGpslnTpslnGpsln(5m)CpslnA-3' | A | X |
| 403 | 378 | 5'-ln(5m)Cpsln(5m)CpslnApsln(5m)Cps(5m)Cps(8nh)Aps(5m)CpsGpsApsGpsTps(5m)CpsTpsApslnGpscpApsln(5m)CmA-p-(PS)2-GalNAc4-3' | B | X |

Example 10. Modified ASO Testing in AAV-HBV Mouse Model

ASOs were tested at 1×10 mg/kg in the adeno-associated virus (AAV)-HBV mouse model as single agents or in combination (S+X Triggers as well as S+S Triggers). The resulting nadir $\log_{10}$ reduction in serum HBsAg and fold-change in ALT during the study are presented in Table 11, where A≥1 $\log_{10}$ reduction in HBsAg, B is 0.5-1 $\log_{10}$ reduction in HBsAg, and C is <0.5 $\log_{10}$ reduction in HBsAg, and X≤3-fold of ALT of vehicle control, Y is 3-fold-30-fold of ALT of vehicle control, and Z is ≥30-fold of ALT of vehicle control. The results demonstrated when S and X Triggers ASOs were combined, they showed additive to minor synergistic effects.

Figure 9A:
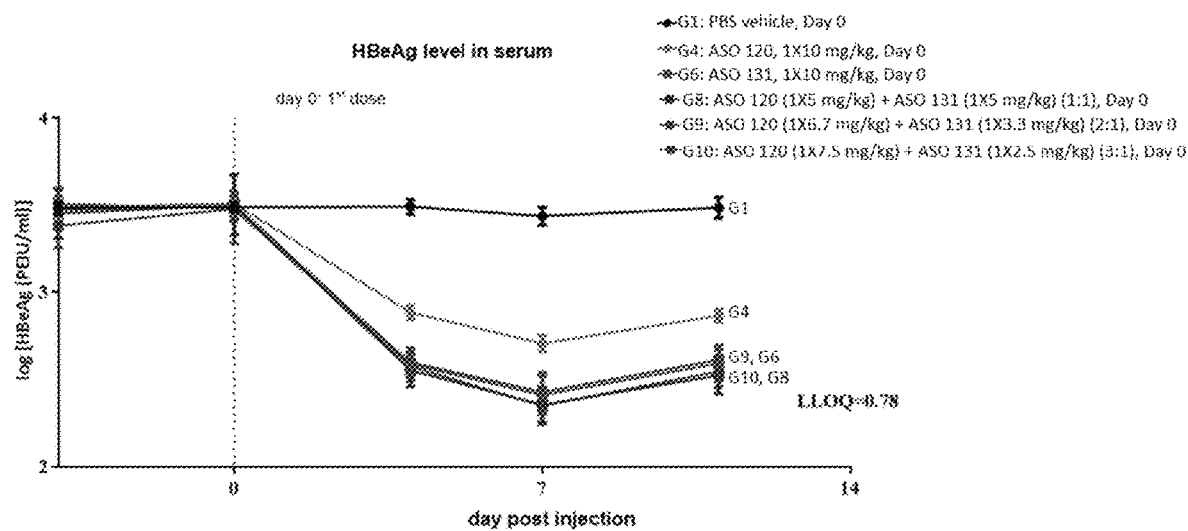
FIG. 9A shows a graph of the change in serum HBeAg from mice treated with single dose ASO 120, ASO 131, and combinations of ASO 120 and ASO 131 at 1:1, 2:1, and 3:1 mass ratio.
Figure 9B:
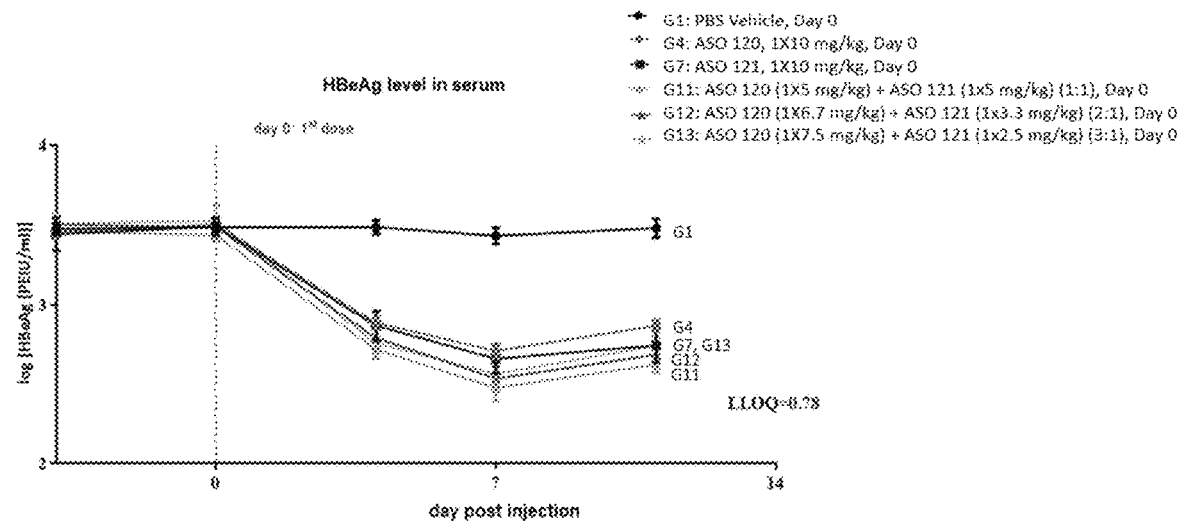
FIG. 9B shows a graph of the change in serum HBeAg from mice treated with single dose ASO 120, ASO 121, and combinations of ASO 120 and ASO 121 at 1:1, 2:1, and 3:1 mass ratio.

FIG. 9A shows a graph of the change in serum hepatitis B e-antigen (HBeAg) from mice treated with ASO 120, ASO 131, and combinations of ASO 120 and ASO 131 at 1:1, 2:1, and 3:1 mass ratios. FIG. 9B shows a graph of the change in serum HBeAg from mice treated with ASO 120, ASO 121, and combinations of ASO 120 and ASO 121 at 1:1, 2:1, and 3:1 mass ratios. These results demonstrate that combination with ASOs results in destruction of all HBV RNA including X gene, as well as RNA from integrated genome.

TABLE 11

HBsAg Nadir (Log) and ALT for 1x10 mg/kg

| SEQ ID NO. | ASO # | Sequence | HBsAg Nadir (Log) | ALT |
|---|---|---|---|---|
|

TABLE 11-continued

HBsAg Nadir (Log) and ALT for 1x10 mg/kg

| SEQ ID NO. | ASO # | Sequence | HBsAg Nadir (Log) | ALT |
|---|---|---|---|---|
| | ASO 130<br>ASO 121 (2:1) | | B | X |
| | ASO 130<br>ASO 121 (3:1) | | B | X |
| | ASO 130<br>ASO 131 (1:1) | | B | X |
| | ASO 130<br>ASO 131 (2:1) | | B | X |
| | ASO 130<br>ASO 131 (3:1) | | A | X |
| 399 | 375 | 5'-GalNAc4-(PS)2-p-mAln(5m)Cpsln(5m)CpslnApsln(5m)Cps(5m)Cps(8nh)Aps(5m)CpsGpsApsGpsTps(5m)CpsTpsApscpGpslnApsln(5m)C 3' | C | X |
| 400 | 120 | 5'-GalNAc4-(PS)2-p-mAlnGpslnApslnTpslnApslnApsApsAps(5oh)CpsGps(5m)Cps(5m)CpsGps(5m)CpslnApslnGpslnApscp(5m)C 3' | B | X |
| | ASO 120<br>ASO 121 (1:1) | | A | X |
| | ASO 120<br>ASO 121 (2:1) | | A | X |
| | ASO 120<br>ASO 121 (3:1) | | A | X |
| | ASO 120<br>ASO 131 (1:1) | | A | X |
| | ASO 120<br>ASO 131 (2:1) | | A | X |
| | ASO 120<br>ASO 131 (3:1) | | A | X |
| 401 | 376 | 5'-GalNAc4-(PS)2-p-mAlnGpsamApslnTpslnApslnApsApsAps(5Oh)CpsGps(5m)Cps(5m)CpsGps(5m)CpslnApslnGpslnApsln(5m)C 3' | C | X |
| 402 | 377 | 5'-GalNAc4-(PS)2-p-mAlnGpslnGpscpTpsGpsAps(8nh)ApsGps(5m)CpsGpsApsApsGpslnTpslnGpsln(5m)CpslnA 3' | B | X |
| 156 | 121 | 5'-GalNAc4-(PS)2-p-mUlnGpslnApscpTpsTps(5m)Cps(8nh)ApsGps(5m)CpsGps(5m)Cps(5m)CpsGpsApsln(5m)CpslnGpslnGpslnG 3' | A | X |
| 419 | 131 | 5'-GalNAc4-(PS)2-p-mUlnGpslnGpslnApsTps(2s)Tps(5m)CpsApsGps(5m)CpsGps(5m)Cps(5m)CpsGpslnApscp(5m)CpslnG 3' | A | X |

Example 11. Modified ASO Testing in AAV-HBV Mouse Model

Figure 4A:
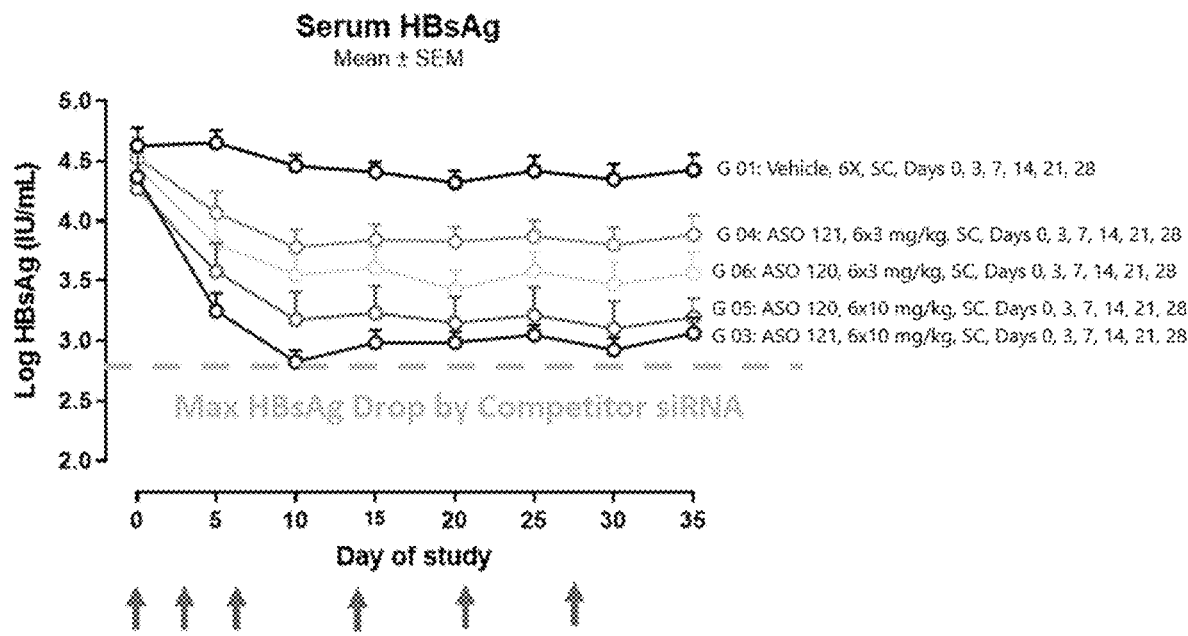
FIG. 4A shows a graph of the change in serum HBsAg from HBV mice treated with ASO 121 or ASO 120.
Figure 4B:
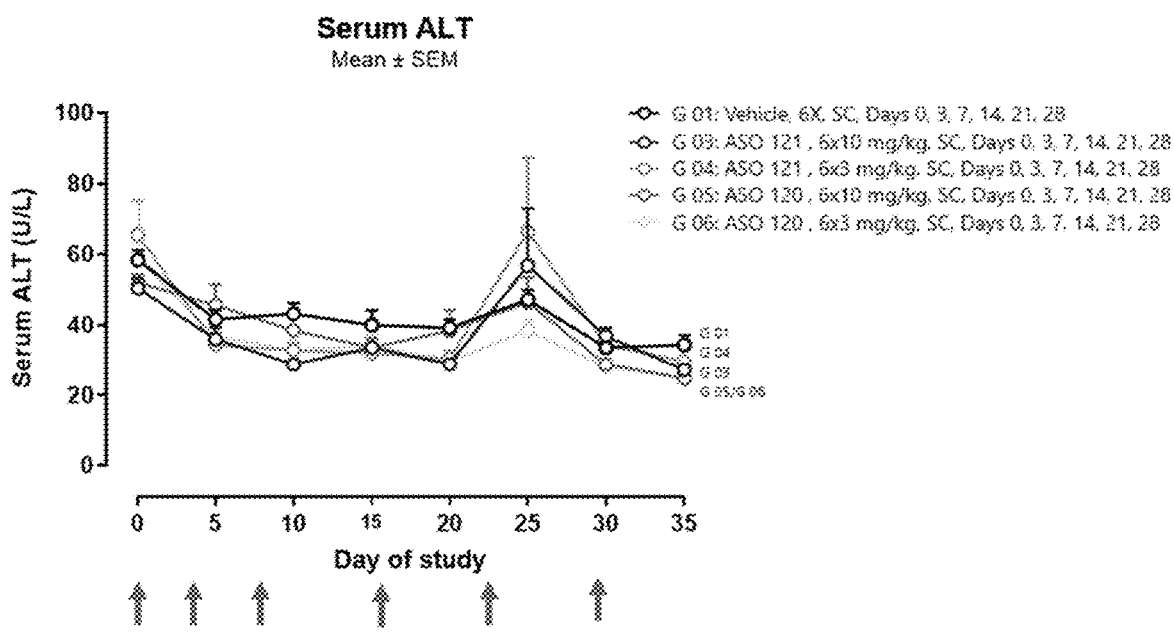
FIG. 4B shows a graph of serum ALT from HBV mice treated with ASO 121 or ASO 120.
Figure 4C:
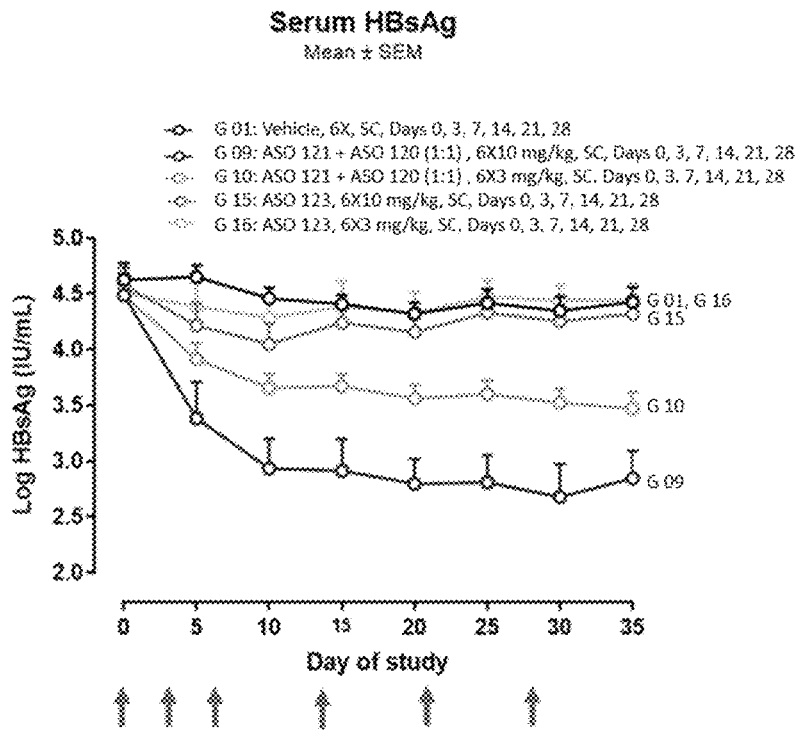
FIG. 4C shows a graph of the change in serum HBsAg from HBV mice treated with (i) a combination of ASO 121 and ASO 120; or (ii) ASO 123 as a single agent.
Figure 4D:
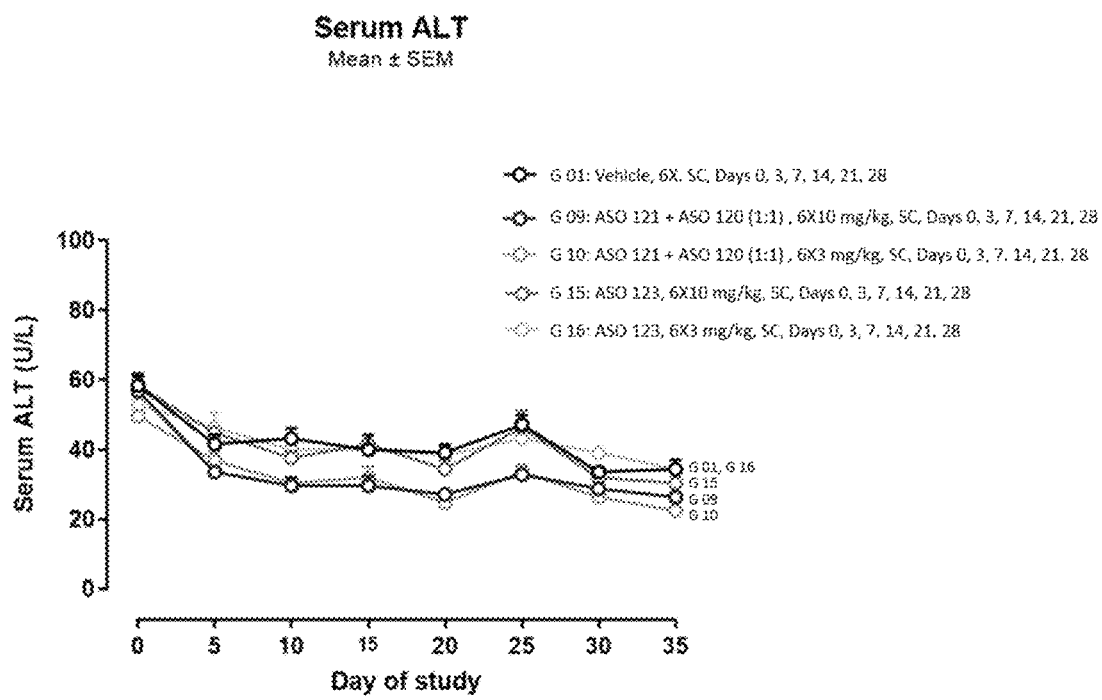
FIG. 4D shows a graph of serum ALT from HBV mice treated with (i) a combination of ASO 121 and ASO 120; or (ii) ASO 123 as a single agent.

ASOs were tested at 6 repeat doses of 3 mg/kg or 10 mg/kg at days 0, 3, 7, 14, 21, and 28 in the adeno-associated virus (AAV)-HBV mouse model. The resulting nadir $\log_{10}$ reduction in serum HBsAg and fold-change in ALT during the study are presented in Table 12, where A≥1 $\log_{10}$ reduction in HBsAg, B is 0.5-1 $\log_{10}$ reduction in HBsAg, and C is <0.5 $\log_{10}$ reduction in HBsAg, and X≤3-fold of ALT of vehicle control, which considered normal. Y is 3-fold-30-fold of ALT of vehicle control, and Z is ≥30-fold of ALT of vehicle control Both Y and Z show liver toxicity. The S and X ASO Trigger in combination of (1:1 and 2:1) while the total dosing drug amounts (in mg) are constant regardless whether they are single agents or combined agents. The results showed S and X combination (1:1) has minor synergistic effect while 2:1 (S:X) mixture showed less benefit. FIG. 4A shows a graph of the change in serum HBsAg from HBV mice treated with ASO 121 or ASO 120. FIG. 4B shows a graph of serum ALT from HBV mice treated with ASO 121 or ASO 120. FIG. 4C shows a graph of the change in serum HBsAg from HBV mice treated with (a) a combination of ASO 121 and ASO 120; or (b) ASO 123 alone. FIG. 4D shows a graph of serum ALT from HBV mice treated with (a) combination of ASO 121 and ASO 120; or (b) ASO 123 alone. These results demonstrate that ASOs with Luxna Wing and gap-modified chemistries can effectively treated HBV. In addition, mice treated with a combination of two ASOs showed improved potency as compared to mice treated with ASO 123 alone. ASO 123 is GSK836, which is currently in a Phase 2B clinical trial sponsored by GSK.

TABLE 12

HBsAg Nadir (Log) and ALT for 6 Repeat Doses at D 0, 3, 7, 14, 21, 28

| ASO #* | Dose | HBsAg Nadir (Log) | ALT |
|---|---|---|---|
| 123 | 6 × 10 mg/kg | B | X |
| 123 | 6 × 3 mg/kg | C | X |
| 130 | 6 × 10 mg/kg | B | X |
| 130 | 6 × 3 mg/kg | C | X |
| 120 | 6 × 10 mg/kg | A | X |
| 120 | 6 × 3 mg/kg | A | X |

TABLE 12-continued

HBsAg Nadir (Log) and ALT for 6 Repeat Doses at D 0, 3, 7, 14, 21, 28

| ASO #* | Dose | HBsAg Nadir (Log) | ALT |
|---|---|---|---|
| ASO 120 +ASO 130 (1:1) | 6 × 10 mg/kg | A | X |
| ASO 120 +ASO 130 (1:1) | 6 × 3 mg/kg | B | X |
| ASO 120 +ASO 121 (1:1) | 6 × 10 mg/kg | A | X |
| ASO 120 +ASO 121 (1:1) | 6 × 3 mg/kg | A | X |
| ASO 120 +ASO 121 (2:1) | 6 × 10 mg/kg | A | X |
| ASO 120 +ASO 121 (2:1) | 6 × 3 mg/kg | B | X |
| ASO 121 | 6 × 10 mg/kg | A | X |
| ASO 121 | 6 × 3 mg/kg | B | X |

*For combinations, (1:1) and (2:1) refer to mass ratios of the ASOs.

Example 12. ASO Dose Response Testing in HBsAg Release Assay in HepG2.2.15 HBV Cell Model In vitro screenings of increasing doses of ASOs were carried out in HepG2.2.15 cells using HBsAg release assay. The dose response curves and resulting $IC_{50}$ (nm) values for three experiments are shown in FIGS. 1A-2C and Table 13, where A: ≤5 nM, B is 5-20 nM, C: ≥20 nM. The results demonstrate Luxna chemistry modified ASOs (modified in both Wing and Gap) showed good in vitro potency. For some sequence the ASO with GalNac attached still show good potency comparing with the same ASO with GalNac removed. For other sequence, ASO with GalNacx still attached showed less potency comparing with unconjugated ASO of the same sequence.

TABLE 13

$IC_{50}$ (nM) values for ASO Dose Response

| SEQ ID NO. | ASO # | Sequence | IC50 (nM) Expt. 1 | Expt. 2 | Expt. 3 |
|---|---|---|---|---|---|
| 420 | 126 | 5'-mA-lnGpslnApslnTpslnApslnApsApsAps(5oh)CpsGps(5m)Cps(5m)CpsGps(5m)CpslnApslnGpslnApscp(5m)C-3' | B | B | B |
| 400 | 120 | 5'-GalNac4-ps2-p-mA-lnGpslnApslnTpslnApslnApsApsAps(5oh)CpsGps(5m)Cps(5m)CpsGps(5m)CpslnApslnGpslnApscp(5m)C-3 | C | C | C |
| 421 | 124 | 5'-lnGpslnApslnTpslnApslnApsApsAps(5oh)CpsGps(5m)Cps(5m)CpsGps(5m)CpslnApslnGpslnApscp(5m)C-3' | B | B | B |
| 422 | 127 | 5' mU-lnGpslnApscpTpsTps(5m)Cps(8nh)ApsGps(5m)CpsGps(5m)Cps(5m)CpsGpsApsln(5m)CpslnGpslnGpslnG-3' | A | A | A |
| 156 | 121 | 5' GalNac4-ps2-p-mU-po-lnGpslnApscpTpsTps(5m)Cps(8nh)ApsGps(5m)CpsGps(5m)Cps(5m)CpsGpsApsln(5m)CpslnGpslnGpslnG-3' | A | A | A |
| 404 | 125 | 5' lnGpslnApscpTpsTps(5m)Cps(8nh)ApsGps(5m)CpsGps(5m)Cps(5m)CpsGpsApsln(5m)CpslnGpslnGpslnG-3' | A | A | A |

Example 13. ASO Synthesis

ASOs with LNA and/or gap-modified chemistries were synthesized on ABI 394 and Expedite 8909 synthesizers using standard phosphoramidite chemistry. LNA-containing ASOs were conjugated to N-Acetylgalactosamine (GalNac).

The following specific sequences in Table 14 are within the scope of the present disclosure. As used herein, ln=Locked nucleic acid (LNA); lnA=Locked nucleic acid (LNA) A; ln(5m)Cln(5m)C=Locked nucleic acid (LNA)-5methyl C; lnG=Locked nucleic acid (LNA) G; lnT=Locked nucleic acid (LNA) T; (5m)C=5 methylC; mA=2-O-methoxy A; mU=2-O-methoxy U; (8nh)A=8-amino A; (8nh)G=8-amino G; (2s)T=2-thio T; cp=scp=cyclopropyl; cpC=scpC=cyclopropyl C; cpG=scpG=cyclopropyl G; cpT=scpT=cyclopropyl T; ps=phosphorothioate linkages.

TABLE 14

ASO Synthesis

| SEQ ID NO. | ASO No. | Sequence 5'→3' | Total Amount (mg) | Final Amount (µmole) |
|---|---|---|---|---|
| 405 | 380 (ASO 120 analog) | cpGpscpApscpTpscpApscpApsApsAps(5Oh) CpsGps(5m)Cps(5m)CpsGps(5m)CpscpApscp GpscpApscp(5m)C | 0.33 | 0.05 |
| 406 | 381 (ASO 121 analog) | cpGpscpApscpTpsTps(5m)Cps(8nh)ApsGps (5m)CpsGps(5m)Cps(5m)CpsGpsApscp(5m) CpscpGpscpGpscpG | 0.36 | 0.06 |
| 407 | 382 (ASO 130 analog) | cp(5m)Cpscp(5m)CpscpApscp(5m)Cps(5m) Cps(8nh)Aps(5m)CpsGpsApsGpsTps(5m)Cps TpsApscpGpscpApscp(5m)C | 0.36 | 0.06 |

HepG2.2.15 cells (a stable cell line with four integrated HBV genomes) were maintained in DMEM medium with 10% fetal bovine serum (FBS) and 1% penicillin/streptomycin, 1% Glutamine, 1% non-essential amino acids, 1% Sodium Pyruvate and 250 µg/ml G418. Cells were maintained at 37° C. in a 5% $CO_2$ atmosphere. For HBsAg release assay, assay medium was made: DMEM with 5% FBS, 1% penicillin/streptomycin, 1% Glutamine and 1% DMSO. The day before assay, trypsinize HepG2.2.15 cells were washed with Assay Medium once, spun at 250 g×5 min, resuspended with Assay Medium, and seed cells at 50,000/well in assay medium in collagen coated 96 well plates. On the next day, ASOs were diluted with Opti-MEM, 9-pt, 3-fold dilution and Lipofectamine RNAiMAX (Invitrogen) was diluted according manufacturer's manual. The ASO dilution and RNAiMAX dilution was mixed, left at room temperature for 5 minutes and 15 µl was added to each well of 96 well plate. The plates were left at 37° C., 5% $CO_2$ in an incubator for 5 days. After incubation, the supernatant was harvested and measured for HBsAg with ELISA kit (Diasino). The cell viability was measured with CellTiter-Glo (Promega). The $EC_{50}$, the concentration of the drug required for reducing HBsAg secretion by 50% in relation to the untreated cell control was calculated using the Prism Graphpad. The $CC_{50}$, the concentration of the drug required for reducing cell viability by 50% in relation to the untreated cell control was calculated with the same software.

The resulting $EC_{50}$ and $CC_{50}$ for the compounds in Table 14 are presented in the following Table 15. The $EC_{50}$ values are as follows: A: <0.1 nM, B: 0.1 nM-5 nM, C: >5 nM.

| ASO No. | $EC_{50}$ | $CC_{50}$ |
|---|---|---|
| 380 | C | >500 |
| 381 | B | >500 |
| 382 | C | >500 |

Example 14. Bioinformatics of ASOs Targeting S and X Gene Regions of HBV

This example analyzes the genotypic coverage and off target profile of ASOs targeting S and X gene regions of HBV. Table 15 shows the genotypic coverage of HBV genotypes A-J for ASO 120, which targets the S gene region, and ASO 121, which targets the X gene region. The % homology (defined as fully match or with 1 mismatch) among >8000 clinical isolates is shown in Table 16.

TABLE 16

Genotypic Coverage: % Homology among >8000 clinical isolates

| Genotype | A | B | C | D | E | F | G | H | I | J |
|---|---|---|---|---|---|---|---|---|---|---|
| ASO 120 (S) | 98% | 100% | 99% | 100% | 100% | 100% | 100% | 100% | 100% | 100% |
| ASO 121 (X) | 99% | 100% | 99% | 100% | 96% | 100% | 99% | 100% | 100% | 97% |

TABLE 16-continued

| Genotypic Coverage: % Homology among >8000 clinical isolates | | | | | | | | | | |
|---|---|---|---|---|---|---|---|---|---|---|
| Genotype | A | B | C | D | E | F | G | H | I | J |
| ASO 120 (S) + ASO 121 (X) | 100% | 100% | 100% | 100% | 100% | 100% | 100% | 100% | 100% | 100% |

Example 15. ASO Combination Therapies

This example investigates combination therapies with ASO 120 and ASO 121 and other HBV therapies (e.g., S-antigen transport-inhibiting oligonucleotide polymers (STOPS), tenofovir, and capsid assembly modulators (CAMs)). For the STOPS ALG-010133 combination studies with ASOs (ASO 120:ASO121 in 2:1, 1:1 or 1:2 ratio), 35,000 HepG2.2.15 cells per well were reverse transfected in a collagen I-coated 96-well plate (Corning, Biocoat; Catalog 356698). ALG-010133 and the ASO mixture were diluted in Opti-MEM™ I Reduced Serum Medium (Thermo Fisher Scientific; Catalog 31985088) to 40× the desired final test concentration then serially diluted (1:3) up to 5 or 9 distinct concentrations, respectively. A 3.25-µL aliquot of each diluted compound was combined in a checkerboard fashion where the ASO mixture was added to 10 columns with highest concentration at the top of the plate and ALG-010133 was added to 7 rows with the highest concentration at the furthest well on the right of the plate. This combination of compounds was mixed with 0.3 µL Lipofectamine® RNAiMAX Transfection Reagent (Thermo Fisher Scientific, Catalog 13778150) and 6.2 µL of Opti-MEM™ I Reduced Serum Medium. After incubating for 20 minutes, the mixture was added to the HepG2.2.15 cells. Space was also allotted for titrations of each compound alone as reference controls. Cells were incubated with compounds for 3 days at 37° C. in a 5% $CO_2$ atmosphere. Three days after initial transfection, the media was refreshed, and the cells were re-transfected following the same protocol as used for the initial transfection. After another 3 days, the supernatant were assayed for HBsAg levels and remaining cells were analyzed for cytotoxicity. For ASO mixture combinations with small molecules such as CAM or Tenofovir, the test articles, were dissolved in dimethyl sulfoxide (DMSO) stock solutions and added to cells without transfection at a final concentration of 0.5% DMSO. All the other aspects of the assay were consistent with the protocol used for the ASO+STOPS combination studies. HBV DNA in the supernatant was measured for these combinations with small molecules such as CAM or Tenofovir.

The HBsAg level was determined using the HBsAg ELISA kit (Diasino Laboratories, Ref. DS187701) according to the manufacturer's protocol. Luminescence was recorded using a Perkin Elmer multilabel counter Victor3V. HBV DNA levels were measured with real time qPCR.

For the HepG2.2.15 cell viability assay, a Promega Cell-Titer-Glo® Luminescent Cell Viability Assay (Catalog G7572) was used. The CellTiter-Glo Luminescent Cell Viability Assay is a homogeneous method to determine the number of viable cells in culture based on quantitation of the adenosine triphosphate (ATP) present, which signals the presence of metabolically active cells. Assay plates were set up in the same format as in the anti-HBV activity assays. A 100-µL aliquot of CellTiter-Glo reagent was added to each well and incubated at room temperature for 8 minutes. Luminescence was recorded using a Perkin Elmer multilabel counter Victor3V.

Each experiment was performed in triplicate (3 plates). Mean percentage inhibition of HBsAg from the three experiments was generated and analyzed using Prichard's Method (Mac Synergy II).

As shown in Table 17, the ASO combination therapy with STOPShad an additive effect in HBsAg reduction with no cytotoxicity. As shown in Table 18, the ASO combination therapy with tenofovir had a strong synergistic effect in HBsAg reduction and the ASO combination therapy with CAM had a moderate synergistic effect in HBsAg reduction.

TABLE 17

ASO Combination Therapy with STOPS™ ALG-010133

| Compound | ASO 120:ASO121 ratio | Synergy | Cytotoxicity |
|---|---|---|---|
| STOPS | 1:2 | Additive | No |
| STOPS | 1:1 | Additive | No |
| STOPS | 2:1 | Additive | No |

TABLE 18

ASO Combination (ASO 120 + ASO121 1:1) Therapy with HBV Therapeutic Agents

| Compound | Class | Synergy | CC50 |
|---|---|---|---|
| Tenofovir | NA | Strong Synergy | No |
| CAM | CAM II | Moderate Synergy | No |

Example 16. Modified ASO Testing in AAV-HBV Mouse Model

Figure 5A:
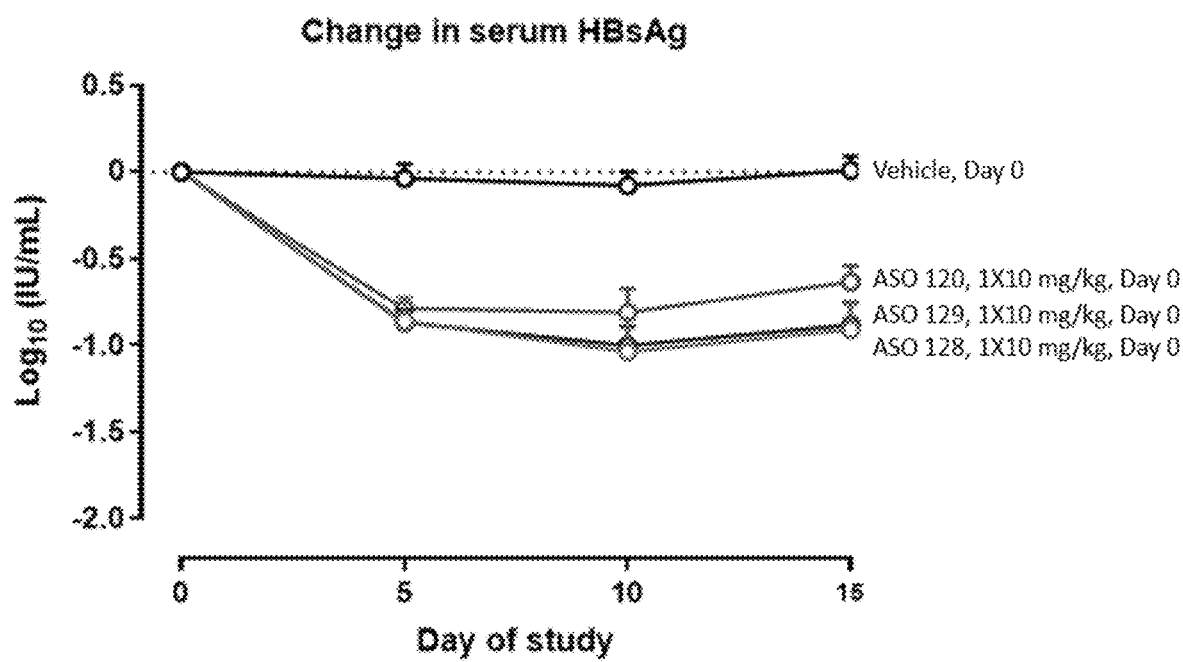
FIG. 5A shows a graph of the change in serum HBsAg from mice treated with 1×5 mg/kg of ASO 128, ASO 129, or ASO 120.
Figure 5B:
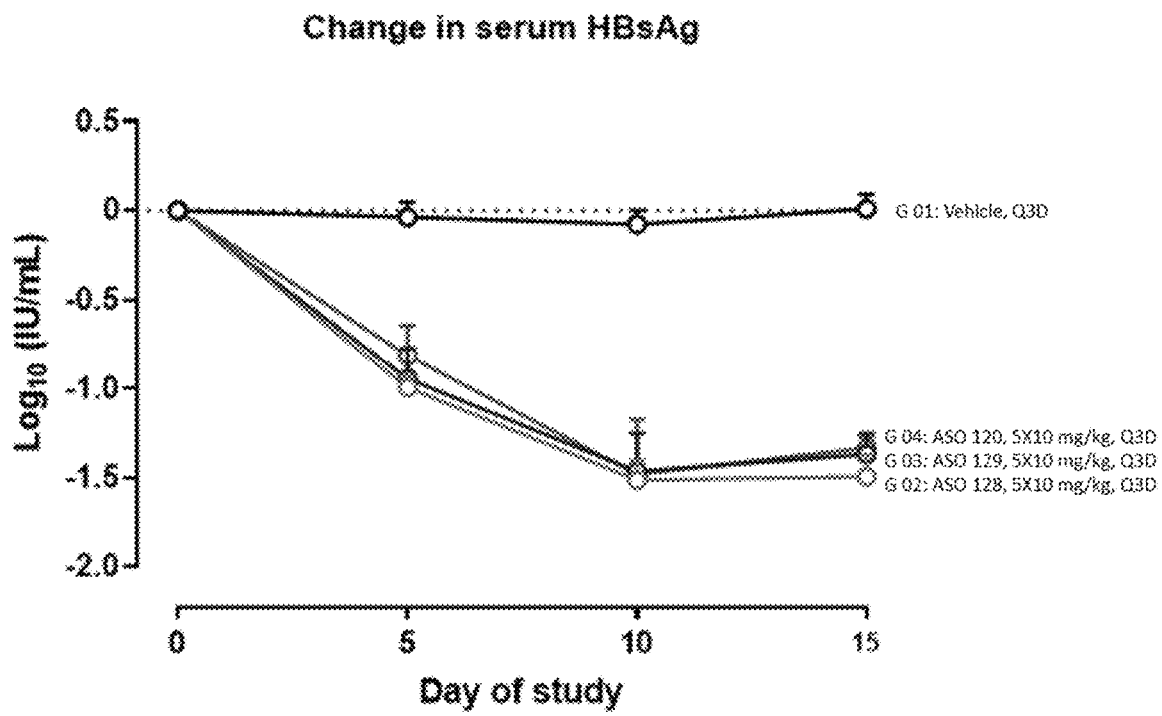
FIG. 5B shows a graph of the change in serum HBsAg from mice treated with 5×10 mg/kg Q3D of ASO 128, ASO 129, or ASO 120.
Figure 5C:
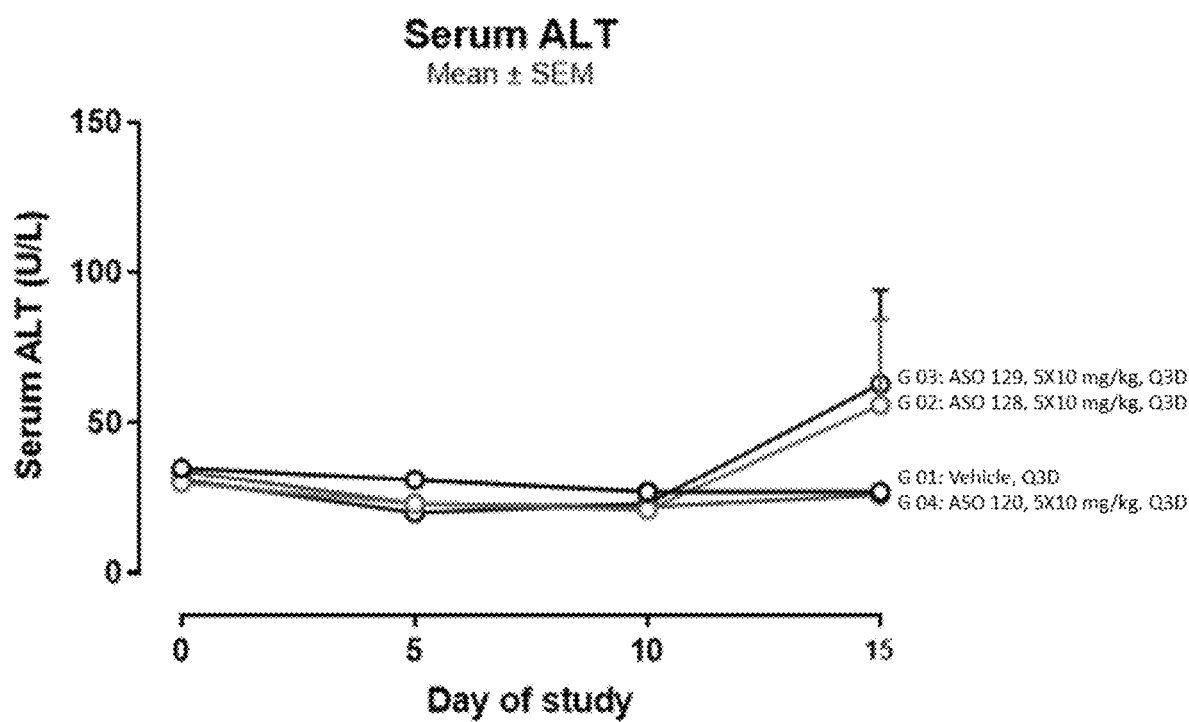
FIG. 5C shows a graph of the serum ALT from mice treated with 5×10 mg/kg Q3D of ASO 128, ASO 129, or ASO 120.

ASOs with LNA and/or Luxna wing or gap-modified chemistries were synthesized on ABI 394 and Expedite 8909 synthesizers using standard phosphoramidite chemistry. ASOs were tested at a dose of 1×10 mg/kg or 5×10 mg/kg every 3 days in the adeno-associated virus (AAV)-HBV mouse model. FIG. 5A shows a graph of the change in serum HBsAg from mice treated with 1×10 mg/kg of ASO 128, ASO 129, or ASO 120. FIG. 5B shows a graph of the change in serum HBsAg from mice treated with 5×10 mg/kg Q3D of ASO 128, ASO 129, or ASO 120. Efficacy of all 3 ASOs with no gap modification, Luxna Chemistry modification at Gap position #1, and Luxna Modification at Gap position #3 have the same potency. FIG. 5C shows a graph of the serum ALT from mice treated with 5×10 mg/kg Q3D of ASO 128, ASO 129, or ASO 120. The results showed Luxna modification at Gap position #3 has best liver safety profile.

Example 17. Evaluation of ASO 130 in AAV-HBV Mouse Model

Figure 6A:
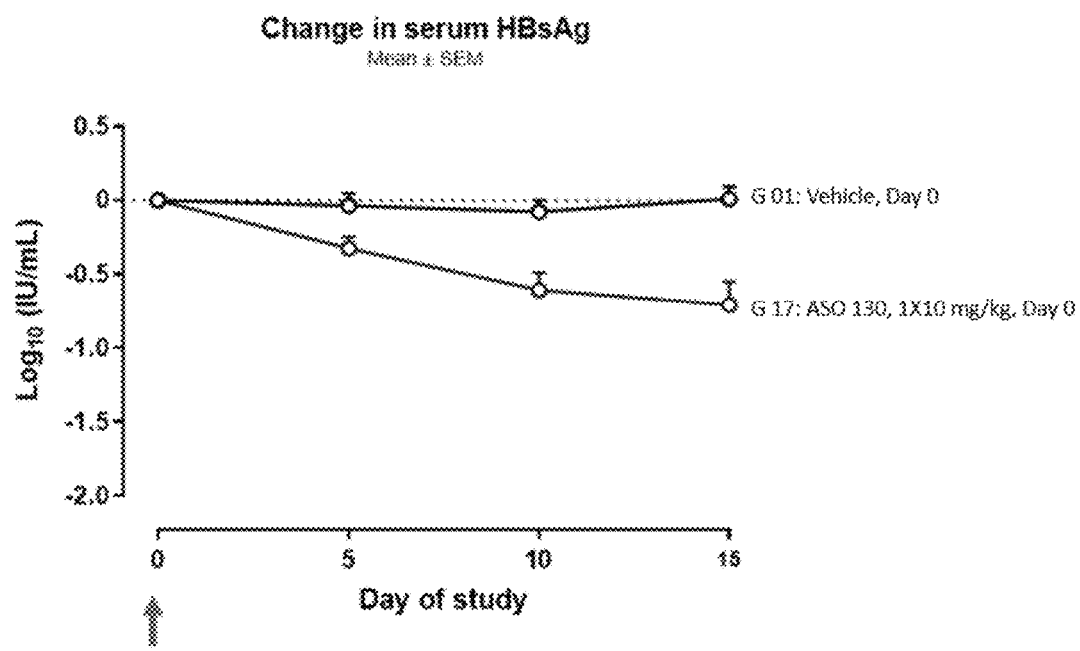
FIG. 6A shows a graph of the change in serum HBsAg from mice treated with 1×5 mg/kg of ASO 130.
Figure 6B:
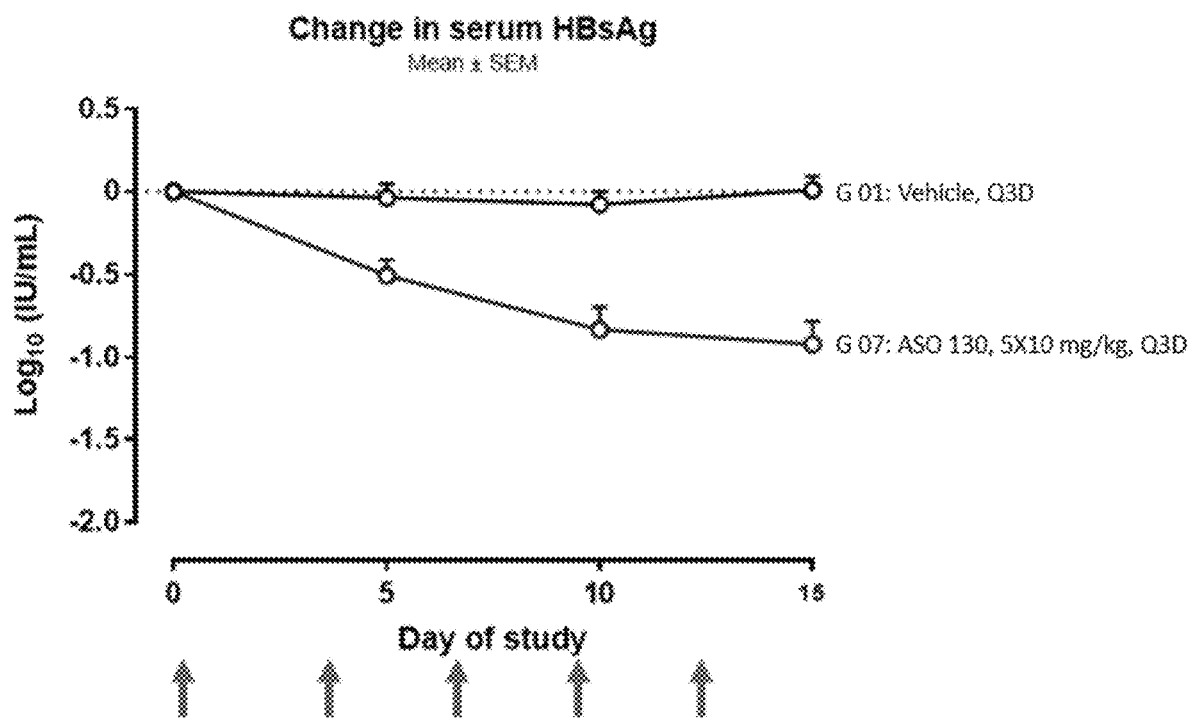
FIG. 6B shows a graph of the change in serum HBsAg from mice treated with 5×10 mg/kg Q3D of ASO 130.
Figure 6C:
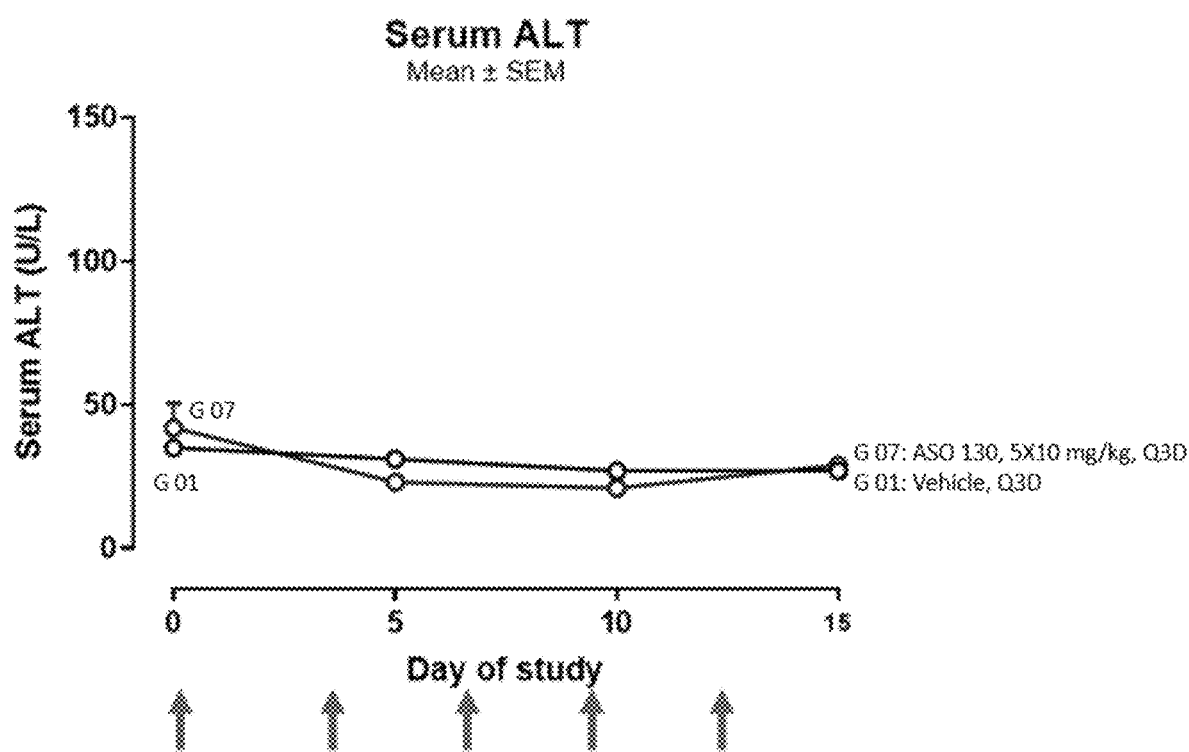
FIG. 6C shows a graph of the serum ALT from mice treated with 5×10 mg/kg Q3D of ASO 130.

ASO 130 was synthesized on ABI 394 and Expedite 8909 synthesizers using standard phosphoramidite chemistry. ASO 130 was tested at a dose of 1×10 mg/kg or 5×10 mg/kg every 3 days in the adeno-associated virus (AAV)-HBV mouse model. FIG. 6A shows a graph of the change in serum HBsAg from mice treated with 1×10 mg/kg of ASO 130. FIG. 6B shows a graph of the change in serum HBsAg from mice treated with 5×10 mg/kg Q3D of ASO 130. FIG. 6C shows a graph of the serum ALT from mice treated with 5×10 mg/kg Q3D of ASO 130. These results demonstrate that Luxna chemistry modifications at wing and gap can produce a robust, durable response without ALT elevation.

Example 18. Evaluation of ASO ASO 131 in AAV-HBV Mouse Model

Figure 7A:
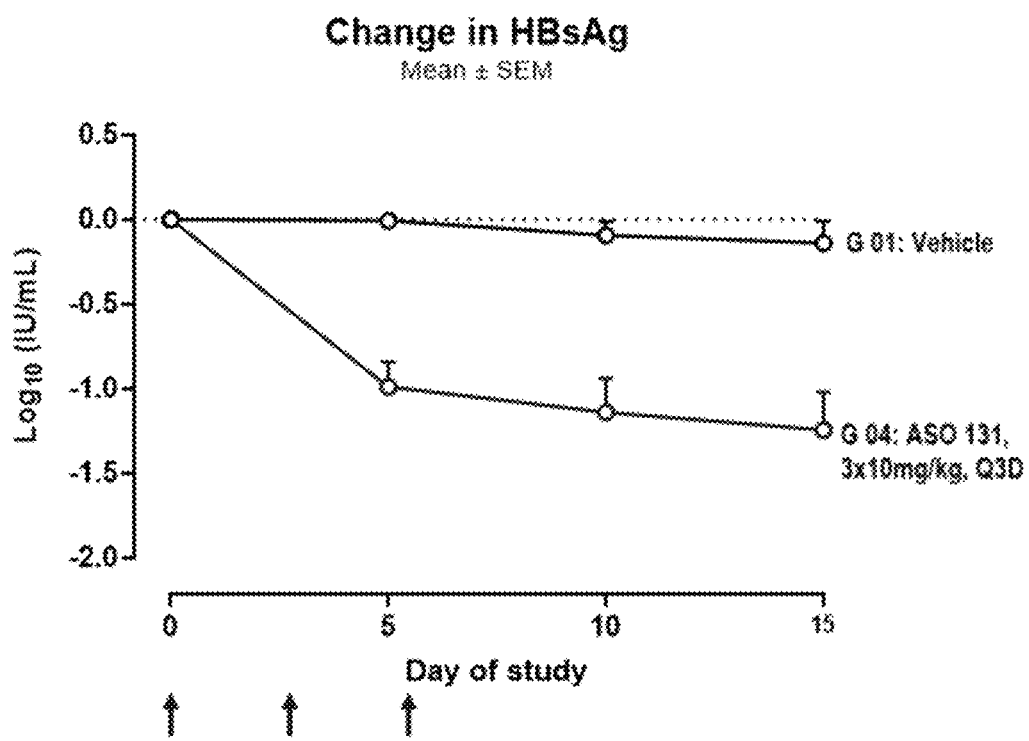
FIG. 7A shows a graph of the change in serum HBsAg from mice treated with 3×10 mg/kg Q3D of ASO 131.
Figure 7B:
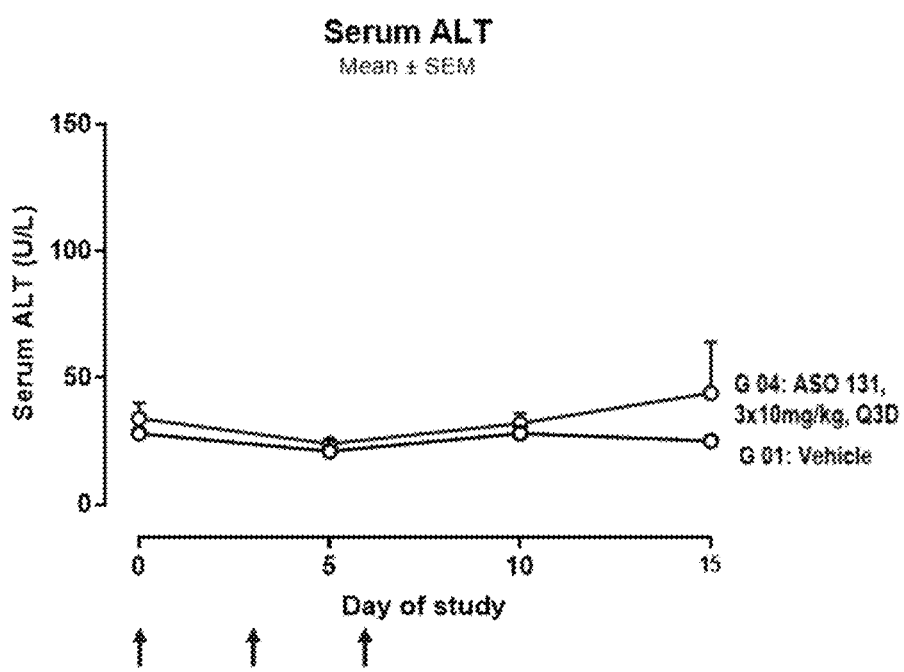
FIG. 7B shows a graph of the serum ALT from mice treated with 3×10 mg/kg Q3D of ASO 131.

ASO 131 was synthesized on ABI 394 and Expedite 8909 synthesizers using standard phosphoramidite chemistry and conjugated to GalNac4. ASO 131 was tested at a dose of 3×10 mg/kg every 3 days in the adeno-associated virus (AAV)-HBV mouse model. FIG. 7A shows a graph of the change in serum HBsAg from mice treated with 3×10 mg/kg Q3D of ASO 131. FIG. 7B shows a graph of the serum ALT from mice treated with 3×10 mg/kg Q3D of ASO 131. These results demonstrate that Luxna Chemistry modifications at wing and gap can produce a robust, durable response with no ALT elevation.

Example 19. Evaluation of ASO 121 in AAV-HBV Mouse Model

Figure 8A:
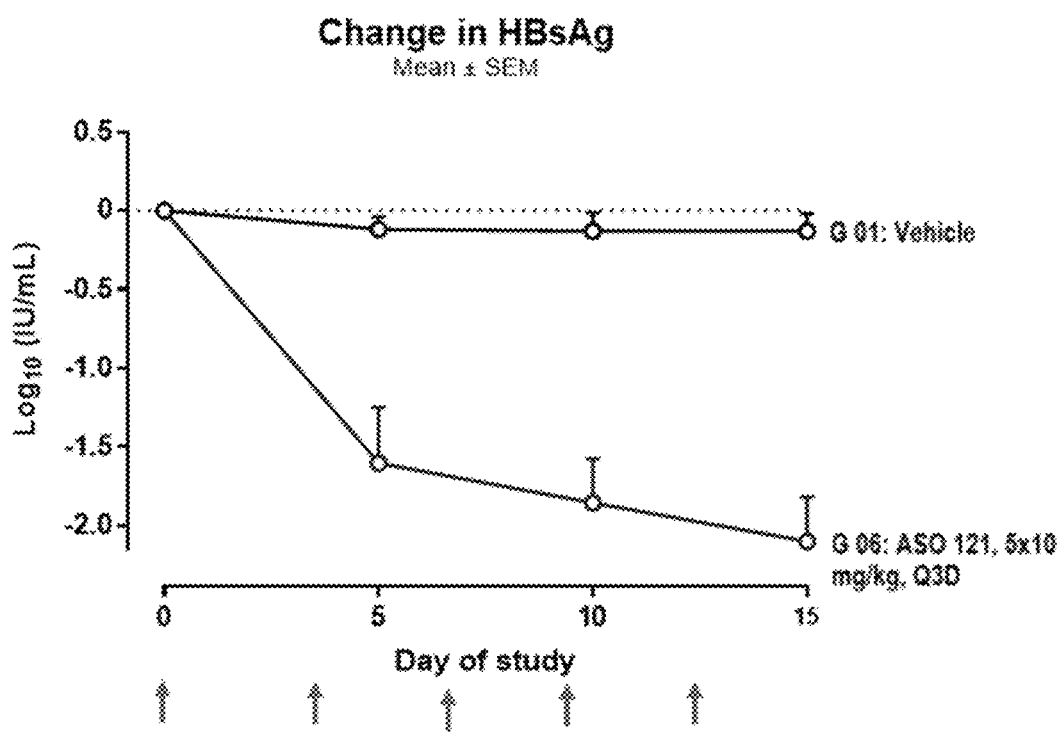
FIG. 8A shows a graph of the change in serum HBsAg from mice treated with 5×10 mg/kg Q3D of ASO 121.
Figure 8B:
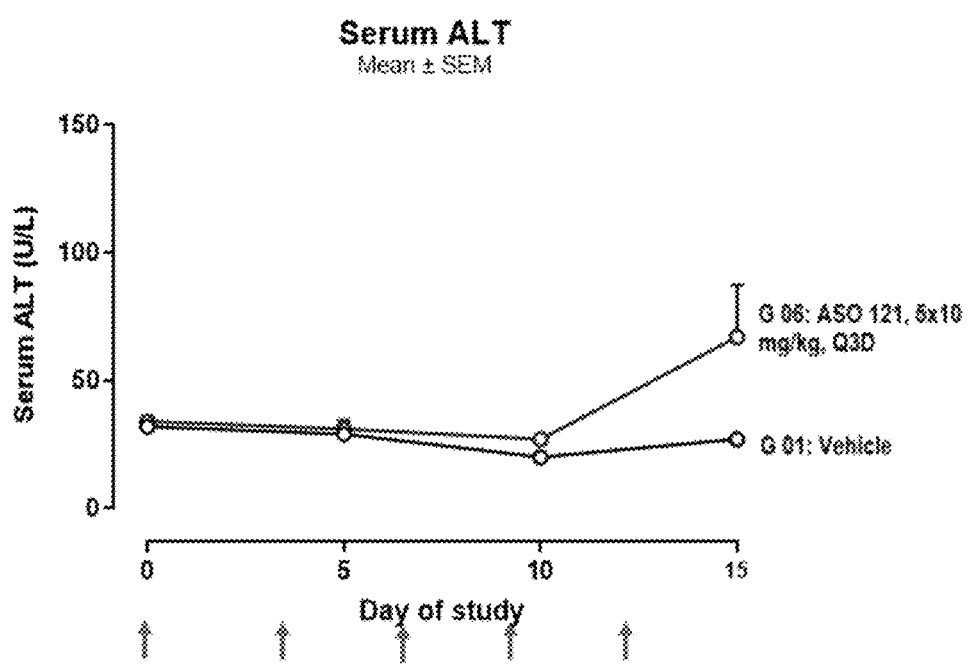
FIG. 8B shows a graph of the serum ALT from mice treated with 5×10 mg/kg Q3D of ASO 121.

ASO 121 was synthesized on ABI 394 and Expedite 8909 synthesizers using standard phosphoramidite chemistry and conjugated to GalNac4. ASO 121 was tested at a dose of 5×10 mg/kg every 3 days in the adeno-associated virus (AAV)-HBV mouse model. FIG. 8A shows a graph of the change in serum HBsAg from mice treated with 5×10 mg/kg Q3D of ASO 121. FIG. 8B shows a graph of the serum ALT from mice treated with 5×10 mg/kg Q3D of ASO 121. These results demonstrate that under very stringent dosing regimen of 3×10 mg/kg Q3D Luxna modifications at wing and gap can produce a robust, durable response with much ALT elevation.

Example 20. Evaluation of ASO Modifications

In this example, modifications (LNA or gap-modified chemistries) of various nucleotide positions in the ASO were screened for potency and toxicity.

The following specific sequences in Table 19 are within the scope of the present disclosure. As used herein, ln=Locked nucleic acid (LNA); lnA=Locked nucleic acid (LNA) A; ln(5m)C ln(5m)C=Locked nucleic acid (LNA)-5methyl C; lnG=Locked nucleic acid (LNA) G; lnT=Locked nucleic acid (LNA) T; (5m)C=5 methylC; mA=2-O-methoxy A; mU=2-O-methoxy U; (8nh)A=8-amino A; (8nh)G=8-amino G; (2s)T=2-thio T; am=amNA; am(5m)C=AmNA-NCH$_3$-(5m)C phosphoramidite; cp=scp=cyclopropyl; cpC=scpC=cyclopropyl C; cpG=scpG=cyclopropyl G; A=dA; G=dG, C=dC, T=Thymidine; cpT=scpT=cyclopropyl T; ps=phosphorothioate linkages; p=phosphodiester linkage

TABLE 19

ASO Modifications

| SEQ ID NO. | ASO # | Sequence (5'→3') |
|---|---|---|
| 272 | 132 | 5'-GalNAc1-C6-p-CA-lnGpslnApslnGpsApsGpsGpsTpsGps(5m)CpsGps(5m)Cps(5m)Cps(5m)Cpsln(5m)CpslnGpslnT 3' |
| 302 | 133 | 5'-GalNAc5-(PS)2-p-lnGpslnApslnGpsApsGpsGpsTpsGps(5m)CpsGps(5m)Cps(5m)Cps(5m)Cpsln(5m)CpslnGpslnT 3' |
| 303 | 134 | 5'-GalNAc5-(PS)2-p-lnGpslnApslnGpsApsGpsGpsTpsGps(5m)CpsGps(5m)Cps(5m)Cps(5m)Cpsln(5m)CpslnGpsAmT 3' |
| 304 | 135 | 5'-GalNAc5-(PS)2-p-lnGpslnApslnGpsApsGpsGpsTpsGps(5m)CpsGps(5m)Cps(5m)Cps(5m)Cps Am(5m)CpslnGpslnT 3' |
| 300 | 136 | 5'-GalNAc5-(PS)2-p-lnGpslnApslnGpsApsGpsGpsTpsGps(5m)CpsGps(5m)Cps(5m)Cps(5m)Cpsln(5m)CpslnGpscpT 3' |
| 408 | 137A | 5'-GalNAc5-(PS)2-p-lnGpslnApslnGpsApsGpsGpsTpsGps(5m)CpsGps(5m)Cps(5m)Cps(5m)Cps(5m)scpCpslnGpslnT 3' |
| 409 | 138 | 5'-GalNAc6-(PS)2-p-lnGpslnGpslnApsTpsTps(5m)CpsApsGps(5m)CpsGps(5m)Cps(5m)CpsGpsln Apsln(5m)CpslnG 3' |
| 410 | 132A | 5'-GalNAc5-(PS)2-p-lnGpslnApslnGpsApsGpsGpsTpsGps(5m)CpsGps(5m)Cps(5m)Cps(5m)Cpsln(5m)CpslnGpslnT 3' |

TABLE 19-continued

ASO Modifications

| SEQ ID NO. | ASO # | Sequence (5'→3') |
|---|---|---|
| 411 | 140 | 5'-GalNAc1-C6-p-CA-lnGpslnApslnTpslnApslnAps(8nh)ApsAps(5m)CpsGps(5m)Cps(5m)CpsGps(5m)CpslnApslnGpslnApsln(5m)C-3' |
| 412 | 141 | 5'-GalNAc1-C6-p-CA-lnGpslnApslnTpslnApslnApsAps(8nh)Aps(5m)CpsGps(5m)Cps(5m)CpsGps(5m)CpslnApslnGpslnApsln(5m)C-3' |
| 413 | 142 | 5'-GalNAc1-C6-p-CA-lnGpslnApslnTpslnApslnApsApsAps(5OH)CpsGps(5m)Cps(5m)CpsGps(5m)CpslnApslnGpslnApsln(5m)C-3' |
| 369 | 143 | 5'-ln(5m)Cpsam(5m)CpslnApsln(5m)Cps(5m)CpsAps(5m)CpsGpsApsGpsTps(5m)CpsTpsApslnGpslnApsln(5m)C-A-p-(PS)2-GalNAc4-3' |
| 370 | 144 | 5'-am(5m)Cpsln(5m)CpslnApsln(5m)Cps(5m)CpsAps(5m)CpsGpsApsGpsTps(5m)CpsTpsApslnGpslnApsln(5m)C-A-p-(PS)2-GalNAc4-3' |
| 414 | 145A | 5'-am(5m)Cpsln(5m)CpslnApsln(5m)Cps(5m)CpsAps(5m)CpsGpsApsGpsTps(5m)CpsTpsApslnGpslnApsln(5m)C-A-p-(PS)2-GalNAc4 3' |
| 371 | 146 | 5'-ln(5m)Cpsln(5m)CpslnApsam(5m)Cps(5m)CpsAps(5m)CpsGpsApsGpsTps(5m)CpsTpsApslnGpslnApsln(5m)C-A-p-(PS)2-GalNAc4 3' |
| 270 | 147 | 5'-GalNAc2-C6-p-CAlnApslnGpsln(5m)CpsGpsApsApsGpsTpsGps(5m)CpsAps(5m)CpsApsln(5m)CpslnGpslnG-3 |
| 415 | 148 | 5'-GalNAc1-C6-p-CA-ln(5m)Cpsln(5m)CpslnApsln(5m)Cps(5OH)CpsAps(5m)CpsGpsApsGpsTps(5m)CpsTpsApslnGpslnApsln(5m)C 3' |
| 416 | 149 | 5'-GalNAc1-C6-p-CA-ln(5m)Cpsln(5m)CpslnApsln(5m)Cps(5m)Cps(8nh)Aps(5m)CpsGpsApsGpsTps(5m)CpsTpsApslnGpslnApsln(5m)C 3' |
| 417 | 150 | 5'-GalNAc1-C6-p-CA-ln(5m)Cpsln(5m)CpslnApsln(5m)Cps(5m)CpsAps(5OH)CpsGpsApsGpsTps(5m)CpsTpsApslnGpslnApsln(5m)C 3' |
| 284 | 151 | 5'-GalNAc6-(PS)2-p-lnGpslnGpslnApsTpsTps(5m)CpsApsGps(5m)CpsGps(5m)Cps(5m)CpsGpslnApsln(5m)CpslnG 3' |
| 286 | 152 | 5'-GalNAc6-(PS)2-p-lnGpslnGpslnAps(2s)TpsTps(5m)CpsApsGps(5m)CpsGps(5m)Cps(5m)CpsGpslnApsln(5m)CpslnG 3' |
| 287 | 153 | 5'-GalNAc6-(PS)2-p-lnGpslnGpslnApsTps(2s)Tps(5m)CpsApsGps(5m)CpsGps(5m)Cps(5m)CpsGpslnApsln(5m)CpslnG 3' |
| 288 | 154 | 5'-GalNAc6-(PS)2-p-lnGpslnGpslnApsTpsTps(5oh)CpsApsGps(5m)CpsGps(5m)Cps(5m)CpsGpslnApsln(5m)CpslnG 3' |
| 378 | 155 | 5'nGpslnGpslnApsTps(2s)Tps(5m)CpsApsGps(5m)CpsGps(5m)Cps(5m)CpsGpslnApscp(5m)CpslnG-A-p-(PS)2-GalNAc6-3' |
| 377 | 156 | 5'nGpslnGpslnApsTpsTps(5Oh)CpsApsGps(5m)CpsGps(5m)Cps(5m)CpsGpslnApscp(5m)CpslnG-A-p-(PS)2-GalNAc4-3' |
| 392 | 157 | 5'-lnGpslnApslnTpsTps(5OH)CpsApsGps(5m)CpsGps(5m)Cps(5m)CpsGpsApsln(5m)CpslnGpslnGpscpG-T-p-(PS)2-GalNAc4-3' |
| 393 | 158 | 5'-lnGpslnApscpTps(2s)Tps(5m)CpsApsGps(5m)CpsGps(5m)Cps(5m)CpsGpsApsln(5m)CpslnGpslnGpslnG-T-p-(PS)2-GalNAc4-3' |

TABLE 19-continued

ASO Modifications

| SEQ ID NO. | ASO # | Sequence (5'→3') |
|---|---|---|
| 394 | 159 | 5'-lnGpslnApscpTpsTps(5m)Cps(8nh)ApsGps(5m)CpsGps(5m)Cps(5m)CpsGps Apsln(5m)CpslnGpslnGpslnG-T-p-(PS)2-GalNAc4-3' |

Figure 10A:
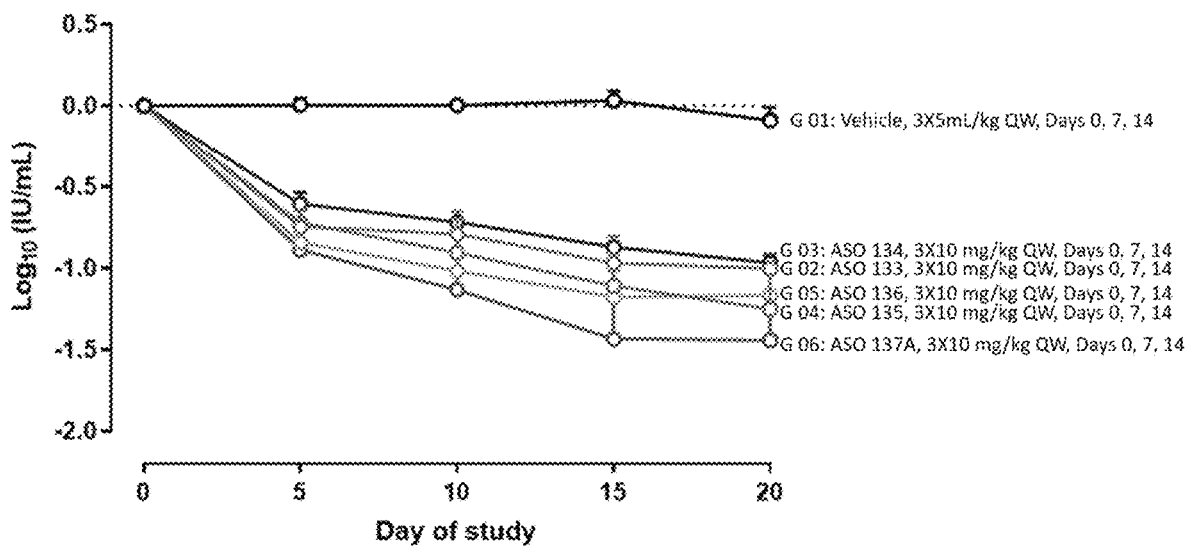
FIG. 10A shows a graph of the change in serum HBsAg from mice treated with 3×10 mg/kg QW of ASOs 133-136 and 137A.
Figure 10B:
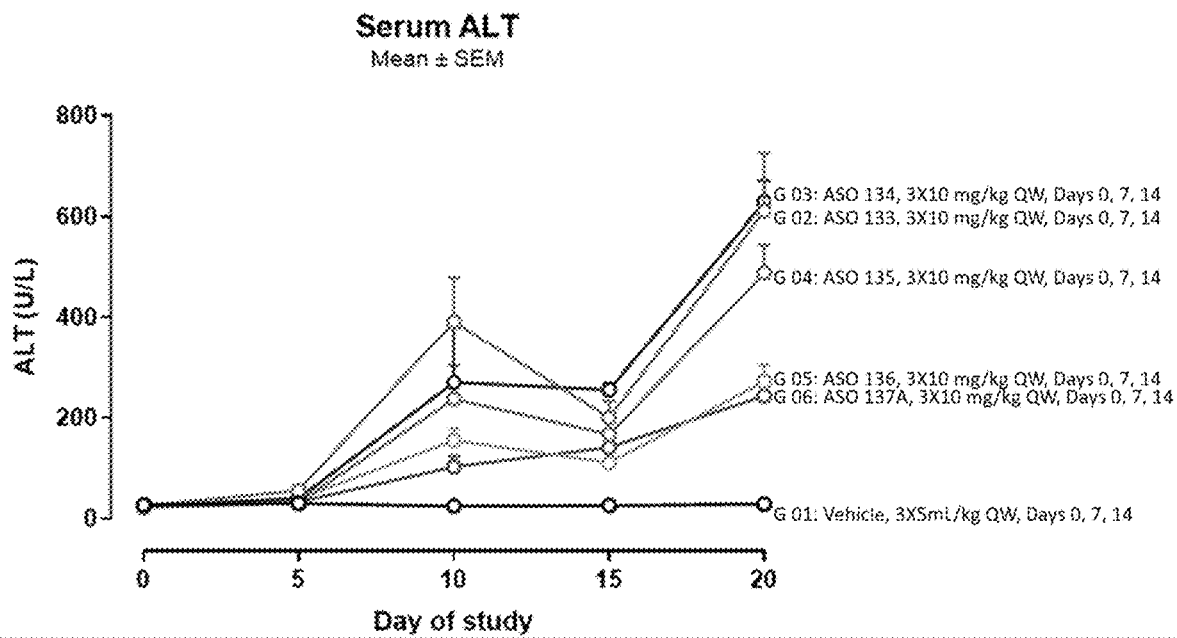
FIG. 10B shows a graph of the serum ALT from mice treated with 3×10 mg/kg QW of ASOs 133-136 and 137A.

HBV mice were treated with ASOs 133-136, and 137A at a dose of 3×10 mg/kg QW. The resulting change in serum HBsAg is shown in FIG. 10A and serum ALT is shown in FIG. 10B. These results demonstrate that for this specific sequence, ASO Wing with (5m)cpC Luxna modification (ASO 137A) has higher potency and lower ALT than all LNA (no Luxna chemistry, ASO 133), cpT modified (ASO 136), AmT modified (ASO 134) and AM(5m)C (ASO 135).

Figure 11A:
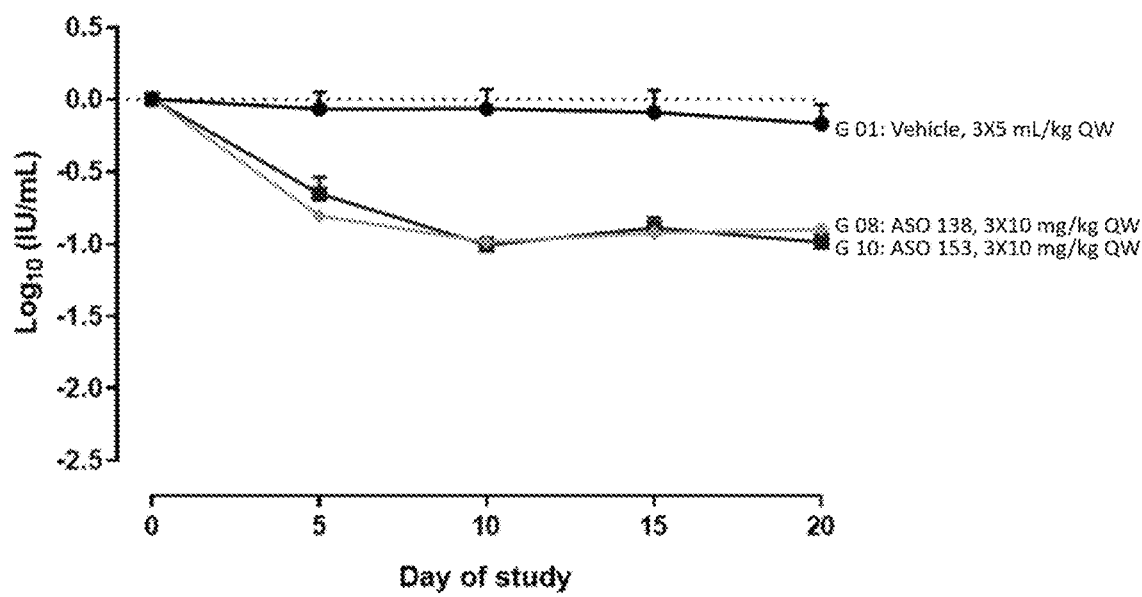
FIG. 11A shows a graph of the change in serum HBsAg from mice treated with 3×10 mg/kg QW of ASOs 138 or 153.
Figure 11B:
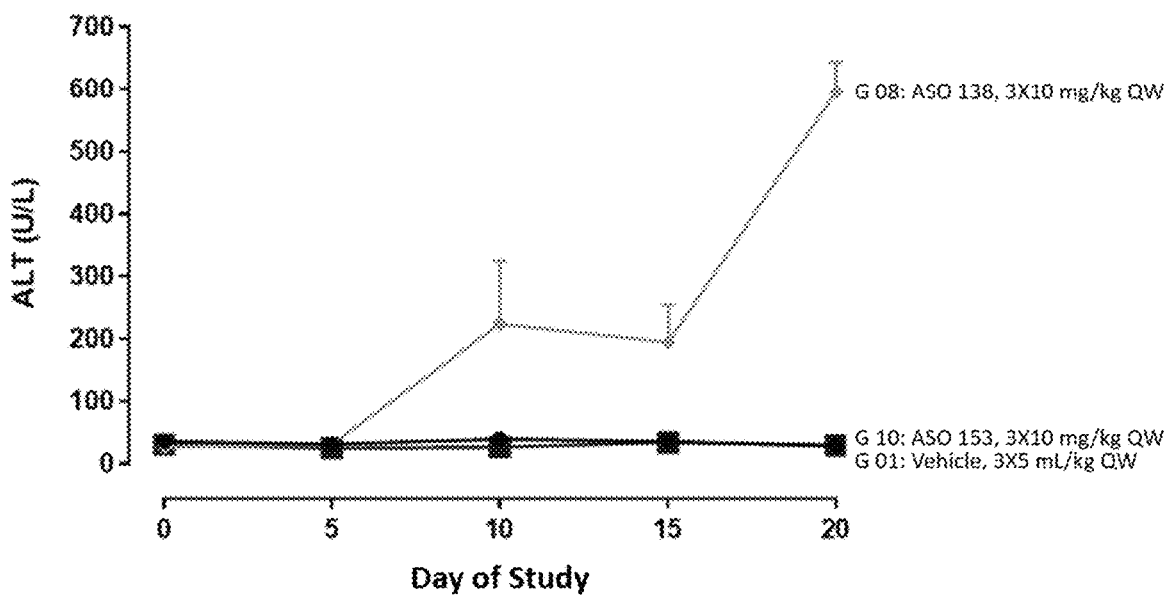
FIG. 11B shows a graph of the serum ALT from mice treated with 3×10 mg/kg QW of ASOs 138 or 153.

HBV mice were treated with ASOs 138 or 153 at a dose of 3×10 mg/kg QW. FIG. 11A shows a graph of the change in serum HBsAg from mice treated with 3×10 mg/kg QW of ASOs 138 or 153. FIG. 11B shows a graph of serum ALT from mice treated with 3×10 mg/kg QW of ASOs 138 or 153. These results demonstrate that ASOs with an Luxna modification in the central ("gap") region, Gap position #2 with (2s)T, can eliminate ALT, while maintaining potency.

Figure 12A:
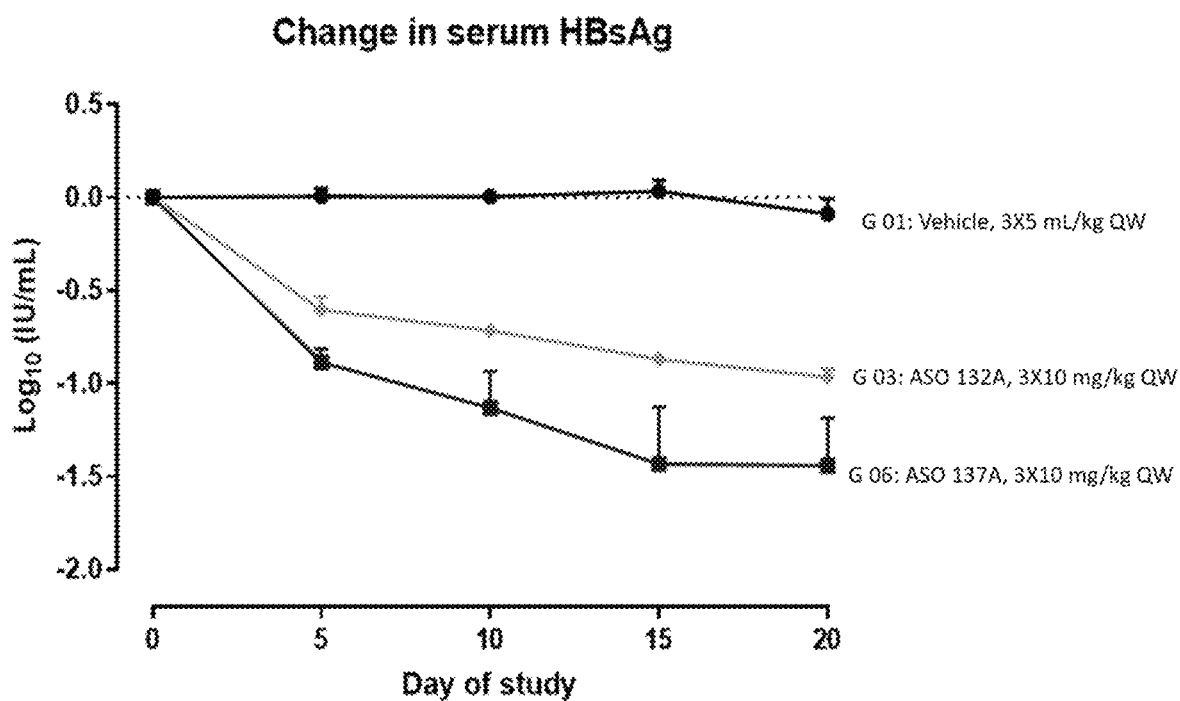
FIG. 12A shows a graph of the change in serum HBsAg from mice treated with 3×10 mg/kg QW of ASOs 132A or 137A.
Figure 12B:
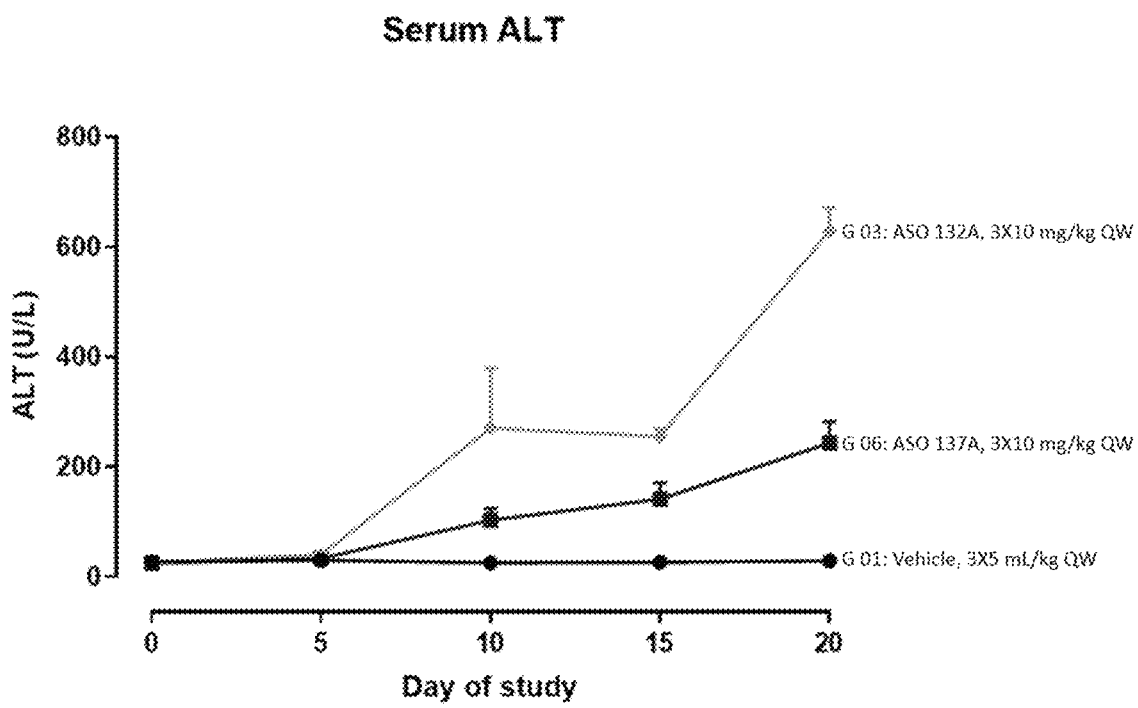
FIG. 12B shows a graph of the serum ALT from mice treated with 3×10 mg/kg QW of ASOs 132A or 137A.

HBV mice were treated with ASOs 132A or 137A at a dose of 3×10 mg/kg QW. FIG. 12A shows a graph of the change in serum HBsAg from mice treated with 3×10 mg/kg QW of ASOs 132A or 137A. FIG. 12B shows a graph of the serum ALT from mice treated with 3×10 mg/kg QW of ASOs 132A or 137A. These results demonstrate that ASOs with an Luxna Chemistry (5m)cpC modification in the wing region can reduce ALT, while improving potency from all LNA (wings) ASO.

Figure 13A:
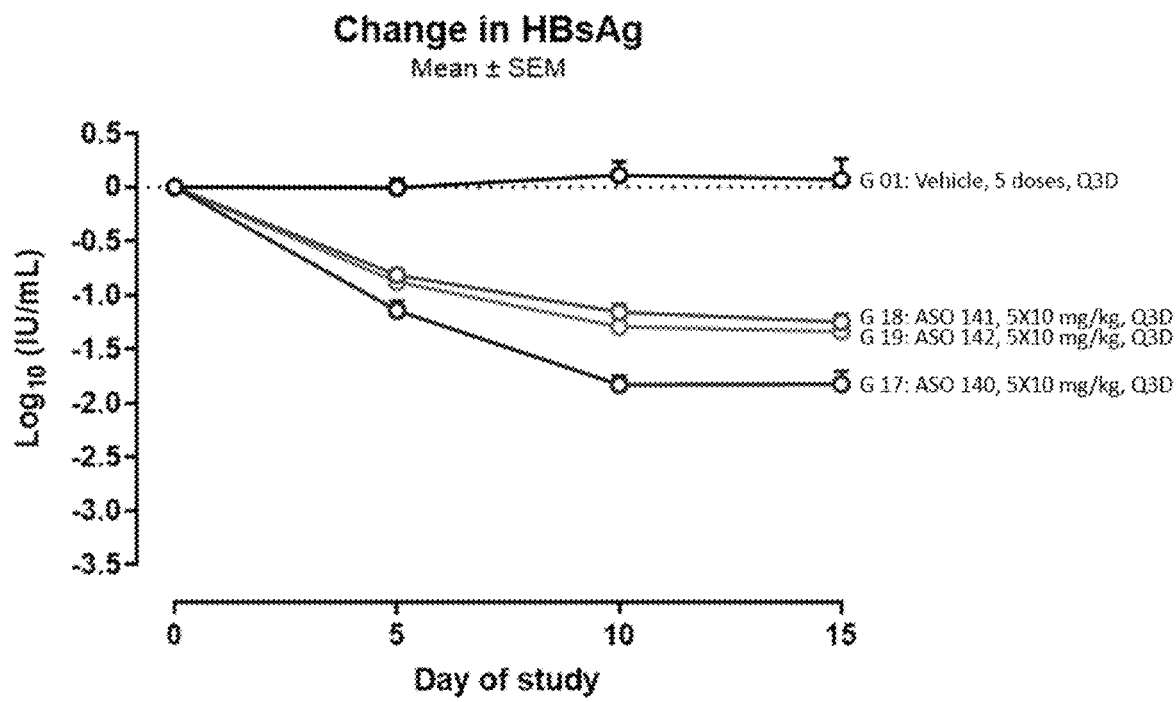
FIG. 13A shows a graph of the change in serum HBsAg from mice treated with 5×10 mg/kg Q3D of ASOs 140-142.
Figure 13B:
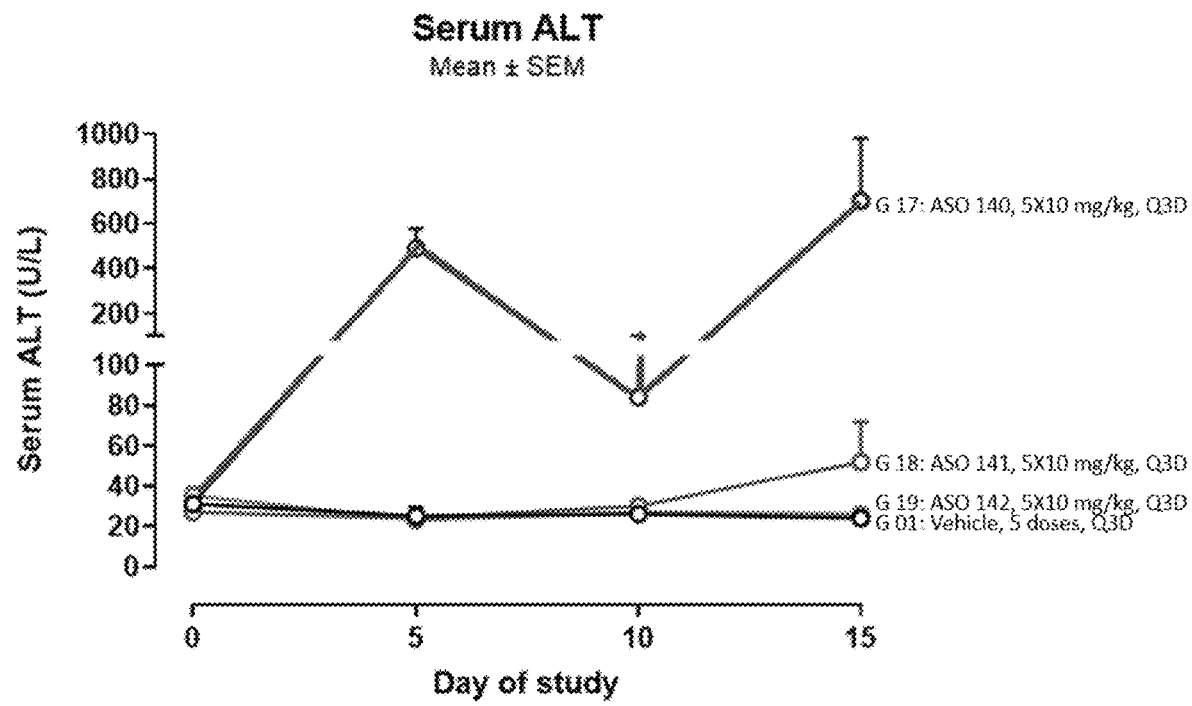
FIG. 13B shows a graph of the serum ALT from mice treated with 5×10 mg/kg Q3D of ASOs 140-142.

HBV mice were treated with ASOs 140-142 a dose of 5×10 mg/kg Q3D. FIG. 13A shows a graph of the change in serum HBsAg from mice treated with 5×10 mg/kg Q3D of ASOs 140-142. FIG. 13B shows a graph of the serum ALT from mice treated with 5×10 mg/kg Q3D of ASOs 140-142. All 3 sequences have all LNA in the wings but have 8-amino A, 8-amino A, or (5-OH)C at position #1 (ASO 140), #2 (ASO 141) and #3 (ASO 142) from the 5' end of the gap (e.g., central region), respectively. ASO 142 with (5-OH)C at #3 position of gap has no ALT elevation and good potency. These results demonstrate that ASOs with modifications in the central region can reduce or eliminate ALT, while maintaining potency.

Figure 14A:
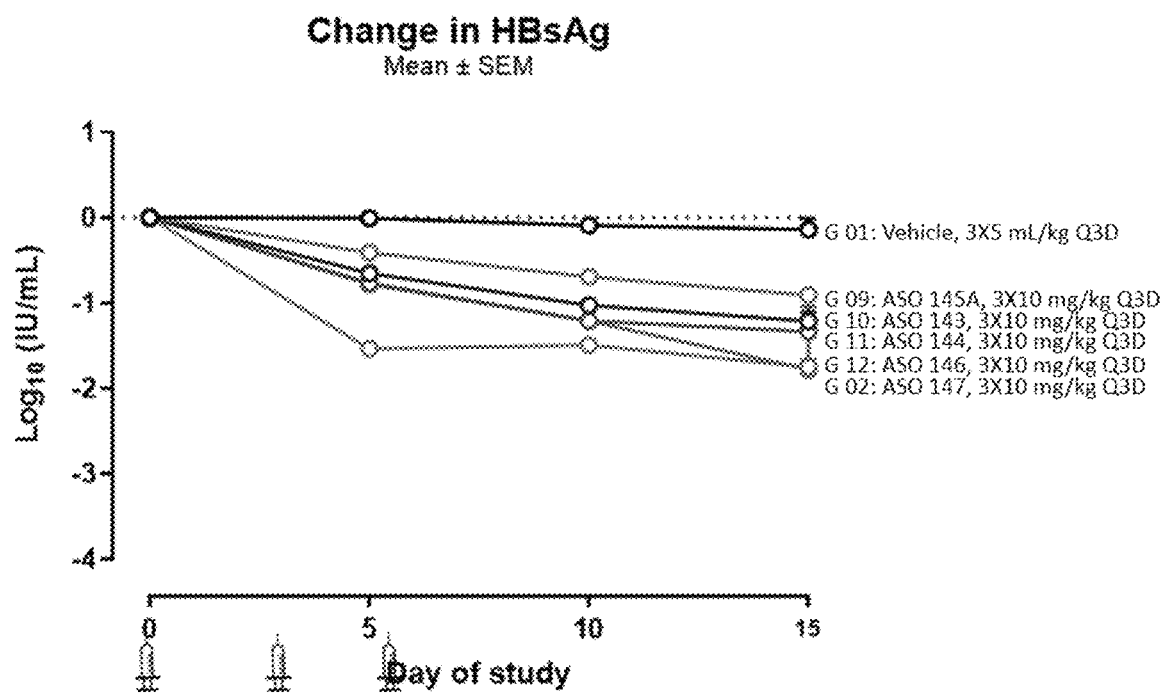
FIG. 14A shows a graph of the change in serum HBsAg from mice treated with 3×10 mg/kg Q3D of ASOs 143, 144, 145A, or 146.
Figure 14B:
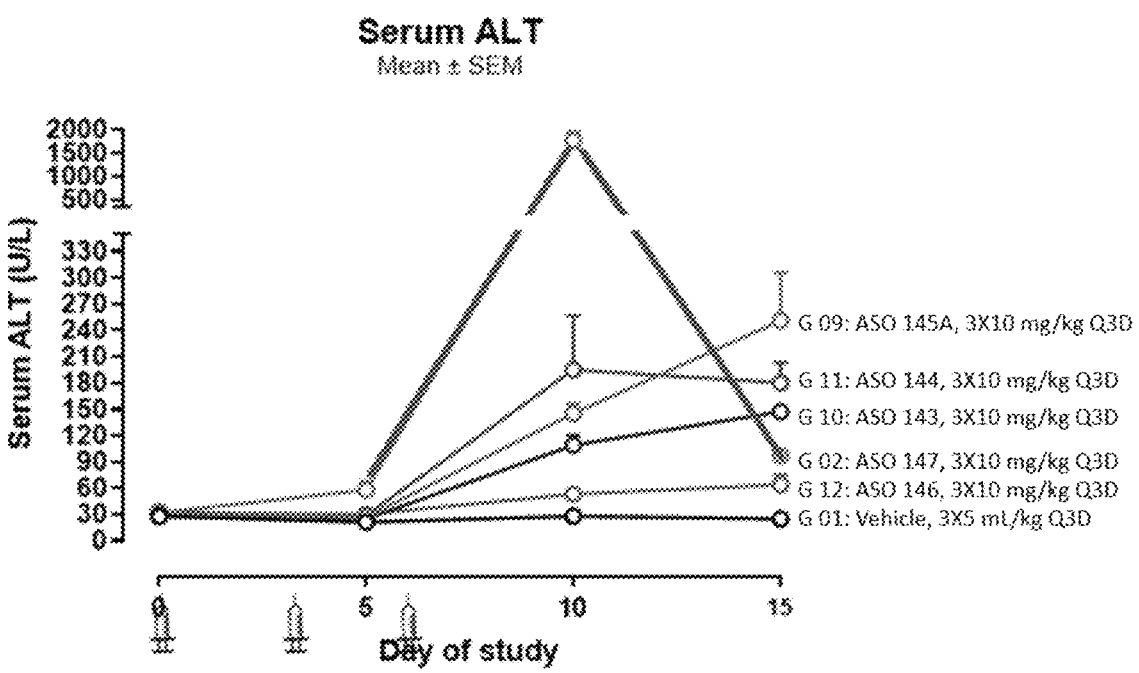
FIG. 14B shows a graph of the serum ALT from mice treated 3×10 mg/kg Q3D of ASOs 143, 144, 145A, or 146.

HBV mice were treated with ASOs 143, 144, 145A, or 146 a dose of 3×10 mg/kg Q3D. FIG. 14A shows a graph of the change in serum HBsAg from mice treated with 3×10 mg/kg Q3D of ASOs 143, 144, 145A, or 146. FIG. 14B shows a graph of the serum ALT from mice treated 3×10 mg/kg Q3D of ASOs 143, 144, 145A, or 146. These sequences were designed by using Am(5m)C to "walk" the sequence, replacing ln(5m)C one by one. These results demonstrate that ASO with Am(5m)C modification in the end of 5' wing has best therapeutic index comparing with Am(5m)C at other positions.

Figure 15A:
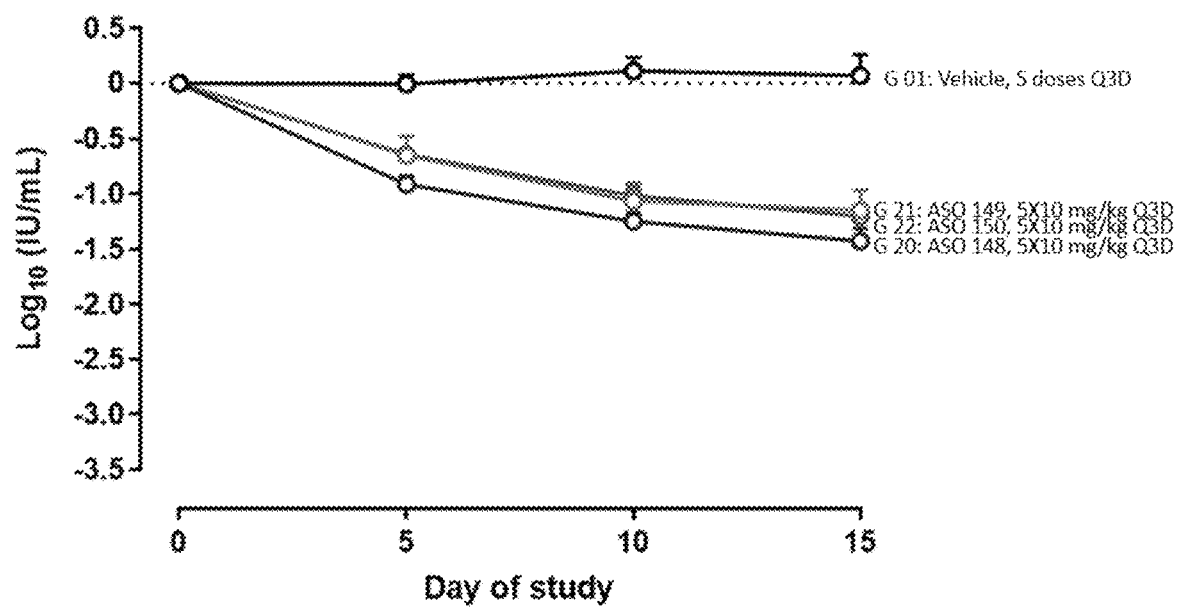
FIG. 15A shows a graph of the change in serum HBsAg from mice treated with 5×10 mg/kg Q3D of ASOs 148-150.
Figure 15B:
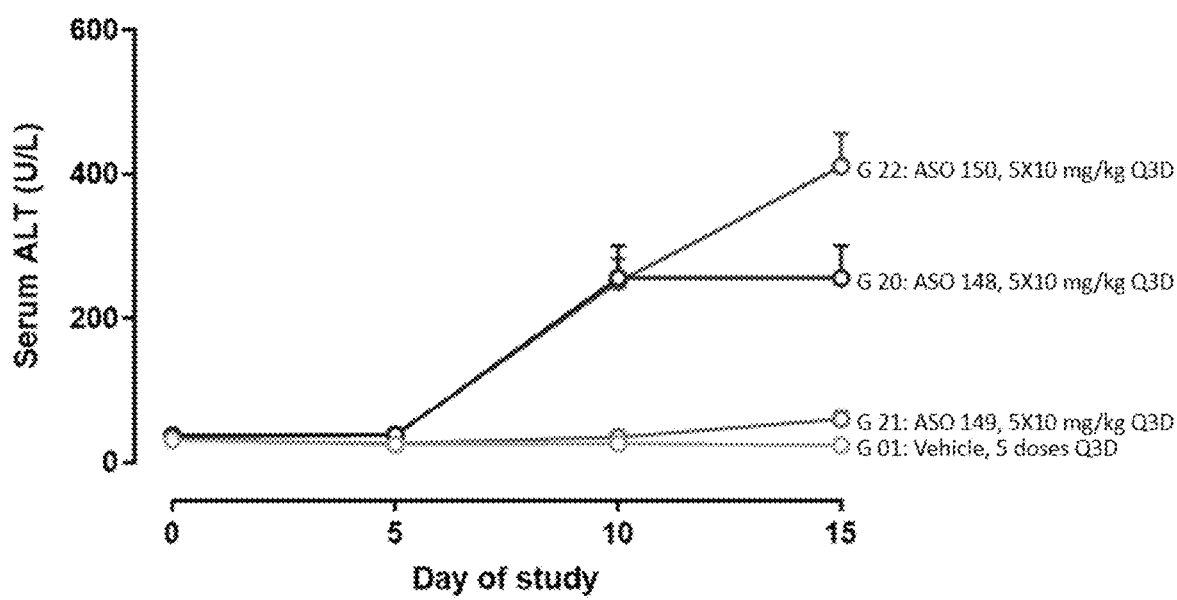
FIG. 15B shows a graph of the serum ALT from mice treated with 5×10 mg/kg Q3D of ASOs 148-150.

HBV mice were treated with ASOs 148-150 a dose of 5×10 mg/kg Q3D. FIG. 15A shows a graph of the change in serum HBsAg from mice treated with 5×10 mg/kg Q3D of ASOs 148-150. FIG. 15B shows a graph of the serum ALT from mice treated with 5×10 mg/kg Q3D of ASOs 148-150. These sequences have all LNA wings, but with Luxna Gap modification at position #1 (ASO 148); #2 (ASO 149) and #3 (ASL 150) from the 5' end of the central region, respectively. These results demonstrate that for this sequence, ASO with Luxna modification in the Gap #2 position has the best therapeutic index.

Figure 16A:
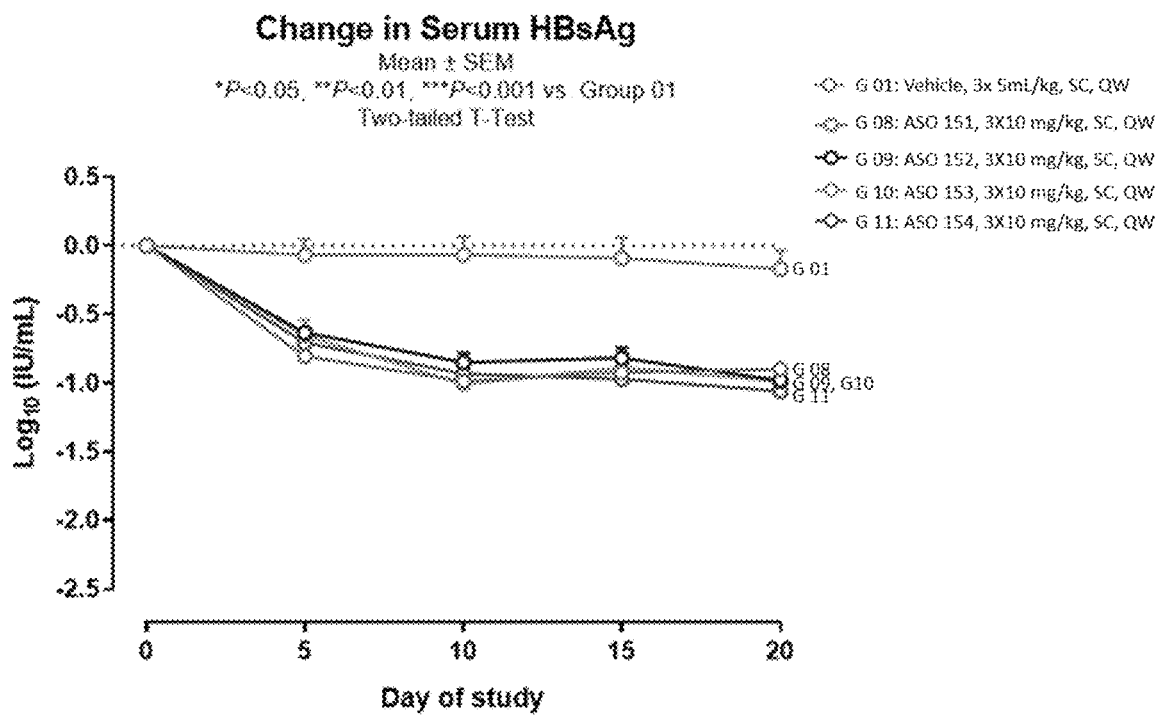
FIG. 16A shows a graph of the change in serum HBsAg from mice treated with 3×10 mg/kg QW of ASOs 151-154.
Figure 16B:
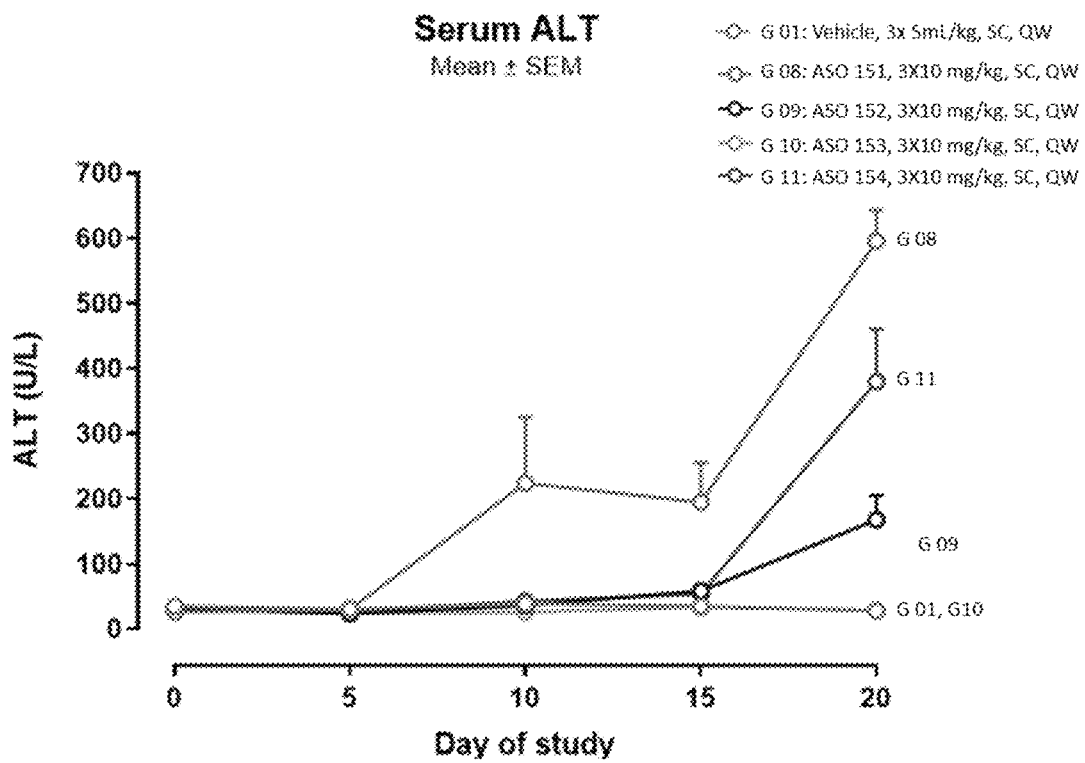
FIG. 16B shows a graph of the serum ALT from mice treated with 3×10 mg/kg QW of ASOs 151-154.

HBV mice were treated with ASOs 151-154 a dose of 3×10 mg/kg, SC, QW. FIG. 16A shows a graph of the change in serum HBsAg from mice treated with QW 3×10 mg/kg of ASOs 151-154. FIG. 16B shows a graph of the serum ALT from mice treated with QW 3×10 mg/kg of ASOs 151-154. These sequences have all LNA wings, but with no Luxna chemistry modification (ASO 151), Luxna Gap modification at #1 (ASO 152); #2 (ASO 153) and #3 (ASO 154) respectively. These results demonstrate that ASOs with Luxna gap modifications (ASOs 152, 153 and 154) in the central region can reduce or eliminate ALT from ASO without Luxna gap modification (ASO 151), while maintaining potency. Among ASOs 152, 153 and 154, ASO 153 with Luxna modification at Gap position #2 has no ALT elevation.

Figure 17A:
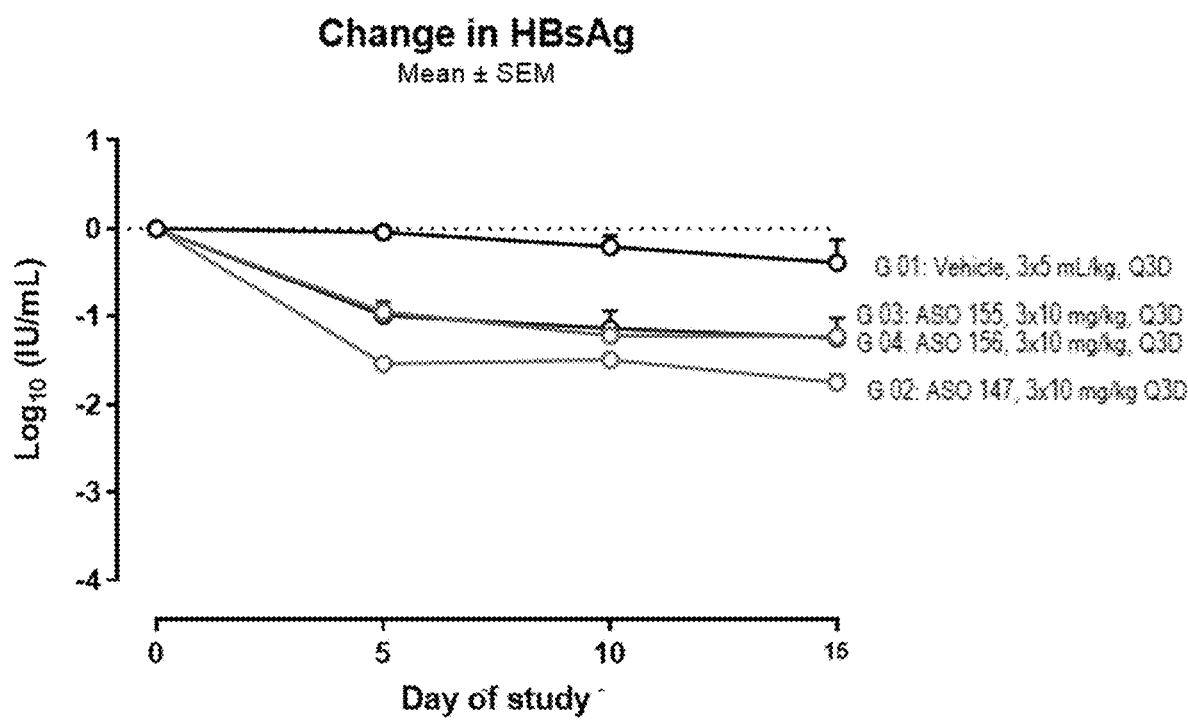
FIG. 17A shows a graph of the change in serum HBsAg from mice treated with 3×10 mg/kg Q3D of ASOs 147, 155, or 156.
Figure 17B:
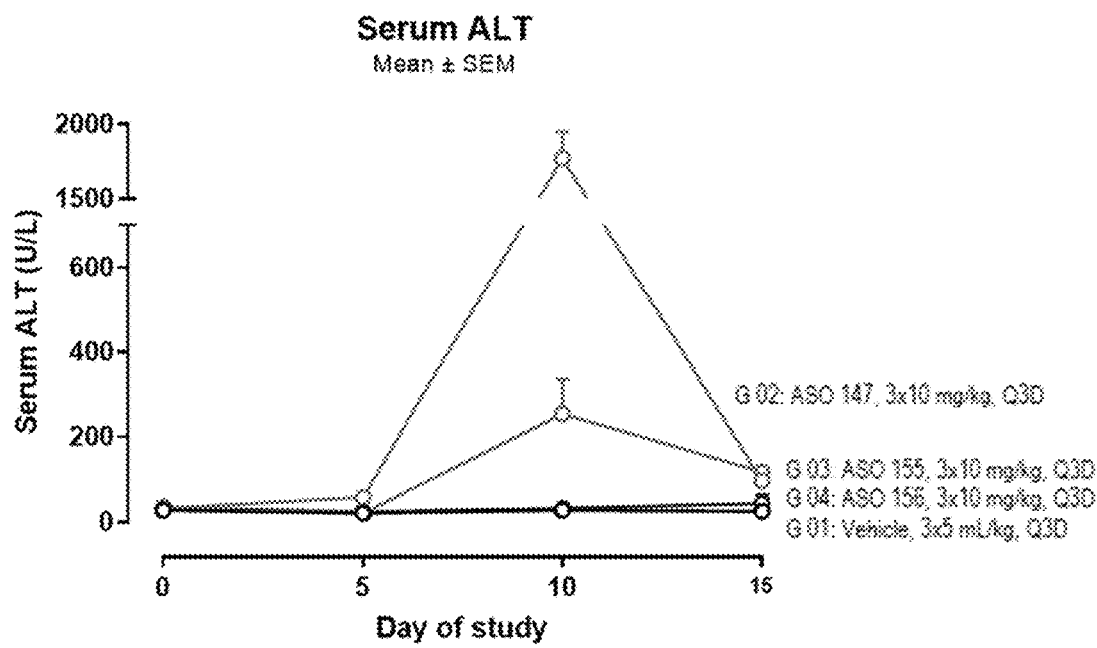
FIG. 17B shows a graph of the serum ALT from mice treated with 3×10 mg/kg Q3D of ASOs 147, 155, or 156.

HBV mice were treated with ASOs 147, 155, or 156 a dose of 3×10 mg/kg, SC, Q3D. FIG. 17A shows a graph of the change in serum HBsAg from mice treated with 3×10 mg/kg Q3D of ASOs 147, 155, or 156. FIG. 17B shows a graph of the serum ALT from mice treated with 3×10 mg/kg Q3D of ASOs 147, 155, or 156. ASO 155 and 156 have same Luxna wing modification but different gap modifications. ASO 155 has Luxna gap modification at #2 position and 156 has Luxna gap modification at #3 position. These results demonstrate that while both ASOs with Luxna modifications can reduce or eliminate ALT, modification at #2 gap position worked better for this specific sequence.

Figure 18A:
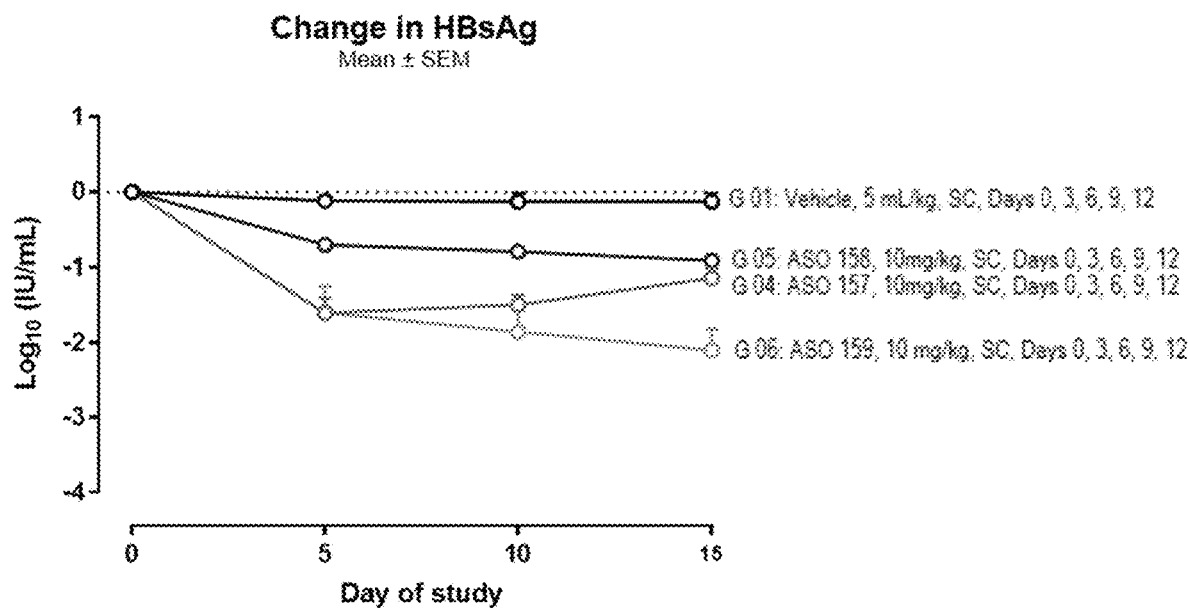
FIG. 18A shows a graph of the change in serum HBsAg from mice treated with 5×10 mg/kg Q3D of ASOs 157-159.
Figure 18B:
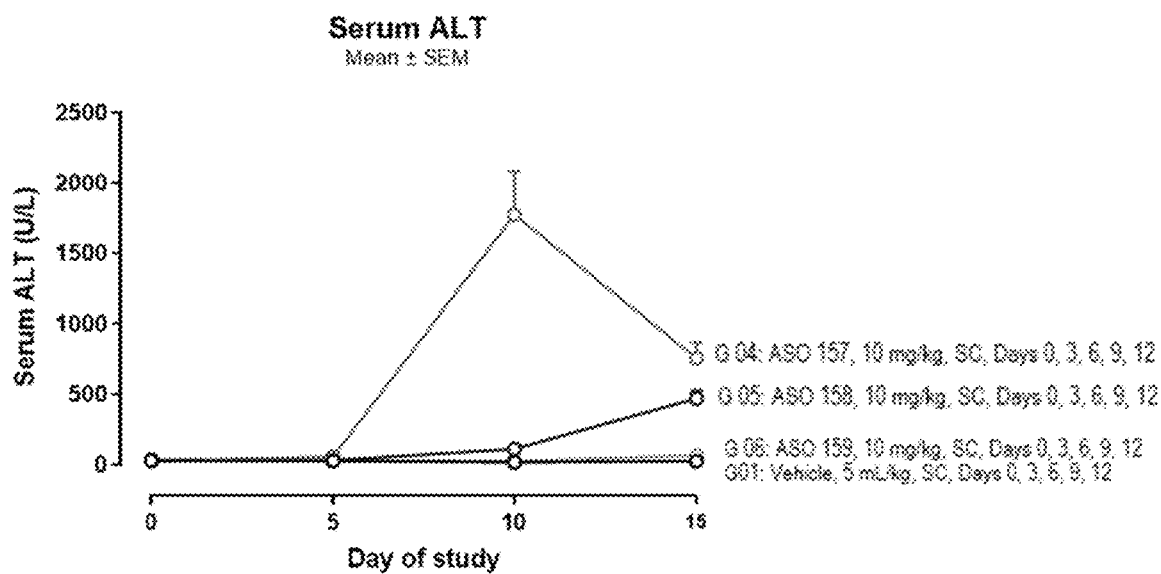
FIG. 18B shows a graph of the serum ALT from mice treated with 5×10 mg/kg Q3D of ASOs 157-159.

HBV mice were treated with ASOs 157-159 a dose of 5×10 mg/kg, SC, Q3D. FIG. 18A shows a graph of the change in serum HBsAg from mice treated with 5×10 mg/kg Q3D of ASOs 157-159. FIG. 18B shows a graph of the serum ALT from mice treated with 5×10 mg/kg Q3D of ASOs 157-159. These results demonstrate that ASO with Luxna modification at #3 position of gap and with cpT modification in the wing has best potency and safety.

| SEQ ID NO: | Description | Sequence |
|---|---|---|
| 1 | Hepatitis B virus (Genbank Accession No. KC315400.1) | ctccaccactaccaccaaactatcaagatcccagagtcagggccctgtactttcctgctggtggctcaagttc cggaacagtaaaccctgctccgactactgcctctcccatatcgtcaatcttctcgaggactggggaccctgtac cgaatatggagagcaccacatcaggattcctaggaccccctgctcgtgttacaggcggggttttcttgttgaca agaatcctcacaataccacagagtctagactcgtggtggacttctctcaattttctagggggagcacccacgtg tcctggccaaaatttgcagtccccaacctccaatcactcaccaacctcttgtcctccaatttgtcctggttatcgct ggatgtgtctgcggcgttttatcatcttcctcttcatcctgctgctatgcctcatcttcttgttggttcttctggactac caaggtatgttgcccgtttgtcctctacttccaggaacatcaactaccagcaccggaccatgcaaaacctgcac |

| SEQ ID NO: | Description | Sequence |
|---|---|---|
| | | aactactgctcaagggacctctatgtttccctcatgttgctgtacaaaacctacggacggaaactgcacctgtat<br>tcccatcccatcatcttgggctttcgcaaaatacctatgggagtgggcctcagtccgtttctcttggctcagtttac<br>tagtgccatttgttcagtggttcgtagggctttcccccactgtctggctttcagttatatggatgatgtggttttggg<br>ggcaagtctgtacaacatcttgagtccctttataccgctgttaccaattttctttttatctttgggtatacatttaaacc<br>ctcacaaaacaaaaagatggggatattccdtaacttcatgggatatgtaattgggagttggggcactttgcctc<br>aggaacatattgtacaaaaaaatcaagcaatgttttaggaaacttcctgtaaacaggcctattgattggaaagtat<br>gtcaacraattgtgggtcttttgggggtttgccgccccctttcacgcaatgtggatatcctgctttaatgcctttatatg<br>catgtatacaagctaagcaggcttttactttctcgccaacttacaaggcctttctgtgtaaacaatatctgaacctttt<br>acccgttgctcggcaacggtcaggtctttgccaagtgtttgctgacgcaacccccactggttggggcttggc<br>cataggccatcagcgcatgcgtggaacctttgtggctcctctgccgatccatactgcggaactcctagcagctt<br>gttttgctcgcagccggtctggagcaaaacttatcggcaccgacaactctgttgtcctctctcggaaatacacct<br>cctttccatggctgctaggatgtgctgccaactggatcctgcgcgggacgtcctttgtctacgtcccgtcggcg<br>ctgaatcccgcggacgacccatctcggggccgtttgggactctaccgtccccttctgcgtctgccgttccgcc<br>cgaccacggggcgcacctctctttacgcggtctcccgtctgtgccttctcatctgccggaccgtgtgcacttc<br>gcttcacctctgcacgtcgcatggagaccaccgtgaacgcccacgggaacctgcccaaggtcttgcataaga<br>ggactcttggacttcagcaatgtcaacgaccgaccttgaggcatacttcaaagactgtgtgtttactgagtggg<br>aggagttggggggaggaggttaggttaaaggtctttgtactaggaggctgtaggcataaattggtgtgttcacca<br>gcaccatgcaacttttttcacctctgcctaatcatctcatgttcatgtcctactgttcaagcctccaagctgtgcctg<br>ggtggctttgggtcatggacattgacccgtataaagaatttgtggagttctctgtgagttactctcttttttgccttct<br>gacttctttccttctattcgagatctcctcgacaccgcctctgctctgtatcgggaggcctagagtctccggaac<br>attgttcacctcaccatacggcactcaggcaagcaattctgtgttggggtgagttaatgaatctagccacctgg<br>gtgggaagtaatttggaagatccagcatccaggaattagtagtcagctatgtcaacgttaatatgggcctaaa<br>aatcagacaactattgtggtttcacattttcctgtcttacttttgggagagaaactgttcttgaatattttggtgtcttttg<br>gagtgtggattcgcactcctcctgcatatagaccacaaaatgcccctatcttatcaacacttccggaaactactg<br>ttgttagacgaagaggcaggtcccctagaagaagaactccctcgcctcgcagacgaaggtctcaatcgccg<br>cgtcgcagaagatctcaatctcgggaatctcaatgttagtattccttggacacataaggtgggaaactttacgg<br>ggctttattcttctacggtacctttgcttttaatcctaaatggcaaactccttctttttcctgacattcatttgcaggagga<br>cattgttgatagatgtaagcaattgtggggccccttcacagtaaatgaaaacaggagacttaaattaattatgcct<br>gctaggttttatcccaatgttactaaatatttgccctttagataaagggatcaaaccgtattatccagagtatgtagtt<br>aatcattacttccagacgcgacattatttacacactcttttggaaggcggggatcttatataaaagagagtccaca<br>cgtagcgcctcattttgcgggtcaccatattcttgggaacaagatctacagcatgggaggttggtcttccaaac<br>ctcgaaaaggcatggggacaaatcttctgtccccaatccctgggattcttccccgatcatcagttggaccct<br>gcattcaaagccaactcagaaaatccagattggacctcaactcacacaaggacaactggccggacgccaa<br>caaggtgggagtgggagcattcgggccagggttcacccctcctcatggggactgttggggtggagccctc<br>aggtcagggcatattcacaacagtgccagcagctcctcctcctgcctccaccaatcggcagtcaggaaggc<br>agcctactcccttctctccacctctaagagacactcatcctcaggccatgcagtggaa |

What is claimed is:

1. An antisense oligonucleotide (ASO) comprising 14-22 nucleotide units, wherein the ASO comprises:

(a) a central region (B') comprising 6 or more contiguous DNA nucleosides, wherein at least the nucleotide at position 3 from the 5' end of the central region is a modified nucleotide, and wherein at least 5 of the DNA nucleosides in the central region are connected by phosphorothioate linkages, (b) a 5'-wing region (A') comprising 2 to 6 locked nucleosides and at least one 2' substituted nucleoside, and (c) a 3'-wing region (C') comprising 3 to 6 locked nucleosides, wherein at least 3 of the locked nucleosides in the 3'-wing region are connected by phosphorothioate linkages, wherein the central region of the ASO is complementary or hybridizes to a viral target RNA sequence in an X region or an S region of HBV; and wherein at least one of the 5' wing region and the 3' wing region contains at least one locked nucleoside independently selected from scpBNA, AmNA (N—H), AmNA (N-Me), GuNA, GuNA (N—R) where R is selected from Me, Et, i-Pr, t-Bu and combinations thereof, wherein the modified nucleotide in a central region is selected from

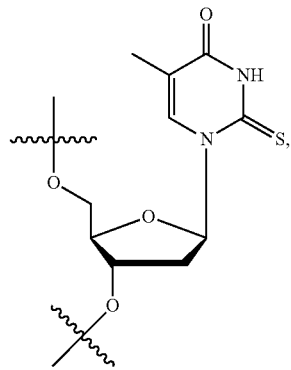

("(2s)T")

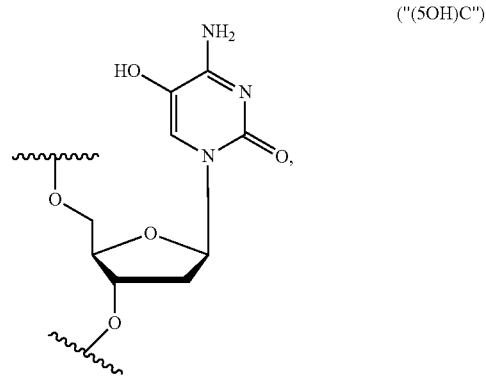

("(5OH)C")

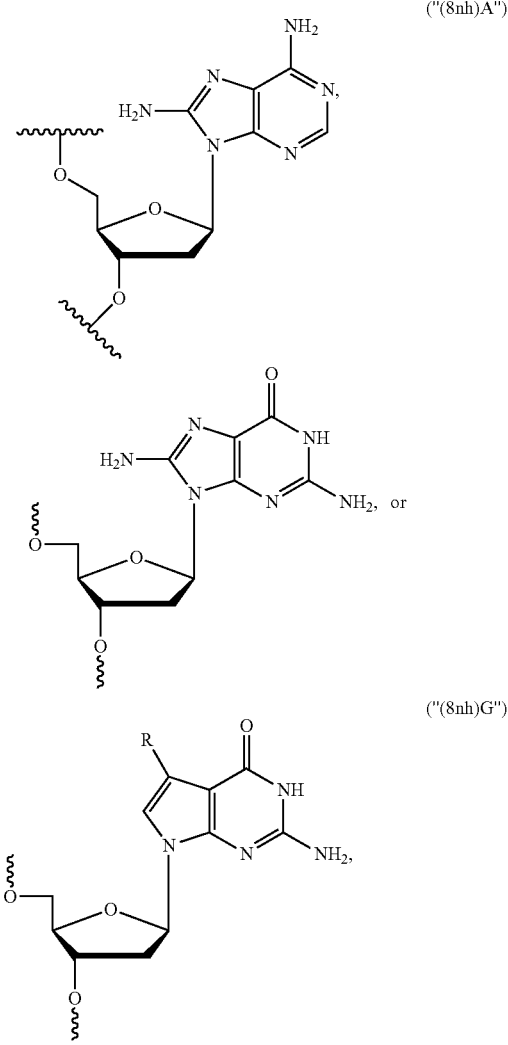

wherein:
R is a halogen or R'—C≡C—; and
R' is $C_{6-12}$ aryl, 5- to 12-membered heteroaryl, hydroxy-$C_{1-6}$alkyl, or C1-7 alkanoyloxy.

2. A pharmaceutical composition comprising an ASO according to claim 1.

3. The ASO of claim 1, wherein the 5'-wing region comprises 2 to 6 phosphorothioate-linked locked nucleosides.

4. The ASO of claim 1, wherein the 5' or 3' wing region further comprises at least one locked nucleoside independently selected from locked nucleic acid A (lnA), locked nucleic acid-5methyl C (ln(5m)C); locked nucleic acid G (lnG); locked nucleic acid T (lnT), and combinations thereof.

5. An antisense oligonucleotide (ASO) selected from:
(i) 5'-mA-lnGpslnApslnTpslnApslnApsApsAps(5oh)CpsGps(5m)Cps(5m)CpsGps(5m)CpslnApslnGpslnA pscp(5m)C-3' (SEQ ID NO: 420),
(ii) 5'-GalNac4-ps2-p-mA-lnGpslnApslnTpslnApslnApsApsAps(5oh)CpsGps(5m)Cps(5m)CpsGps(5m)CpslnApslnGpslnA pscp(5m)C-3' (SEQ ID NO: 400),
(iii) 5'-lnGpslnApslnTpslnApslnApsApsAps(5oh)CpsGps(5m)Cps(5m)CpsGps(5m)CpslnApslnGpslnA pscp(5m)C-3' (SEQ ID NO: 421),
(iv) 5'-mU-lnGpslnApscpTpsTps(5m)Cps(8nh)ApsGps(5m)CpsGps(5m)Cps(5m)CpsGpsApsln(5m)CpslnG pslnGpslnG-3' (SEQ ID NO: 422),
(v) 5'-GalNac4-ps2-p-mU-po-lnGpslnApscpTpsTps(5m)Cps(8nh)ApsGps(5m)CpsGps(5m)Cps(5m)CpsGpsApsln(5m)CpslnG pslnGpslnG-3' (SEQ ID NO: 156), and
(vi) 5'-lnGpslnApscpTpsTps(5m)Cps(8nh)ApsGps(5m)CpsGps(5m)Cps(5m)CpsGpsApsln(5m)CpslnG pslnGpslnG-3' (SEQ ID NO: 404).

6. The ASO of claim 5, wherein the ASO is 5'-mA-lnGpslnApslnTpslnApslnApsApsAps(5oh)CpsGps(5m)Cps(5m)CpsGps(5m)CpslnApslnGpslnA pscp(5m)C-3' (SEQ ID NO: 420).

7. The ASO of claim 5, wherein the ASO is 5'-GalNac4-ps2-p-mA-lnGpslnApslnTpslnApslnApsApsAps(5oh)CpsGps(5m)Cps(5m)CpsGps(5m)CpslnApslnGpslnA pscp(5m)C-3' (SEQ ID NO: 400).

8. The ASO of claim 5, wherein the ASO is 5'-lnGpslnApslnTpslnApslnApsApsAps(5oh)CpsGps(5m)Cps(5m)CpsGps(5m)CpslnApslnGpslnA pscp(5m)C-3' (SEQ ID NO: 421).

9. The ASO of claim 5, wherein the ASO is 5'-mU-lnGpslnApscpTpsTps(5m)Cps(8nh)ApsGps(5m)CpsGps(5m)Cps(5m)CpsGpsApsln(5m)CpslnG pslnGpslnG-3' (SEQ ID NO: 422).

10. The ASO of claim 5, wherein the ASO is 5'-GalNac4-ps2-p-mU-po-lnGpslnApscpTpsTps(5m)Cps(8nh)ApsGps(5m)CpsGps(5m)Cps(5m)CpsGpsApsln(5m)CpslnG pslnGpslnG-3' (SEQ ID NO: 156).

11. The ASO of claim 5, wherein the ASO is 5' lnGpslnApscpTpsTps(5m)Cps(8nh)ApsGps(5m)CpsGps(5m)Cps(5m)CpsGpsApsln(5m)CpslnG pslnGpslnG-3' (SEQ ID NO: 404).

12. The ASO of claim 1 further comprising a targeting group.

13. The ASO of claim 12, wherein the targeting group comprises a GalNAc moiety.

14. The ASO of claim 5 further comprising a targeting group.

15. The ASO of claim 14, wherein the targeting group comprises a GalNAc moiety.

16. A method of treating a subject having a Hepatitis B virus (HBV) infection, comprising administering to the subject a therapeutically effective amount of the ASO of claim 1.

* * * * *

SEQUENCE LISTING

<160> NUMBER OF SEQ ID NOS: 428

<210> SEQ ID NO 1
<211> LENGTH: 3215
<212> TYPE: DNA
<213> ORGANISM: Hepatitis B virus

<400> SEQUENCE: 1

| | | |
|---|---|---|
| ctccaccact ttccaccaaa ctcttcaaga tcccagagtc agggccctgt actttcctgc | 60 |
| tggtggctca agttccggaa cagtaaaccc tgctccgact actgcctctc ccatatcgtc | 120 |
| aatcttctcg aggactgggg accctgtacc gaatatggag agcaccacat caggattcct | 180 |
| aggaccctg ctcgtgttac aggcggggtt tttcttgttg acaagaatcc tcacaatacc | 240 |
| acagagtcta gactcgtggt ggacttctct caatttccta gggggagcac ccacgtgtcc | 300 |
| tggccaaaat tgcagtcccc caacctccaa tcactcacca acctcttgtc ctccaatttg | 360 |
| tcctggttat cgctggatgt gtctgcggcg ttttatcatc ttcctcttca tcctgctgct | 420 |
| atgcctcatc ttcttgttgg ttcttctgga ctaccaaggt atgttgcccg tttgtcctct | 480 |
| acttccagga acatcaacta ccagcaccgg accatgcaaa acctgcacaa ctactgctca | 540 |
| agggacctct atgtttccct catgttgctg tacaaaacct acggacggaa actgcacctg | 600 |
| tattcccatc ccatcatctt gggctttcgc aaaatacccta tgggagtggg cctcagtccg | 660 |
| tttctcttgg ctcagtttac tagtgccatt tgttcagtgg ttcgtagggc tttcccccac | 720 |

```
tgtctggctt tcagttatat ggatgatgtg gttttggggg ccaagtctgt acaacatctt    780
gagtccattt ataccgctgt taccaatttt cttttatctt tgggtataca tttaaaccct    840
cacaaaacaa aaagatgggg atattccctt aacttcatgg gatatgtaat tgggagttgg    900
ggcactttgc ctcaggaaca tattgtacaa aaaatcaagc aatgttttag gaaacttcct    960
gtaaacaggc ctattgattg gaaagtatgt caacraattg tgggtctttt ggggtttgcc   1020
gccccttcca cgcaatgtgg atatcctgct ttaatgcctt tatatgcatg tatacaagct   1080
aagcaggctt ttactttctc gccaacttac aaggcctttc tgtgtaaaca atatctgaac   1140
ctttaccccg ttgctcggca acggtcaggt cttttgccaag tgtttgctga cgcaaccccc   1200
actggttggg gcttggccat aggccatcag cgcatgcgtg aacctttgt ggctcctctg   1260
ccgatccata ctgcggaact cctagcagct tgttttgctc gcagccggtc tggagcaaaa   1320
cttatcggca ccgacaactc tgttgtcctc tctcggaaat acacctcctt tccatggctg   1380
ctaggatgtg ctgccaactg gatcctgcgc gggacgtcct ttgtctacgt cccgtcggcg   1440
ctgaatcccg cggacgaccc atctcggggc cgtttgggac tctaccgtcc ccttctgcgt   1500
ctgccgttcc gcccgaccac ggggcgcacc tctctttacg cggtctcccc gtctgtgcct   1560
tctcatctgc cggaccgtgt gcacttcgct tcacctctgc acgtcgcatg gagaccaccg   1620
tgaacgccca cgggaacctg cccaaggtct tgcataagag gactcttgga ctttcagcaa   1680
tgtcaacgac cgaccttgag gcatacttca aagactgtgt gtttactgag tgggaggagt   1740
tgggggagga ggttaggtta aaggtctttg tactaggagg ctgtaggcat aaattggtgt   1800
gttcaccagc accatgcaac ttttcacct ctgcctaatc atctcatgtt catgtcctac   1860
tgttcaagcc tccaagctgt gccttgggtg gctttggggc atggacattg acccgtataa   1920
agaatttgga gcttctgtgg agttactctc ttttttgcct tctgacttct ttccttctat   1980
tcgagatctc ctcgacaccg cctctgctct gtatcgggag ccttagagt ctccggaaca    2040
ttgttcacct caccatacgg cactcaggca agcaattctg tgttgggtg agttaatgaa    2100
tctagccacc tgggtgggaa gtaatttgga agatccagca tccagggaat tagtagtcag    2160
ctatgtcaac gttaatatgg gcctaaaaat cagacaacta ttgtggtttc acatttcctg    2220
tcttactttt gggagagaaa ctgttcttga atattggtg tcttttggag tgtggattcg    2280
cactcctcct gcatatagac cacaaaatgc ccctatctta tcaacacttc cggaaactac    2340
tgttgttaga cgaagaggca ggtcccctag aagaagaact ccctcgcctc gcagacgaag    2400
gtctcaatcg ccgcgtcgca gaagatctca atctcgggaa tctcaatgtt agtattcctt    2460
ggacacataa ggtgggaaac tttacggggc tttattcttc tacggtacct tgctttaatc    2520
ctaaatggca aactccttct tttcctgaca ttcatttgca ggaggacatt gttgatagat    2580
gtaagcaatt tgtgggccc cttacagtaa atgaaaacag gagacttaaa ttaattatgc    2640
ctgctaggtt ttatcccaat gttactaaat atttgccctt agataaaggg atcaaaccgt    2700
attatccaga gtatgtagtt aatcattact ccagacgcg acattattta cacactcttt    2760
ggaaggcggg gatcttatat aaaagagagt ccacacgtag cgcctcattt tgcgggtcac    2820
catattcttg gaacaagat ctacagcatg ggaggttggt cttccaaacc tcgaaaaggc    2880
atggggacaa atctttctgt ccccaatccc ctgggattct tccccgatca tcagttggac    2940
cctgcattca aagccaactc agaaaatcca gattgggacc tcaacccaca caaggacaac    3000
tggccggacg ccaacaaggt gggagtggga gcattcgggc cagggttcac ccctcctcat    3060
gggggactgt tggggtggag ccctcaggct cagggcatat tcacaacagt gccagcagct    3120
```
cctcctcctg cctccaccaa tcggcagtca ggaaggcagc ctactccctt ctctccacct    3180
ctaagagaca ctcatcctca ggccatgcag tggaa                               3215

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgcgtaaaga gaggtg                                                    16

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccggcagatg agaag                                                     15

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aagcgaagtg cacacg                                                    16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggatcagcgc cgacgg                                                    16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaggtgaagc gaagtg                                                    16

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 7
aagagaggtg cgccc                                                          15

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gattcagcgc cgacgg                                                         16

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccgcgtaaag agaggtg                                                        17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gattcagcgc cgacggg                                                        17

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtgaagcgaa gtgca                                                          15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgtgcagagg tgaag                                                          15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
```

```
gggattcagc gccga                                                          15

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggattcagcg ccgacgg                                                        17

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttcagcgccg acggg                                                          15

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggattcagcg ccgacgg                                                        17

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgcgtaaaga gaggtg                                                         16

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgccccgtg gtcgg                                                          15

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```
caccacgagt ctagact                                                    17

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgcgacggga cgta                                                       14

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaacgccgca gacacat                                                    17

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtgcgcccc gtggt                                                      15

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agcgaagtgc acacgg                                                     16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggtgaagcga agtgca                                                     16

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgcagtatgg atcgg                                                      15

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gagaggtgcg ccccgt                                                    16

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gggattcagc gccgacg                                                   17

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gattcagcgc cgacg                                                     15

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gattcagcgc cgacggg                                                   17

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agaggtgcgc cccgtg                                                    16

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gattcagcgc cgacggg                                                   17

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gagaggtgcg ccccg                                                      15

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agagaggtgc gccccgt                                                    17

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aggtgaagcg aagtgc                                                     16

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcgaagtgca cacgg                                                      15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgcgggattc agcgc                                                      15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gagaggtgcg ccccg                                                      15

```
<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aagagaggtg cgccccg                                                   17

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aggtgcgccc cgtgg                                                     15

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccgcagtatg gatcg                                                     15

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccaccacgag tctagac                                                   17

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccgcctgtaa cacgag                                                    16

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gtccgcggga ttcag                                                     15

<210> SEQ ID NO 44
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggtcgtccgc gggattc                                                  17

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
acaaaggacg tcccgcg                                                  17

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggattcagcg ccgacg                                                   16

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggattcagcg ccgacgg                                                  17

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggattcagcg ccgacg                                                   16

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccaccacgag tctagac                                                  17

<210> SEQ ID NO 50
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
agcgaagtgc acacgg                                                       16

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agcgaagtgc acacg                                                        15

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggtgaagcga agtgca                                                       16

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
agcgaagtgc acacg                                                        15

<210> SEQ ID NO 54
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ccgcctgtaa cacgag                                                       16

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gggattcagc gccga                                                        15

<210> SEQ ID NO 56
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 56
gaggtgcgcc ccgtg                                                    15

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aggtgaagcg aagtgc                                                   16

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gccctacgaa ccactga                                                  17

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
acgccgcaga cacat                                                    15

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atgataaaac gccgcag                                                  17

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
attcagcgcc gacgg                                                    15

<210> SEQ ID NO 62
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 62
aaaggacgtc ccgcg                                                        15

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aagagaggtg cgccc                                                        15

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
attcagcgcc gacgg                                                        15

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atgataaaac gccgcag                                                      17

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
acaaaggacg tcccg                                                        15

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggtgaagcga agtgc                                                        15

<210> SEQ ID NO 68
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 68
aacgccgcag acacatc                                                  17

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aaacgccgca gacacat                                                  17

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
acgccgcaga cacat                                                    15

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aggtgaagcg aagtg                                                    15

<210> SEQ ID NO 72
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aacgccgcag acacat                                                   16

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aagcgaagtg cacacg                                                   16

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 74
gataaaacgc cgcagac                                                 17

<210> SEQ ID NO 75
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggtgaagcga agtgca                                                  16

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gccctacgaa ccactga                                                 17

<210> SEQ ID NO 77
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cgcagtatgg atcgg                                                   15

<210> SEQ ID NO 78
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gaggtgcgcc ccgtg                                                   15

<210> SEQ ID NO 79
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
atgataaaac gccgcag                                                 17

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
atgataaaac gccgcag                                                    17

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aaacgccgca gacacat                                                    17

<210> SEQ ID NO 82
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aagagaggtg cgcccc                                                     16

<210> SEQ ID NO 83
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aagcgaagtg cacac                                                      15

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gttgcgtcag caaac                                                      15

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gggaaagccc tacgaac                                                    17

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 86
atgataaaac gccgcag                                                    17

<210> SEQ ID NO 87
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aagacgaagt gcacacg                                                    17

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aagcgaagtg cacaacg                                                    17

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aagcgaagtg caacacg                                                    17

<210> SEQ ID NO 90
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
agcgaagtgc acacgg                                                     16

<210> SEQ ID NO 91
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
agcgaagtgc acacgg                                                     16

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
```
atgataaaac gcgcgcag                                           18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
atgataaaac gcgcgcag                                           18

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
atgataaaac gccgcag                                            17

<210> SEQ ID NO 95
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cgcgtaaaga gaagtg                                             16

<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gattcagcgc cgacggg                                            17

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
ugattcagcg ccgacggg                                           18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 98
ugattcagcg ccgacggg                                                    18

<210> SEQ ID NO 99
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gagaggtgcg ccccgt                                                      16

<210> SEQ ID NO 100
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gagaggtgcg ccccgat                                                     17

<210> SEQ ID NO 101
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gagaggtgcg cccacgt                                                     17

<210> SEQ ID NO 102
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gagaggtgcg ccccgt                                                      16

<210> SEQ ID NO 103
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gagaggtgcg ccccgt                                                      16

<210> SEQ ID NO 104
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
ugagaggtgc gccccgt                                                   17

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
ugagaggtgc gccccgt                                                   17

<210> SEQ ID NO 106
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggattcagcg ccgacg                                                    16

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggattcagcg ccgacg                                                    16

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ggattcagcg ccgacg                                                    16

<210> SEQ ID NO 109
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
```

```
uggattcagc gccgacg                                                    17
```

<210> SEQ ID NO 110
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110

```
uggattcagc gccgacg                                                    17
```

<210> SEQ ID NO 111
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111

```
uggattcagc gccgacg                                                    17
```

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112

```
gataaaacgc cgcagac                                                    17
```

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

```
agataaaacg ccgcagac                                                   18
```

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114

```
agataaaacg ccgcagac                                                   18
```

<210> SEQ ID NO 115
<211> LENGTH: 16
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
ugcgaagtgc acacgg                                                        16

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
accaccacga gtctagac                                                      18

<210> SEQ ID NO 117
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
uggtgaagcg aagtgca                                                       17

<210> SEQ ID NO 118
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gattcagcgc cgacggg                                                       17

<210> SEQ ID NO 119
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggattcagcg ccgacg                                                        16

<210> SEQ ID NO 120
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ccaccacgag tctagac                                                       17
```

```
<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gataaaaacg ccgccagac                                                    19

<210> SEQ ID NO 122
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gattcagcgc cgacgg                                                       16

<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gtgaagcgaa gtgca                                                        15

<210> SEQ ID NO 124
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aagcgaagtg cacacg                                                       16

<210> SEQ ID NO 125
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gattcagcgc cgacggg                                                      17

<210> SEQ ID NO 126
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gaggtgaagc gaagtg                                                       16

<210> SEQ ID NO 127
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ccaccacgag tctagac                                                  17

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gcgaagtgca cacgg                                                    15

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggattcagcg ccgacgg                                                  17

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggtgaagcga agtgc                                                    15

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
agcgaagtgc acacg                                                    15

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aggtgaagcg aagtg                                                    15

<210> SEQ ID NO 133
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aggtgcgccc cgtgg                                                    15

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
caggattcag cgccgacg                                                 18

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cagagaggtg cgccccgt                                                 18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
caaggtgaag cgaagtgc                                                 18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
caggtgaagc gaagtgca                                                 18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
caccgcctgt aacacgag                                                 18

<210> SEQ ID NO 139
<211> LENGTH: 19
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 139
cagataaaac gccgcagac                                              19

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
caccaccacg agtctagac                                              19

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cacaccacga gtctagact                                              19

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
caccgcctgt aacacgag                                               18

<210> SEQ ID NO 143
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gagaggtgcg ccccgt                                                 16

<210> SEQ ID NO 144
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gagaggtgcg ccccgat                                                17

<210> SEQ ID NO 145
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 145
gagaggtgcg cccacgt                                                    17

<210> SEQ ID NO 146
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gagaggtgcg ccccgt                                                     16

<210> SEQ ID NO 147
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gagaggtgcg ccccgt                                                     16

<210> SEQ ID NO 148
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggattcagcg ccgacg                                                     16

<210> SEQ ID NO 149
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggattcagcg ccgacg                                                     16

<210> SEQ ID NO 150
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ggattcagcg ccgacg                                                     16

<210> SEQ ID NO 151
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 151
ggattcagcg ccgacg                                                    16

<210> SEQ ID NO 152
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
uggattcagc gccgacg                                                   17

<210> SEQ ID NO 153
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
uggattcagc gccgacg                                                   17

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
agataaaacg ccgcagac                                                  18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
agataaaacg ccgcagac                                                  18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
```
ugattcagcg ccgacggg                                                    18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
ugattcagcg ccgacggg                                                    18

<210> SEQ ID NO 158
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
ugcgaagtgc acacgg                                                      16

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
uggtgaagcg aagtgca                                                     17

<210> SEQ ID NO 160
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
ugagaggtgc gccccgt                                                     17

<210> SEQ ID NO 161
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
ugagaggugc gccccgu                                                      17

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
accaccacga gtctagac                                                     18

<210> SEQ ID NO 163
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
uggauucagc gccgacg                                                      17

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cgattcagcg ccgacggg                                                     18

<210> SEQ ID NO 165
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gtgaagcgaa gtgca                                                        15

<210> SEQ ID NO 166
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
agcgaagtgc acacgg                                                       16

<210> SEQ ID NO 167
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 167
gtgaagcgaa gtgca                                                    15

<210> SEQ ID NO 168
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aagcgaagtg cacacg                                                   16

<210> SEQ ID NO 169
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gattcagcgc cgacgg                                                   16

<210> SEQ ID NO 170
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cgcgtaaaga gaggtg                                                   16

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ggattcagcg ccgacgg                                                  17

<210> SEQ ID NO 172
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gaggtgaagc gaagtg                                                   16

<210> SEQ ID NO 173
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 173
ccgcgtaaag agaggtg                                                17

<210> SEQ ID NO 174
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gattcagcgc cgacggg                                                17

<210> SEQ ID NO 175
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ccaccacgag tctagac                                                17

<210> SEQ ID NO 176
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
atgataaaac gccgcag                                                17

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gccctacgaa ccactga                                                17

<210> SEQ ID NO 178
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
agcgaagtgc acacgg                                                 16

<210> SEQ ID NO 179
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cgcgggattc agcgc                                                      15

<210> SEQ ID NO 180
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gcgaagtgca cacgg                                                      15

<210> SEQ ID NO 181
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggtgcgcccc gtggg                                                      15

<210> SEQ ID NO 182
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ggtgaagcga agtgc                                                      15

<210> SEQ ID NO 183
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggattcagcg ccgacgg                                                    17

<210> SEQ ID NO 184
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gaggtgaagc gaagtg                                                     16

<210> SEQ ID NO 185
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
agcgaagtgc acacg                                                    15

<210> SEQ ID NO 186
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aggtgaagcg aagtg                                                    15

<210> SEQ ID NO 187
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gcgccccgtg gtcgg                                                    15

<210> SEQ ID NO 188
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aggtgcgccc cgtgg                                                    15

<210> SEQ ID NO 189
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cgcgtaaaga gaggtg                                                   16

<210> SEQ ID NO 190
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
cgcgtaaaga gaggtg                                                   16

<210> SEQ ID NO 191
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cgcgtaaaga gaggtg                                                   16

<210> SEQ ID NO 192
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gattcagcgc cgacggg                                                  17

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
atgataaaac gccgcag                                                  17

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
caatgataaa acgccgcag                                                19

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
caatgataaa acgccgcag                                                19

<210> SEQ ID NO 196
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gattcagcgc cgacggg                                                  17

<210> SEQ ID NO 197
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cgcgtaaaga gaggtg                                                   16

```
<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cagattcagc gccgacggg                                                   19

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gattcagcgc cgacgggc                                                    18

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gattcagcgc cgacgggca                                                   19

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cgattcagcg ccgacggg                                                    18

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
cagattcagc gccgacggg                                                   19

<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gattcagcgc cgacgggc                                                    18
```

```
<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gattcagcgc cgacgggca                                                    19

<210> SEQ ID NO 205
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ccaccacgag tctagac                                                      17

<210> SEQ ID NO 206
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ccaccacgag tctagac                                                      17

<210> SEQ ID NO 207
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gcgaagtgca cacgg                                                        15

<210> SEQ ID NO 208
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gcgaagtgca cacgg                                                        15

<210> SEQ ID NO 209
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gcgaagtgca cacgg                                                        15

<210> SEQ ID NO 210
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gcgaagtgca cacgg                                                        15

<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gcgaagtgca cacgg                                                        15

<210> SEQ ID NO 212
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gcgaagtgca cacgg                                                        15

<210> SEQ ID NO 213
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gattcagcgc cgacggag                                                     18

<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gattcagcgc cgacgagg                                                     18

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gattcagcgc cgacaggg                                                     18

<210> SEQ ID NO 216
<211> LENGTH: 17
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gattcagcgc cgacggg                                                    17

<210> SEQ ID NO 217
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gattcagcgc cgacggg                                                    17

<210> SEQ ID NO 218
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gaattcagcg ccgacggg                                                   18

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
agattcagcg ccgacggg                                                   18

<210> SEQ ID NO 220
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
caggattcag cgccgacgg                                                  19

<210> SEQ ID NO 221
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
caaagagagg tgcgccc                                                    17

<210> SEQ ID NO 222
<211> LENGTH: 17
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 222
gattcagcgc cgacggg                                                    17

<210> SEQ ID NO 223
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gattcagcgc cgacggg                                                    17

<210> SEQ ID NO 224
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gattcagcgc cgacggg                                                    17

<210> SEQ ID NO 225
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gattcagcgc cgacggg                                                    17

<210> SEQ ID NO 226
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gattcagcgc cgacggg                                                    17

<210> SEQ ID NO 227
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gattcagcgc cgacggg                                                    17

<210> SEQ ID NO 228
<211> LENGTH: 17
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 228
gattcagcgc cgacggg                                                    17

<210> SEQ ID NO 229
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccaccacgag tctagac                                                    17

<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ccaccacgag tctagac                                                    17

<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ccaccacgag tctagac                                                    17

<210> SEQ ID NO 232
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ccaccacgag tctagac                                                    17

<210> SEQ ID NO 233
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gcgaagtgca cacgga                                                     16

<210> SEQ ID NO 234
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 234
gcgaagtgca cacggc                                                      16

<210> SEQ ID NO 235
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gcgaagtgca cacggg                                                      16

<210> SEQ ID NO 236
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gcgaagtgca cacgga                                                      16

<210> SEQ ID NO 237
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gcgaagtgca cacggc                                                      16

<210> SEQ ID NO 238
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gcgaagtgca cacggg                                                      16

<210> SEQ ID NO 239
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ccaccacgag tctagaca                                                    18

<210> SEQ ID NO 240
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 240
ccaccacgag tctagacc                                                   18

<210> SEQ ID NO 241
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ccaccacgag tctagacg                                                   18

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ccaccacgag tctagaca                                                   18

<210> SEQ ID NO 243
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ccaccacgag tctaga                                                     16

<210> SEQ ID NO 244
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gataaaacgc cgcagact                                                   18

<210> SEQ ID NO 245
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gataaaacgc cgcagacc                                                   18

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 246
gataaaacgc cgcagacg                                                 18

<210> SEQ ID NO 247
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
gataaaacgc cgcagacu                                                 18

<210> SEQ ID NO 248
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gataaaacgc cgcagacc                                                 18

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gataaaacgc cgcagacg                                                 18

<210> SEQ ID NO 250
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gataaaacgc cgcagac                                                  17

<210> SEQ ID NO 251
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
ggtgaagcga agtgcau                                                  17

<210> SEQ ID NO 252
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gcgaagtgca cacgga                                                      16

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gataaaacgc cgcagact                                                    18

<210> SEQ ID NO 254
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
uggtgaagcg aagtgca                                                     17

<210> SEQ ID NO 255
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tgcgaagtgc acacgg                                                      16

<210> SEQ ID NO 256
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
ugcgaagtgc acacgg                                                      16

<210> SEQ ID NO 257
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 257
ugcgaagtgc acacgg                                                    16

<210> SEQ ID NO 258
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
agataaaacg ccgcagac                                                  18

<210> SEQ ID NO 259
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
agataaaacg ccgcagac                                                  18

<210> SEQ ID NO 260
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
accaccacga gtctagac                                                  18

<210> SEQ ID NO 261
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ggattcagcg ccgacga                                                   17

<210> SEQ ID NO 262
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gagaggtgcg ccccgta                                                   17

<210> SEQ ID NO 263
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 263
uggattcagc gccgacg                                                   17

<210> SEQ ID NO 264
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
ugagaggtgc gccccgt                                                   17

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
ugattcagcg ccgacggg                                                  18

<210> SEQ ID NO 266
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 266
gattcagcgc cgacgggu                                                  18

<210> SEQ ID NO 267
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
cagattcagc gccgacgg                                                  18

<210> SEQ ID NO 268
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
```
cagtgaagcg agtgca                                                   16

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
cagattcagc gccgacggg                                                19

<210> SEQ ID NO 270
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
caagcgaagt gcacacgg                                                 18

<210> SEQ ID NO 271
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
caacgccgca gacacat                                                  17

<210> SEQ ID NO 272
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
cagagaggtg cgccccgt                                                 18

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
caggattcag cgccgacg                                                 18

<210> SEQ ID NO 274
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
caccgcctgt aacacgag                                                 18

<210> SEQ ID NO 275
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
caccgcctgt aacacgag                                                   18

<210> SEQ ID NO 276
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
cagataaaac gccgcagac                                                  19

<210> SEQ ID NO 277
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cacaccacga gtctagact                                                  19

<210> SEQ ID NO 278
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
caatgataaa acgccgcag                                                  19

<210> SEQ ID NO 279
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
caccaccacg agtctagac                                                  19

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
cagccctacg aaccactga                                                  19

<210> SEQ ID NO 281
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
caaaacgccg cagacacat                                                19

<210> SEQ ID NO 282
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
caaggtgaag cgaagtgc                                                 18

<210> SEQ ID NO 283
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
caggtgaagc gaagtgca                                                 18

<210> SEQ ID NO 284
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ggattcagcg ccgacg                                                   16

<210> SEQ ID NO 285
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
cagcgaagtg cacacgg                                                  17

<210> SEQ ID NO 286
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ggattcagcg ccgacg                                                   16

```
<210> SEQ ID NO 287
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggattcagcg ccgacg                                                       16

<210> SEQ ID NO 288
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ggattcagcg ccgacg                                                       16

<210> SEQ ID NO 289
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gattcagcgc cgacggg                                                      17

<210> SEQ ID NO 290
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gattcagcgc cgacggg                                                      17

<210> SEQ ID NO 291
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ccaccacgag tctagac                                                      17

<210> SEQ ID NO 292
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
ccaccacgag tctagac                                                      17

<210> SEQ ID NO 293
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ccaccacgag tctagac                                                    17

<210> SEQ ID NO 294
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
caagcgaagt gcacacg                                                    17

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gataaaacgc cgcagac                                                    17

<210> SEQ ID NO 296
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
gataaaacgc cgcagac                                                    17

<210> SEQ ID NO 297
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
gataaaacgc cgcagac                                                    17

<210> SEQ ID NO 298
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ggattcagcg ccgacg                                                     16

<210> SEQ ID NO 299
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ggattcagcg ccgacg                                                    16

<210> SEQ ID NO 300
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gagaggtgcg ccccgt                                                    16

<210> SEQ ID NO 301
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gagaggtgcg ccccgt                                                    16

<210> SEQ ID NO 302
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
gagaggtgcg ccccgt                                                    16

<210> SEQ ID NO 303
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gagaggtgcg ccccgt                                                    16

<210> SEQ ID NO 304
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
gagaggtgcg ccccgt                                                    16

<210> SEQ ID NO 305
<211> LENGTH: 19
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 305
caagagaggt gcgccccgt                                                19

<210> SEQ ID NO 306
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 306
caacaaagga cgtcccgcg                                                19

<210> SEQ ID NO 307
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 307
caatgataaa acgccgcag                                                19

<210> SEQ ID NO 308
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 308
caccgcgtaa agagaggtg                                                19

<210> SEQ ID NO 309
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
gattcagcgc cgacggg                                                  17

<210> SEQ ID NO 310
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 310
gataaaacgc cgcagact                                                 18

<210> SEQ ID NO 311
<211> LENGTH: 16
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 311
gcgaagtgca cacgga                                                      16

<210> SEQ ID NO 312
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gcgaagtgca cacgga                                                      16

<210> SEQ ID NO 313
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gcgaagtgca cacgga                                                      16

<210> SEQ ID NO 314
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gcgaagtgca cacgga                                                      16

<210> SEQ ID NO 315
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gcgaagtgca cacgga                                                      16

<210> SEQ ID NO 316
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gataaaacgc cgcagact                                                    18

<210> SEQ ID NO 317
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 317
gataaaacgc cgcagact                                                 18

<210> SEQ ID NO 318
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gataaaacgc cgcagact                                                 18

<210> SEQ ID NO 319
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gataaaacgc cgcagact                                                 18

<210> SEQ ID NO 320
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gcgaagtgca cacgga                                                   16

<210> SEQ ID NO 321
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gcgaagtgca cacgga                                                   16

<210> SEQ ID NO 322
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gcgaagtgca cacgga                                                   16

<210> SEQ ID NO 323
<211> LENGTH: 16
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 323
gcgaagtgca cacgga                                                    16

<210> SEQ ID NO 324
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gcgaagtgca cacgga                                                    16

<210> SEQ ID NO 325
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gataaaacgc cgcagact                                                  18

<210> SEQ ID NO 326
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
gataaaacgc cgcagact                                                  18

<210> SEQ ID NO 327
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gataaaacgc cgcagact                                                  18

<210> SEQ ID NO 328
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gataaaacgc cgcagact                                                  18

<210> SEQ ID NO 329
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 329
gataaaacgc cgcagact                                                 18

<210> SEQ ID NO 330
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
ccaccacgag tctagaca                                                 18

<210> SEQ ID NO 331
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ccaccacgag tctagaca                                                 18

<210> SEQ ID NO 332
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
ccaccacgag tctagaca                                                 18

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
ccaccacgag tctagaca                                                 18

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ccaccacgag tctagaca                                                 18

<210> SEQ ID NO 335
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 335
gataaaacgc cgcagact                                                18

<210> SEQ ID NO 336
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
gcgaagtgca cacgga                                                  16

<210> SEQ ID NO 337
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gataaaacgc cgcagact                                                18

<210> SEQ ID NO 338
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
ggtgaagcga agtgcaa                                                 17

<210> SEQ ID NO 339
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
ggtgaagcga agtgcaa                                                 17

<210> SEQ ID NO 340
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ggtgaagcga agtgcaa                                                 17

<210> SEQ ID NO 341
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
ggtgaagcga agtgcaa                                               17

<210> SEQ ID NO 342
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
ggtgaagcga agtgcaa                                               17

<210> SEQ ID NO 343
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
ggtgaagcga agtgcaa                                               17

<210> SEQ ID NO 344
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gataaaacgc cgcagact                                              18

<210> SEQ ID NO 345
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gataaaacgc cgcagact                                              18

<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ccaccacgag tctagaca                                              18

<210> SEQ ID NO 347
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ccaccacgag tctagaca                                                 18

<210> SEQ ID NO 348
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
ccaccacgag tctagaca                                                 18

<210> SEQ ID NO 349
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gataaaacgc cgcagact                                                 18

<210> SEQ ID NO 350
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gataaaacgc cgcagact                                                 18

<210> SEQ ID NO 351
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gataaaacgc cgcagact                                                 18

<210> SEQ ID NO 352
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ggtgaagcga agtgcaa                                                  17

<210> SEQ ID NO 353
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
gataaaacgc cgcagact                                                 18

<210> SEQ ID NO 354
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
gataaaacgc cgcagact                                                 18

<210> SEQ ID NO 355
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
ggtgaagcga agtgcaa                                                  17

<210> SEQ ID NO 356
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
ggtgaagcga agtgcaa                                                  17

<210> SEQ ID NO 357
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
ggtgaagcga agtgcaa                                                  17

<210> SEQ ID NO 358
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ggtgaagcga agtgcaa                                                  17

<210> SEQ ID NO 359
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
ggattcagcg ccgacga                                                  17

<210> SEQ ID NO 360
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
ggattcagcg ccgacga                                                   17

<210> SEQ ID NO 361
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
ggattcagcg ccgacga                                                   17

<210> SEQ ID NO 362
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
ggattcagcg ccgacga                                                   17

<210> SEQ ID NO 363
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
ggattcagcg ccgacga                                                   17

<210> SEQ ID NO 364
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ggattcagcg ccgacga                                                   17

<210> SEQ ID NO 365
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gagaggtgcg ccccgta                                                   17

```
<210> SEQ ID NO 366
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gattcagcgc cgacgggt                                                       18

<210> SEQ ID NO 367
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gagaggtgcg ccccgta                                                        17

<210> SEQ ID NO 368
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
ccaccacgag tctagaca                                                       18

<210> SEQ ID NO 369
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
ccaccacgag tctagaca                                                       18

<210> SEQ ID NO 370
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
ccaccacgag tctagaca                                                       18

<210> SEQ ID NO 371
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
ccaccacgag tctagaca                                                       18

<210> SEQ ID NO 372
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
gcgaagtgca cacgga                                                    16

<210> SEQ ID NO 373
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
gataaaacgc cgcagact                                                  18

<210> SEQ ID NO 374
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gcgaagtgca cacgga                                                    16

<210> SEQ ID NO 375
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gagaggtgcg ccccgta                                                   17

<210> SEQ ID NO 376
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 376
ugcgaagtgc acacgg                                                    16

<210> SEQ ID NO 377
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ggattcagcg ccgacga                                                   17
```

```
<210> SEQ ID NO 378
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
ggattcagcg ccgacga                                                   17

<210> SEQ ID NO 379
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
cagcgaagtg cacacgg                                                   17

<210> SEQ ID NO 380
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
cagcgaagtg cacacgg                                                   17

<210> SEQ ID NO 381
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
cagcgaagtg cacacgg                                                   17

<210> SEQ ID NO 382
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
caggtgaagc gaagtgca                                                  18

<210> SEQ ID NO 383
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
gcgaagtgca cacggg                                                    16
```

```
<210> SEQ ID NO 384
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
ccaccacgag tctagacg                                                 18

<210> SEQ ID NO 385
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
cagataaaac gccgcagac                                                19

<210> SEQ ID NO 386
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
cagataaaac gccgcagac                                                19

<210> SEQ ID NO 387
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
cagataaaac gccgcagac                                                19

<210> SEQ ID NO 388
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
caccaccacg agtctagac                                                19

<210> SEQ ID NO 389
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
caccaccacg agtctagac                                                19

<210> SEQ ID NO 390
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
caccaccacg agtctagac                                                   19

<210> SEQ ID NO 391
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
ccaccacgag tctagaca                                                    18

<210> SEQ ID NO 392
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
gattcagcgc cgacgggt                                                    18

<210> SEQ ID NO 393
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
gattcagcgc cgacgggt                                                    18

<210> SEQ ID NO 394
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gattcagcgc cgacgggt                                                    18

<210> SEQ ID NO 395
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
ccaccacgag tctagaca                                                    18

<210> SEQ ID NO 396
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
agataaaacg ccgcagac                                                   18

<210> SEQ ID NO 397
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
agataaaacg ccgcagac                                                   18

<210> SEQ ID NO 398
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
accaccacga gtctagac                                                   18

<210> SEQ ID NO 399
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
accaccacga gtctagac                                                   18

<210> SEQ ID NO 400
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
agataaaacg ccgcagac                                                   18

<210> SEQ ID NO 401
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
agataaaacg ccgcagac                                                   18

<210> SEQ ID NO 402
<211> LENGTH: 17
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 402
aggtgaagcg aagtgca                                                      17

<210> SEQ ID NO 403
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
ccaccacgag tctagaca                                                     18

<210> SEQ ID NO 404
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gattcagcgc cgacggg                                                      17

<210> SEQ ID NO 405
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gataaaacgc cgcagac                                                      17

<210> SEQ ID NO 406
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gattcagcgc cgacggg                                                      17

<210> SEQ ID NO 407
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ccaccacgag tctagac                                                      17

<210> SEQ ID NO 408
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
gagaggtgcg ccccgt                                                      16

<210> SEQ ID NO 409
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ggattcagcg ccgacg                                                      16

<210> SEQ ID NO 410
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gagaggtgcg ccccgt                                                      16

<210> SEQ ID NO 411
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
cagataaaac gccgcagac                                                   19

<210> SEQ ID NO 412
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
cagataaaac gccgcagac                                                   19

<210> SEQ ID NO 413
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
cagataaaac gccgcagac                                                   19

<210> SEQ ID NO 414
<211> LENGTH: 18
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 414
ccaccacgag tctagaca                                                  18

<210> SEQ ID NO 415
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
caccaccacg agtctagac                                                 19

<210> SEQ ID NO 416
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
caccaccacg agtctagac                                                 19

<210> SEQ ID NO 417
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
caccaccacg agtctagac                                                 19

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
gcagaggtga agcgaagtgc                                                20

<210> SEQ ID NO 419
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 419
uggattcagc gccgacg                                                   17

<210> SEQ ID NO 420
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 420
agataaaacg ccgcagac                                                 18

<210> SEQ ID NO 421
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
gataaaacgc cgcagac                                                  17

<210> SEQ ID NO 422
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 422
ugattcagcg ccgacggg                                                 18

<210> SEQ ID NO 423
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
cagattcagc gccgacggg                                                19

<210> SEQ ID NO 424
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
caagcgaagt gcacacgg                                                 18

<210> SEQ ID NO 425
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
cagagaggtg cgccccgt                                                 18

<210> SEQ ID NO 426
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
caggattcag cgccgacg                                                    18

<210> SEQ ID NO 427
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
caccaccacg agtctagac                                                   19

<210> SEQ ID NO 428
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
ggattcagcg ccgacga                                                     17
```